(12) United States Patent
Shanjani et al.

(10) Patent No.: US 10,980,613 B2
(45) Date of Patent: Apr. 20, 2021

(54) AUGMENTED REALITY ENHANCEMENTS FOR DENTAL PRACTITIONERS

(71) Applicant: Align Technology, Inc., San Jose, CA (US)

(72) Inventors: Yaser Shanjani, Milpitas, CA (US); Bruce Cam, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 33 days.

(21) Appl. No.: 16/231,906

(22) Filed: Dec. 24, 2018

(65) Prior Publication Data

US 2019/0269482 A1 Sep. 5, 2019

Related U.S. Application Data

(60) Provisional application No. 62/612,308, filed on Dec. 29, 2017.

(51) Int. Cl.
*A61C 7/00* (2006.01)
*A61C 9/00* (2006.01)
(Continued)

(52) U.S. Cl.
CPC .............. *A61C 7/002* (2013.01); *A61B 34/00* (2016.02); *A61B 90/361* (2016.02); *A61C 7/146* (2013.01); *A61C 9/0046* (2013.01); *G06F 3/011* (2013.01); *G06F 3/013* (2013.01); *G06F 3/017* (2013.01); *G06T 19/006* (2013.01);
(Continued)

(58) Field of Classification Search
CPC ....... A61C 7/002; A61C 7/146; A61C 9/0046; A61C 9/0053; A61B 34/00; A61B 90/361; A61B 2090/365; G06F 3/013; G06F 3/011; G06F 3/017; G06T 19/006; G06T 2210/41; G02B 27/017; G02B 2027/0178; G02B 2027/0138; G02B 27/0172

See application file for complete search history.

(56) References Cited

U.S. PATENT DOCUMENTS 2,171,695 A 9/1939 Harper
2,194,790 A 3/1940 Gluck
(Continued)

FOREIGN PATENT DOCUMENTS

AU 517102 B 11/1977
AU 3031677 A 11/1977
(Continued)

OTHER PUBLICATIONS

US 8,553,966 B1, 10/2013, Alpern et al. (withdrawn)
(Continued)

*Primary Examiner* — Ming Y Hon
(74) *Attorney, Agent, or Firm* — Shay Glenn LLP

(57) ABSTRACT

Apparatuses and methods for performing orthodontic treatment planning are provided. Virtual/Augmented Reality devices can be used to virtually manipulate patient's teeth, modify virtual models of the patient's teeth, analyze the fit of a dental appliance on the patient's teeth, analyze the position of attachment sites for dental appliances, and provide overlays showing forces applied to the patient's teeth. The VR/AR devices can be used by physicians and/or the patient to provide and display treatment planning.

19 Claims, 12 Drawing Sheets

---

Receive (e.g., in a processor of the AR system) a first data set comprising a treatment plan for a patient's teeth 458.

Receive (receive, from an augmented reality system worn by a dental practitioner, an image data set comprising a representation of the patient's current teeth 460.

Compare the first data set to the image data set to determine one or more variations from the treatment plan 462.

Displaying the one or more variations on a visual display of the augmented reality system worn by the dental practitioner superimposed over a view of the patient's teeth 464.

(51) Int. Cl.
    *G06T 19/00* (2011.01)
    *A61B 34/00* (2016.01)
    *A61B 90/00* (2016.01)
    *G06F 3/01* (2006.01)
    *A61C 7/14* (2006.01)
    *G02B 27/01* (2006.01)

(52) U.S. Cl.
    CPC ........ *A61B 2090/365* (2016.02); *A61C 9/0053* (2013.01); *G02B 27/017* (2013.01); *G06T 2210/41* (2013.01)

(56) References Cited

U.S. PATENT DOCUMENTS

| | | |
|---|---|---|
| 2,467,432 A | 4/1949 | Kesling |
| 2,531,222 A | 11/1950 | Kesling |
| 3,089,487 A | 5/1963 | Enicks et al. |
| 3,092,907 A | 6/1963 | Traiger |
| 3,178,820 A | 4/1965 | Kesling |
| 3,211,143 A | 10/1965 | Grossberg |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,724,075 A | 4/1973 | Kesling |
| 3,738,005 A | 6/1973 | Cohen et al. |
| 3,797,115 A | 3/1974 | Silverman et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,949,477 A | 4/1976 | Cohen et al. |
| 3,950,851 A | 4/1976 | Bergersen |
| 3,955,282 A | 5/1976 | McNall |
| 3,983,628 A | 10/1976 | Acevedo |
| 4,014,096 A | 3/1977 | Dellinger |
| 4,055,895 A | 11/1977 | Huge |
| 4,094,068 A | 6/1978 | Schinhammer |
| 4,117,596 A | 10/1978 | Wallshein |
| 4,129,946 A | 12/1978 | Kennedy |
| 4,134,208 A | 1/1979 | Pearlman |
| 4,139,944 A | 2/1979 | Bergersen |
| 4,179,811 A | 12/1979 | Hinz |
| 4,179,812 A | 12/1979 | White |
| 4,183,141 A | 1/1980 | Dellinger |
| 4,195,046 A | 3/1980 | Kesling |
| 4,204,325 A | 5/1980 | Kaelble |
| 4,253,828 A | 3/1981 | Coles et al. |
| 4,255,138 A | 3/1981 | Frohn |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,368,040 A | 1/1983 | Weissman |
| 4,419,992 A | 12/1983 | Chorbajian |
| 4,433,956 A | 2/1984 | Witzig |
| 4,433,960 A | 2/1984 | Garito et al. |
| 4,439,154 A | 3/1984 | Mayclin |
| 4,449,928 A | 5/1984 | von Weissenfluh |
| 4,478,580 A | 10/1984 | Barrut |
| 4,500,294 A | 2/1985 | Lewis |
| 4,505,672 A | 3/1985 | Kurz |
| 4,505,673 A | 3/1985 | Yoshii |
| 4,519,386 A | 5/1985 | Sullivan |
| 4,523,908 A | 6/1985 | Drisaldi et al. |
| 4,526,540 A | 7/1985 | Dellinger |
| 4,553,936 A | 11/1985 | Wang |
| 4,575,330 A | 3/1986 | Hull |
| 4,575,805 A | 3/1986 | Moermann et al. |
| 4,591,341 A | 5/1986 | Andrews |
| 4,608,021 A | 8/1986 | Barrett |
| 4,609,349 A | 9/1986 | Cain |
| 4,611,288 A | 9/1986 | Duret et al. |
| 4,629,424 A | 12/1986 | Lauks et al. |
| 4,638,145 A | 1/1987 | Sakuma et al. |
| 4,656,860 A | 4/1987 | Orthuber et al. |
| 4,663,720 A | 5/1987 | Duret et al. |
| 4,664,626 A | 5/1987 | Kesling |
| 4,665,621 A | 5/1987 | Ackerman et al. |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,790,752 A | 12/1988 | Cheslak |
| 4,793,803 A | 12/1988 | Martz |
| 4,798,534 A | 1/1989 | Breads |
| 4,830,612 A | 5/1989 | Bergersen |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,932,866 A | 6/1990 | Guis |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,971,557 A | 11/1990 | Martin |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,015,183 A | 5/1991 | Fenick |
| 5,017,133 A | 5/1991 | Miura |
| 5,018,969 A | 5/1991 | Andreiko et al. |
| 5,027,281 A | 6/1991 | Rekow et al. |
| 5,035,613 A | 7/1991 | Breads et al. |
| 5,037,295 A | 8/1991 | Bergersen |
| 5,055,039 A | 10/1991 | Abbatte et al. |
| 5,061,839 A | 10/1991 | Matsuno et al. |
| 5,083,919 A | 1/1992 | Quachi |
| 5,094,614 A | 3/1992 | Wildman |
| 5,100,316 A | 3/1992 | Wildman |
| 5,103,838 A | 4/1992 | Yousif |
| 5,114,339 A | 5/1992 | Guis |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,194,003 A | 3/1993 | Garay et al. |
| 5,204,670 A | 4/1993 | Stinton |
| 5,222,499 A | 6/1993 | Allen et al. |
| 5,224,049 A | 6/1993 | Mushabac |
| 5,238,404 A | 8/1993 | Andreiko |
| 5,242,304 A | 9/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,314,335 A | 5/1994 | Fung |
| 5,324,186 A | 6/1994 | Bakanowski |
| 5,328,362 A | 7/1994 | Watson et al. |
| 5,335,657 A | 8/1994 | Terry et al. |
| 5,338,198 A | 8/1994 | Wu et al. |

(56) References Cited

U.S. PATENT DOCUMENTS

| | | |
|---|---|---|
| 5,340,309 A | 8/1994 | Robertson |
| 5,342,202 A | 8/1994 | Deshayes |
| 5,344,315 A | 9/1994 | Hanson |
| 5,368,478 A | 11/1994 | Andreiko et al. |
| 5,372,502 A | 12/1994 | Massen et al. |
| D354,355 S | 1/1995 | Hilgers |
| 5,382,164 A | 1/1995 | Stern |
| 5,395,238 A | 3/1995 | Andreiko et al. |
| 5,415,542 A | 5/1995 | Kesling |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,449,703 A | 9/1995 | Mitra et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,487,662 A | 1/1996 | Kipke et al. |
| RE35,169 E | 3/1996 | Lemchen et al. |
| 5,499,633 A | 3/1996 | Fenton |
| 5,522,725 A | 6/1996 | Jordan et al. |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,575,655 A | 11/1996 | Darnell |
| 5,583,977 A | 12/1996 | Seidl |
| 5,587,912 A | 12/1996 | Andersson et al. |
| 5,588,098 A | 12/1996 | Chen et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,636,736 A | 6/1997 | Jacobs et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,711,665 A | 1/1998 | Adam et al. |
| 5,711,666 A | 1/1998 | Hanson |
| 5,725,376 A | 3/1998 | Poirier |
| 5,725,378 A | 3/1998 | Wang |
| 5,730,151 A | 3/1998 | Summer et al. |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,162 A | 9/1998 | Shimodaira et al. |
| 5,800,174 A | 9/1998 | Andersson |
| 5,813,854 A | 9/1998 | Nikodem |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,876,199 A | 3/1999 | Bergersen |
| 5,879,158 A | 3/1999 | Doyle et al. |
| 5,880,961 A | 3/1999 | Crump |
| 5,880,962 A | 3/1999 | Andersson et al. |
| 5,882,192 A | 3/1999 | Bergersen |
| 5,886,702 A | 3/1999 | Migdal et al. |
| 5,890,896 A | 4/1999 | Padial |
| 5,904,479 A | 5/1999 | Staples |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,975,906 A | 11/1999 | Knutson |
| 5,980,246 A | 11/1999 | Ramsay et al. |
| 5,989,023 A | 11/1999 | Summer et al. |
| 6,002,706 A | 12/1999 | Stayer et al. |
| 6,018,713 A | 1/2000 | Coli et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,070,140 A | 5/2000 | Tran |
| 6,099,303 A | 8/2000 | Gibbs et al. |
| 6,099,314 A | 8/2000 | Kopelman et al. |
| 6,102,701 A | 8/2000 | Engeron |
| 6,120,287 A | 9/2000 | Chen |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,183,249 B1 | 2/2001 | Brennan et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,210,162 B1 | 4/2001 | Chishti et al. |
| 6,212,435 B1 | 4/2001 | Lattner et al. |
| 6,213,767 B1 | 4/2001 | Dixon et al. |
| 6,217,334 B1 | 4/2001 | Hultgren |
| 6,227,850 B1 | 5/2001 | Chishti et al. |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,283,761 B1 | 9/2001 | Joao |
| 6,288,138 B1 | 9/2001 | Yamamoto |
| 6,299,438 B1 | 10/2001 | Sahagian et al. |
| 6,309,215 B1 | 10/2001 | Phan et al. |
| 6,313,432 B1 | 11/2001 | Nagata et al. |
| 6,315,553 B1 | 11/2001 | Sachdeva et al. |
| 6,328,745 B1 | 12/2001 | Ascherman |
| 6,332,774 B1 | 12/2001 | Chikami |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,386,878 B1 | 5/2002 | Pavlovskaia et al. |
| 6,394,802 B1 | 5/2002 | Hahn |
| 6,402,510 B1 | 6/2002 | Williams |
| 6,402,707 B1 | 6/2002 | Ernst |
| 6,405,729 B1 | 6/2002 | Thornton |
| 6,406,292 B1 | 6/2002 | Chishti et al. |
| 6,409,504 B1 | 6/2002 | Jones et al. |
| 6,413,086 B1 | 7/2002 | Womack |
| 6,414,264 B1 | 7/2002 | von Falkenhausen |
| 6,414,708 B1 | 7/2002 | Carmeli et al. |
| 6,435,871 B1 | 8/2002 | Inman |
| 6,436,058 B1 | 8/2002 | Krahner et al. |
| 6,441,354 B1 | 8/2002 | Seghatol et al. |
| 6,450,167 B1 | 9/2002 | David et al. |
| 6,450,807 B1 | 9/2002 | Chishti et al. |
| 6,462,301 B1 | 10/2002 | Scott et al. |
| 6,470,338 B1 | 10/2002 | Rizzo et al. |
| 6,471,511 B1 | 10/2002 | Chishti et al. |
| 6,471,512 B1 | 10/2002 | Sachdeva et al. |
| 6,471,970 B1 | 10/2002 | Fanara et al. |
| 6,482,002 B2 | 11/2002 | Jordan et al. |
| 6,482,298 B1 | 11/2002 | Bhatnagar |
| 6,496,814 B1 | 12/2002 | Busche |
| 6,496,816 B1 | 12/2002 | Thiesson et al. |
| 6,499,026 B1 | 12/2002 | Rivette et al. |
| 6,499,995 B1 | 12/2002 | Schwartz |
| 6,507,832 B1 | 1/2003 | Evans et al. |

(56) References Cited

U.S. PATENT DOCUMENTS

| | | |
|---|---|---|
| 6,514,074 B1 | 2/2003 | Chishti et al. |
| 6,515,593 B1 | 2/2003 | Stark et al. |
| 6,516,288 B2 | 2/2003 | Bagne |
| 6,516,805 B1 | 2/2003 | Thornton |
| 6,520,772 B2 | 2/2003 | Williams |
| 6,523,009 B1 | 2/2003 | Wilkins |
| 6,523,019 B1 | 2/2003 | Borthwick |
| 6,524,101 B1 | 2/2003 | Phan et al. |
| 6,526,168 B1 | 2/2003 | Ornes et al. |
| 6,526,982 B1 | 3/2003 | Strong |
| 6,529,891 B1 | 3/2003 | Heckerman |
| 6,529,902 B1 | 3/2003 | Kanevsky et al. |
| 6,532,455 B1 | 3/2003 | Martin et al. |
| 6,535,865 B1 | 3/2003 | Skaaning et al. |
| 6,540,512 B1 | 4/2003 | Sachdeva et al. |
| 6,540,707 B1 | 4/2003 | Stark et al. |
| 6,542,593 B1 | 4/2003 | Bowman Amuah |
| 6,542,881 B1 | 4/2003 | Meidan et al. |
| 6,542,894 B1 | 4/2003 | Lee et al. |
| 6,542,903 B2 | 4/2003 | Hull et al. |
| 6,551,243 B2 | 4/2003 | Bocionek et al. |
| 6,554,837 B1 | 4/2003 | Hauri et al. |
| 6,556,659 B1 | 4/2003 | Bowman Amuah |
| 6,556,977 B1 | 4/2003 | Lapointe et al. |
| 6,560,592 B1 | 5/2003 | Reid et al. |
| 6,564,209 B1 | 5/2003 | Dempski et al. |
| 6,567,814 B1 | 5/2003 | Bankier et al. |
| 6,571,227 B1 | 5/2003 | Agrafiotis et al. |
| 6,572,372 B1 | 6/2003 | Phan et al. |
| 6,573,998 B2 | 6/2003 | Cohen Sabban |
| 6,574,561 B2 | 6/2003 | Alexander et al. |
| 6,578,003 B1 | 6/2003 | Camarda et al. |
| 6,580,948 B2 | 6/2003 | Haupert et al. |
| 6,587,529 B1 | 7/2003 | Staszewski et al. |
| 6,587,828 B1 | 7/2003 | Sachdeva |
| 6,592,368 B1 | 7/2003 | Weathers |
| 6,594,539 B1 | 7/2003 | Geng |
| 6,595,342 B1 | 7/2003 | Maritzen et al. |
| 6,597,934 B1 | 7/2003 | de Jong et al. |
| 6,598,043 B1 | 7/2003 | Baclawski |
| 6,599,250 B2 | 7/2003 | Webb et al. |
| 6,602,070 B2 | 8/2003 | Miller et al. |
| 6,604,527 B1 | 8/2003 | Palmisano |
| 6,606,744 B1 | 8/2003 | Mikurak |
| 6,607,382 B1 | 8/2003 | Kuo et al. |
| 6,611,783 B2 | 8/2003 | Kelly et al. |
| 6,611,867 B1 | 8/2003 | Bowman Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinbold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,682,346 B2 | 1/2004 | Chishti et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Yang et al. |
| 6,694,234 B2 | 2/2004 | Lockwood et al. |
| 6,697,164 B1 | 2/2004 | Babayoff et al. |
| 6,697,793 B2 | 2/2004 | McGreevy |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,736,638 B1 | 5/2004 | Sachdeva et al. |
| 6,739,869 B1 | 5/2004 | Taub et al. |
| 6,744,932 B1 | 6/2004 | Rubbert et al. |
| 6,749,414 B1 | 6/2004 | Hanson et al. |
| 6,769,913 B2 | 8/2004 | Hurson |
| 6,772,026 B2 | 8/2004 | Bradbury et al. |
| 6,790,036 B2 | 9/2004 | Graham |
| 6,802,713 B1 | 10/2004 | Chishti et al. |
| 6,814,574 B2 | 11/2004 | Abolfathi et al. |
| 6,830,450 B2 | 12/2004 | Knopp et al. |
| 6,832,912 B2 | 12/2004 | Mao |
| 6,832,914 B1 | 12/2004 | Bonnet et al. |
| 6,843,370 B2 | 1/2005 | Tuneberg |
| 6,845,175 B2 | 1/2005 | Kopelman et al. |
| 6,885,464 B1 | 4/2005 | Pfeiffer |
| 6,890,285 B2 | 5/2005 | Rahman et al. |
| 6,951,254 B2 | 10/2005 | Morrison |
| 6,976,841 B1 | 12/2005 | Osterwalder |
| 6,978,268 B2 | 12/2005 | Thomas et al. |
| 6,983,752 B2 | 1/2006 | Garabadian |
| 6,984,128 B2 | 1/2006 | Breining et al. |
| 6,988,893 B2 | 1/2006 | Haywood |
| 7,016,952 B2 | 3/2006 | Mullen et al. |
| 7,020,963 B2 | 4/2006 | Cleary et al. |
| 7,036,514 B2 | 5/2006 | Heck |
| 7,040,896 B2 | 5/2006 | Pavlovskaia et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,156,661 B2 | 1/2007 | Choi et al. |
| 7,166,063 B2 | 1/2007 | Rahman et al. |
| 7,184,150 B2 | 2/2007 | Quadling et al. |
| 7,191,451 B2 | 3/2007 | Nakagawa |
| 7,192,273 B2 | 3/2007 | McSurdy |
| 7,217,131 B2 | 5/2007 | Vuillemot |
| 7,220,122 B2 | 5/2007 | Chishti |
| 7,220,124 B2 | 5/2007 | Taub et al. |
| 7,229,282 B2 | 6/2007 | Andreiko et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,245,753 B2 | 7/2007 | Squilla et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,294,141 B2 | 11/2007 | Bergersen |
| 7,302,842 B2 | 12/2007 | Biester et al. |
| 7,320,592 B2 | 1/2008 | Chishti et al. |
| 7,328,706 B2 | 2/2008 | Barach et al. |
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,354,270 B2 | 4/2008 | Abolfathi et al. |
| 7,357,637 B2 | 4/2008 | Liechtung |
| 7,435,083 B2 | 10/2008 | Chishti et al. |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,543,511 B2 | 6/2009 | Kimura et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |

(56) References Cited

U.S. PATENT DOCUMENTS

| | | |
|---|---|---|
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,637,740 B2 | 12/2009 | Knopp |
| 7,641,473 B2 | 1/2010 | Sporbert et al. |
| 7,668,355 B2 | 2/2010 | Wong et al. |
| 7,670,179 B2 | 3/2010 | Muller |
| 7,695,327 B2 | 4/2010 | Bauerle et al. |
| 7,698,068 B2 | 4/2010 | Babayoff |
| 7,711,447 B2 | 5/2010 | Lu et al. |
| 7,724,378 B2 | 5/2010 | Babayoff |
| D618,619 S | 6/2010 | Walter |
| 7,728,848 B2 | 6/2010 | Petrov et al. |
| 7,731,508 B2 | 6/2010 | Borst |
| 7,735,217 B2 | 6/2010 | Borst |
| 7,740,476 B2 | 6/2010 | Rubbert et al. |
| 7,744,369 B2 | 6/2010 | Imgrund et al. |
| 7,746,339 B2 | 6/2010 | Matov et al. |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,841,464 B2 | 11/2010 | Cinader et al. |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,869,983 B2 | 1/2011 | Raby et al. |
| 7,872,760 B2 | 1/2011 | Ertl |
| 7,874,836 B2 | 1/2011 | McSurdy |
| 7,874,837 B2 | 1/2011 | Chishti et al. |
| 7,874,849 B2 | 1/2011 | Sticker et al. |
| 7,878,801 B2 | 2/2011 | Abolfathi et al. |
| 7,878,805 B2 | 2/2011 | Moss et al. |
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,929,151 B2 | 4/2011 | Liang et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,970,627 B2 | 6/2011 | Kuo et al. |
| 7,985,414 B2 | 7/2011 | Knaack et al. |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,029,277 B2 | 10/2011 | Lmgrund et al. |
| 8,038,444 B2 | 10/2011 | Kitching et al. |
| 8,045,772 B2 | 10/2011 | Kosuge et al. |
| 8,054,556 B2 | 11/2011 | Chen et al. |
| 8,070,490 B1 | 12/2011 | Roetzer et al. |
| 8,075,306 B2 | 12/2011 | Kitching et al. |
| 8,077,949 B2 | 12/2011 | Siang et al. |
| 8,083,556 B2 | 12/2011 | Stadler et al. |
| D652,799 S | 1/2012 | Mueller |
| 8,092,215 B2 | 1/2012 | Stone-Collonge et al. |
| 8,095,383 B2 | 1/2012 | Arnone et al. |
| 8,099,268 B2 | 1/2012 | Kitching et al. |
| 8,099,305 B2 | 1/2012 | Kuo et al. |
| 8,118,592 B2 | 2/2012 | Tortorici |
| 8,126,025 B2 | 2/2012 | Takeda |
| 8,136,529 B2 | 3/2012 | Kelly |
| 8,144,954 B2 | 3/2012 | Quadling et al. |
| 8,160,334 B2 | 4/2012 | Thiel et al. |
| 8,172,569 B2 | 5/2012 | Matty et al. |
| 8,197,252 B1 | 6/2012 | Harrison |
| 8,201,560 B2 | 6/2012 | Dembro |
| 8,215,312 B2 | 7/2012 | Garabadian et al. |
| 8,240,018 B2 | 8/2012 | Walter et al. |
| 8,275,180 B2 | 9/2012 | Kuo |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,401,826 B2 | 3/2013 | Cheng et al. |
| 8,419,428 B2 | 4/2013 | Lawrence |
| 8,433,083 B2 | 4/2013 | Abolfathi et al. |
| 8,439,672 B2 | 5/2013 | Matov et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,517,726 B2 | 8/2013 | Kakavand et al. |
| 8,520,922 B2 | 8/2013 | Wang et al. |
| 8,520,925 B2 | 8/2013 | Duret et al. |
| 8,523,565 B2 | 9/2013 | Matty et al. |
| 8,545,221 B2 | 10/2013 | Stone-Collonge et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,601,925 B1 | 12/2013 | Coto |
| 8,639,477 B2 | 1/2014 | Chelnokov et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,738,394 B2 | 5/2014 | Kuo |
| 8,743,923 B2 | 6/2014 | Geske et al. |
| 8,753,114 B2 | 6/2014 | Vuillemot |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,843,381 B2 | 9/2014 | Kuo et al. |
| 8,856,053 B2 | 10/2014 | Mah |
| 8,870,566 B2 | 10/2014 | Bergersen |
| 8,874,452 B2 | 10/2014 | Kuo |
| 8,878,905 B2 | 11/2014 | Fisker et al. |
| 8,899,976 B2 | 12/2014 | Chen et al. |
| 8,936,463 B2 | 1/2015 | Mason et al. |
| 8,944,812 B2 | 2/2015 | Kou |
| 8,948,482 B2 | 2/2015 | Levin |
| 8,956,058 B2 | 2/2015 | Rösch |
| 8,992,216 B2 | 3/2015 | Karazivan |
| 9,004,915 B2 | 4/2015 | Moss et al. |
| 9,022,792 B2 | 5/2015 | Sticker et al. |
| 9,039,418 B1 | 5/2015 | Rubbed |
| 9,084,535 B2 | 7/2015 | Girkin et al. |
| 9,084,657 B2 | 7/2015 | Matty et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,211,166 B2 | 12/2015 | Kuo et al. |
| 9,214,014 B2 | 12/2015 | Levin |
| 9,220,580 B2 | 12/2015 | Borovinskih et al. |
| 9,241,774 B2 | 1/2016 | Li et al. |
| 9,242,118 B2 | 1/2016 | Brawn |
| 9,261,358 B2 | 2/2016 | Atiya et al. |
| 9,277,972 B2 | 3/2016 | Brandt et al. |
| 9,336,336 B2 | 5/2016 | Deichmann et al. |
| 9,351,810 B2 | 5/2016 | Moon |
| 9,375,300 B2 | 6/2016 | Matov et al. |
| 9,403,238 B2 | 8/2016 | Culp |

(56) References Cited

U.S. PATENT DOCUMENTS

| | | |
|---|---|---|
| 9,408,743 B1 | 8/2016 | Wagner |
| 9,414,897 B2 | 8/2016 | Wu et al. |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,463,287 B1 | 10/2016 | Lorberbaum et al. |
| 9,492,243 B2 | 11/2016 | Kuo |
| 9,500,635 B2 | 11/2016 | Islam |
| 9,506,808 B2 | 11/2016 | Jeon et al. |
| 9,510,918 B2 | 12/2016 | Sanchez |
| 9,545,331 B2 | 1/2017 | Ingemarsson-Matzen |
| 9,566,132 B2 | 2/2017 | Stone-Collonge et al. |
| 9,584,771 B2 | 2/2017 | Mandelis et al. |
| 9,589,329 B2 | 3/2017 | Levin |
| 9,675,427 B2 | 6/2017 | Kopelman |
| 9,675,430 B2 | 6/2017 | Verker et al. |
| 9,693,839 B2 | 7/2017 | Atiya et al. |
| 9,730,769 B2 | 8/2017 | Chen et al. |
| 9,744,006 B2 | 8/2017 | Ross |
| 9,820,829 B2 | 11/2017 | Kuo |
| 9,830,688 B2 | 11/2017 | Levin |
| 9,844,421 B2 | 12/2017 | Moss et al. |
| 9,848,985 B2 | 12/2017 | Yang et al. |
| 9,861,451 B1 | 1/2018 | Davis |
| 9,936,186 B2 | 4/2018 | Jesenko et al. |
| 10,123,706 B2 | 11/2018 | Elbaz et al. |
| 10,123,853 B2 | 11/2018 | Moss et al. |
| 10,154,889 B2 | 12/2018 | Chen et al. |
| 10,159,541 B2 | 12/2018 | Bindayel |
| 10,172,693 B2 | 1/2019 | Brandt et al. |
| 10,195,690 B2 | 2/2019 | Culp |
| 10,231,801 B2 | 3/2019 | Korytov et al. |
| 10,238,472 B2 | 3/2019 | Levin |
| 10,258,432 B2 | 4/2019 | Webber |
| 2001/0002310 A1 | 5/2001 | Chishti et al. |
| 2001/0032100 A1 | 10/2001 | Mahmud et al. |
| 2001/0038705 A1 | 11/2001 | Rubbert et al. |
| 2001/0041320 A1 | 11/2001 | Phan et al. |
| 2002/0004727 A1 | 1/2002 | Knaus et al. |
| 2002/0007284 A1 | 1/2002 | Schurenberg et al. |
| 2002/0010568 A1 | 1/2002 | Rubbert et al. |
| 2002/0015934 A1 | 2/2002 | Rubbed et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0035572 A1 | 3/2002 | Takatori et al. |
| 2002/0064752 A1 | 5/2002 | Durbin et al. |
| 2002/0064759 A1 | 5/2002 | Durbin et al. |
| 2002/0087551 A1 | 7/2002 | Hickey et al. |
| 2002/0107853 A1 | 8/2002 | Hofmann et al. |
| 2002/0188478 A1 | 12/2002 | Breeland et al. |
| 2002/0192617 A1 | 12/2002 | Phan et al. |
| 2003/0000927 A1 | 1/2003 | Kanaya et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0049581 A1 | 3/2003 | Deluke |
| 2003/0057192 A1 | 3/2003 | Patel |
| 2003/0059736 A1 | 3/2003 | Lai et al. |
| 2003/0060532 A1 | 3/2003 | Subelka et al. |
| 2003/0068598 A1 | 4/2003 | Vallittu et al. |
| 2003/0095697 A1 | 5/2003 | Wood et al. |
| 2003/0101079 A1 | 5/2003 | McLaughlin |
| 2003/0103060 A1 | 6/2003 | Anderson et al. |
| 2003/0120517 A1 | 6/2003 | Eida et al. |
| 2003/0139834 A1 | 7/2003 | Nikolskiy et al. |
| 2003/0144886 A1 | 7/2003 | Taira |
| 2003/0172043 A1 | 9/2003 | Guyon et al. |
| 2003/0190575 A1 | 10/2003 | Hilliard |
| 2003/0192867 A1 | 10/2003 | Yamazaki et al. |
| 2003/0207224 A1 | 11/2003 | Lotte |
| 2003/0215764 A1 | 11/2003 | Kopelman et al. |
| 2003/0224311 A1 | 12/2003 | Cronauer |
| 2003/0224313 A1 | 12/2003 | Bergersen |
| 2003/0224314 A1 | 12/2003 | Bergersen |
| 2004/0002873 A1 | 1/2004 | Sachdeva |
| 2004/0009449 A1 | 1/2004 | Mah et al. |
| 2004/0013994 A1 | 1/2004 | Goldberg et al. |
| 2004/0019262 A1 | 1/2004 | Perelgut |
| 2004/0029078 A1 | 2/2004 | Marshall |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |
| 2004/0068199 A1 | 4/2004 | Echauz et al. |
| 2004/0078222 A1 | 4/2004 | Khan et al. |
| 2004/0080621 A1 | 4/2004 | Fisher et al. |
| 2004/0094165 A1 | 5/2004 | Cook |
| 2004/0107118 A1 | 6/2004 | Harnsberger et al. |
| 2004/0133083 A1 | 7/2004 | Comaniciu et al. |
| 2004/0152036 A1 | 8/2004 | Abolfathi |
| 2004/0158194 A1 | 8/2004 | Wolff et al. |
| 2004/0166463 A1 | 8/2004 | Wen et al. |
| 2004/0167646 A1 | 8/2004 | Jelonek et al. |
| 2004/0170941 A1 | 9/2004 | Phan et al. |
| 2004/0193036 A1 | 9/2004 | Zhou et al. |
| 2004/0197728 A1 | 10/2004 | Abolfathi et al. |
| 2004/0214128 A1 | 10/2004 | Sachdeva et al. |
| 2004/0219479 A1 | 11/2004 | Malin et al. |
| 2004/0220691 A1 | 11/2004 | Hofmeister et al. |
| 2004/0229185 A1 | 11/2004 | Knopp |
| 2004/0259049 A1 | 12/2004 | Kopelman et al. |
| 2005/0003318 A1 | 1/2005 | Choi et al. |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0038669 A1 | 2/2005 | Sachdeva et al. |
| 2005/0040551 A1 | 2/2005 | Biegler et al. |
| 2005/0042569 A1 | 2/2005 | Plan et al. |
| 2005/0042577 A1 | 2/2005 | Kvitrud et al. |
| 2005/0048433 A1 | 3/2005 | Hilliard |
| 2005/0074717 A1 | 4/2005 | Cleary et al. |
| 2005/0089822 A1 | 4/2005 | Geng |
| 2005/0100333 A1 | 5/2005 | Kerschbaumer et al. |
| 2005/0108052 A1 | 5/2005 | Omaboe |
| 2005/0131738 A1 | 6/2005 | Morris |
| 2005/0144150 A1 | 6/2005 | Ramamurthy et al. |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0186540 A1* | 8/2005 | Taub .......... A61C 9/0053 433/223 |
| 2005/0216314 A1 | 9/2005 | Secor |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0244791 A1 | 11/2005 | Davis et al. |
| 2005/0271996 A1 | 12/2005 | Sporbert et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0093982 A1 | 5/2006 | Wen |
| 2006/0098007 A1 | 5/2006 | Rouet et al. |
| 2006/0099545 A1 | 5/2006 | Lia et al. |
| 2006/0099546 A1 | 5/2006 | Bergersen |
| 2006/0110698 A1 | 5/2006 | Robson |
| 2006/0111631 A1 | 5/2006 | Kelliher et al. |
| 2006/0115785 A1 | 6/2006 | Li et al. |
| 2006/0137813 A1 | 6/2006 | Robrecht et al. |
| 2006/0147872 A1 | 7/2006 | Andreiko |
| 2006/0154198 A1 | 7/2006 | Durbin et al. |
| 2006/0154207 A1 | 7/2006 | Kuo |
| 2006/0173715 A1 | 8/2006 | Wang |
| 2006/0183082 A1 | 8/2006 | Quadling et al. |
| 2006/0188834 A1 | 8/2006 | Hilliard |
| 2006/0188848 A1 | 8/2006 | Tricca et al. |
| 2006/0194163 A1 | 8/2006 | Tricca et al. |
| 2006/0199153 A1 | 9/2006 | Liu et al. |
| 2006/0204078 A1 | 9/2006 | Orth et al. |

(56) References Cited

U.S. PATENT DOCUMENTS

| | | |
|---|---|---|
| 2006/0223022 A1 | 10/2006 | Solomon |
| 2006/0223023 A1 | 10/2006 | Lai et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1* | 11/2006 | De Dominicis ......... A61C 7/00 433/24 |
| 2006/0275729 A1 | 12/2006 | Fornoff |
| 2006/0275731 A1 | 12/2006 | Wen et al. |
| 2006/0275736 A1 | 12/2006 | Wen et al. |
| 2006/0277075 A1 | 12/2006 | Salwan |
| 2006/0290693 A1 | 12/2006 | Thou et al. |
| 2006/0292520 A1 | 12/2006 | Dillon et al. |
| 2007/0031775 A1 | 2/2007 | Andreiko |
| 2007/0046865 A1 | 3/2007 | Umeda et al. |
| 2007/0053048 A1 | 3/2007 | Kumar et al. |
| 2007/0054237 A1 | 3/2007 | Neuschafer |
| 2007/0065768 A1 | 3/2007 | Nadav |
| 2007/0087300 A1 | 4/2007 | Willison et al. |
| 2007/0087302 A1 | 4/2007 | Reising et al. |
| 2007/0106138 A1 | 5/2007 | Beiski et al. |
| 2007/0122592 A1 | 5/2007 | Anderson et al. |
| 2007/0128574 A1 | 6/2007 | Kuo et al. |
| 2007/0141525 A1 | 6/2007 | Cinader, Jr. |
| 2007/0141526 A1 | 6/2007 | Eisenberg et al. |
| 2007/0143135 A1 | 6/2007 | Lindquist et al. |
| 2007/0168152 A1 | 7/2007 | Matov et al. |
| 2007/0172112 A1 | 7/2007 | Paley et al. |
| 2007/0172291 A1 | 7/2007 | Yokoyama |
| 2007/0178420 A1 | 8/2007 | Keski-Nisula et al. |
| 2007/0183633 A1 | 8/2007 | Hoffmann |
| 2007/0184402 A1 | 8/2007 | Boutoussov et al. |
| 2007/0185732 A1 | 8/2007 | Hicks et al. |
| 2007/0192137 A1 | 8/2007 | Ombrellaro |
| 2007/0199929 A1 | 8/2007 | Rippl et al. |
| 2007/0215582 A1 | 9/2007 | Roeper et al. |
| 2007/0218422 A1 | 9/2007 | Ehrenfeld |
| 2007/0231765 A1 | 10/2007 | Phan et al. |
| 2007/0238065 A1 | 10/2007 | Sherwood et al. |
| 2007/0239488 A1 | 10/2007 | DeRosso |
| 2007/0263226 A1 | 11/2007 | Kurtz et al. |
| 2008/0013727 A1 | 1/2008 | Uemura |
| 2008/0020350 A1 | 1/2008 | Matov et al. |
| 2008/0045053 A1 | 2/2008 | Stadler et al. |
| 2008/0057461 A1 | 3/2008 | Cheng et al. |
| 2008/0057467 A1 | 3/2008 | Gittelson |
| 2008/0057479 A1 | 3/2008 | Grenness |
| 2008/0059238 A1 | 3/2008 | Park et al. |
| 2008/0090208 A1 | 4/2008 | Rubbed |
| 2008/0094389 A1 | 4/2008 | Rouet et al. |
| 2008/0113317 A1 | 5/2008 | Kemp et al. |
| 2008/0115791 A1 | 5/2008 | Heine |
| 2008/0118882 A1 | 5/2008 | Su |
| 2008/0118886 A1 | 5/2008 | Liang et al. |
| 2008/0141534 A1 | 6/2008 | Hilliard |
| 2008/0169122 A1 | 7/2008 | Shiraishi et al. |
| 2008/0171934 A1 | 7/2008 | Greenan et al. |
| 2008/0176448 A1 | 7/2008 | Muller et al. |
| 2008/0233530 A1 | 9/2008 | Cinader |
| 2008/0242144 A1 | 10/2008 | Dietz |
| 2008/0248443 A1 | 10/2008 | Chishti et al. |
| 2008/0254403 A1 | 10/2008 | Hilliard |
| 2008/0268400 A1 | 10/2008 | Moss et al. |
| 2008/0306724 A1 | 12/2008 | Kitching et al. |
| 2009/0029310 A1 | 1/2009 | Pumphrey et al. |
| 2009/0030290 A1 | 1/2009 | Kozuch et al. |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0087050 A1 | 4/2009 | Gandyra |
| 2009/0098502 A1 | 4/2009 | Andreiko |
| 2009/0099445 A1 | 4/2009 | Burger |
| 2009/0103579 A1 | 4/2009 | Ushimaru et al. |
| 2009/0105523 A1 | 4/2009 | Kassayan et al. |
| 2009/0130620 A1 | 5/2009 | Yazdi et al. |
| 2009/0136890 A1 | 5/2009 | Kang et al. |
| 2009/0136893 A1 | 5/2009 | Zegarelli |
| 2009/0148805 A1* | 6/2009 | Kois ..................... A61C 19/10 433/24 |
| 2009/0148809 A1 | 6/2009 | Kuo et al. |
| 2009/0170050 A1 | 7/2009 | Marcus |
| 2009/0181346 A1 | 7/2009 | Orth |
| 2009/0191502 A1 | 7/2009 | Cao et al. |
| 2009/0210032 A1 | 8/2009 | Beiski et al. |
| 2009/0218514 A1 | 9/2009 | Klunder et al. |
| 2009/0246726 A1 | 10/2009 | Chelnokov et al. |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0305540 A1 | 12/2009 | Stadler et al. |
| 2009/0316966 A1 | 12/2009 | Marshall et al. |
| 2009/0317757 A1 | 12/2009 | Lemchen |
| 2010/0015565 A1 | 1/2010 | Carrillo Gonzalez et al. |
| 2010/0019170 A1 | 1/2010 | Hart et al. |
| 2010/0028825 A1 | 2/2010 | Lemchen |
| 2010/0045902 A1 | 2/2010 | Ikeda et al. |
| 2010/0062394 A1 | 3/2010 | Jones et al. |
| 2010/0068676 A1 | 3/2010 | Mason et al. |
| 2010/0086890 A1 | 4/2010 | Kuo |
| 2010/0138025 A1 | 6/2010 | Morton et al. |
| 2010/0142789 A1 | 6/2010 | Chang et al. |
| 2010/0145664 A1 | 6/2010 | Hultgren et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1* | 7/2010 | Kuo ..................... A61C 7/08 433/24 |
| 2010/0179789 A1 | 7/2010 | Sachdeva et al. |
| 2010/0193482 A1 | 8/2010 | Ow et al. |
| 2010/0196837 A1 | 8/2010 | Farrell |
| 2010/0216085 A1 | 8/2010 | Kopelman |
| 2010/0217130 A1 | 8/2010 | Weinlaender |
| 2010/0231577 A1 | 9/2010 | Kim et al. |
| 2010/0268363 A1 | 10/2010 | Karim et al. |
| 2010/0268515 A1 | 10/2010 | Vogt et al. |
| 2010/0279243 A1 | 11/2010 | Cinader et al. |
| 2010/0280798 A1 | 11/2010 | Pattijn |
| 2010/0281370 A1 | 11/2010 | Rohaly et al. |
| 2010/0303316 A1 | 12/2010 | Bullis et al. |
| 2010/0312484 A1 | 12/2010 | DuHamel et al. |
| 2010/0327461 A1 | 12/2010 | Co et al. |
| 2011/0007920 A1 | 1/2011 | Abolfathi et al. |
| 2011/0012901 A1 | 1/2011 | Kaplanyan |
| 2011/0045428 A1 | 2/2011 | Boltunov et al. |
| 2011/0056350 A1 | 3/2011 | Gale et al. |
| 2011/0065060 A1 | 3/2011 | Teixeira et al. |
| 2011/0081625 A1 | 4/2011 | Fuh |
| 2011/0091832 A1* | 4/2011 | Kim ..................... A61C 7/146 433/3 |
| 2011/0102549 A1 | 5/2011 | Takahashi |
| 2011/0102566 A1 | 5/2011 | Zakian et al. |
| 2011/0104630 A1* | 5/2011 | Matov ................... A61C 7/002 433/24 |
| 2011/0136072 A1 | 6/2011 | Li et al. |
| 2011/0136090 A1 | 6/2011 | Kazemi |
| 2011/0143300 A1 | 6/2011 | Villaalba |
| 2011/0143673 A1 | 6/2011 | Landesman et al. |
| 2011/0159452 A1 | 6/2011 | Huang |
| 2011/0164810 A1 | 7/2011 | Zang et al. |
| 2011/0207072 A1 | 8/2011 | Schiemann |
| 2011/0212420 A1 | 9/2011 | Vuillemot |
| 2011/0220623 A1 | 9/2011 | Beutler |
| 2011/0235045 A1 | 9/2011 | Koerner et al. |
| 2011/0269092 A1 | 11/2011 | Kuo et al. |
| 2011/0316994 A1 | 12/2011 | Lemchen |
| 2012/0028210 A1 | 2/2012 | Hegyi et al. |
| 2012/0029883 A1 | 2/2012 | Heinz et al. |
| 2012/0040311 A1 | 2/2012 | Nilsson |
| 2012/0064477 A1 | 3/2012 | Schmitt |
| 2012/0081786 A1 | 4/2012 | Mizuyama et al. |
| 2012/0086681 A1 | 4/2012 | Kim et al. |
| 2012/0115107 A1 | 5/2012 | Adams |

(56) References Cited

U.S. PATENT DOCUMENTS

| | | |
|---|---|---|
| 2012/0129117 A1 | 5/2012 | McCance |
| 2012/0147912 A1 | 6/2012 | Moench et al. |
| 2012/0150494 A1 | 6/2012 | Anderson et al. |
| 2012/0166213 A1 | 6/2012 | Arnone et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0029284 A1 | 1/2013 | Teasdale |
| 2013/0081272 A1 | 4/2013 | Johnson et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0150689 A1 | 6/2013 | Shaw-Klein |
| 2013/0163627 A1 | 6/2013 | Seurin et al. |
| 2013/0201488 A1 | 8/2013 | Ishihara |
| 2013/0204599 A1 | 8/2013 | Matov et al. |
| 2013/0209952 A1 | 8/2013 | Kuo et al. |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0278396 A1 | 10/2013 | Kimmel |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2013/0325431 A1 | 12/2013 | See et al. |
| 2013/0337412 A1 | 12/2013 | Kwon |
| 2014/0061974 A1 | 3/2014 | Tyler |
| 2014/0081091 A1 | 3/2014 | Abolfathi et al. |
| 2014/0093160 A1 | 4/2014 | Porikli et al. |
| 2014/0106289 A1 | 4/2014 | Kozlowski |
| 2014/0122027 A1 | 5/2014 | Andreiko et al. |
| 2014/0136222 A1 | 5/2014 | Arnone et al. |
| 2014/0142902 A1 | 5/2014 | Chelnokov et al. |
| 2014/0178829 A1 | 6/2014 | Kim |
| 2014/0265034 A1 | 9/2014 | Dudley |
| 2014/0272774 A1 | 9/2014 | Dillon et al. |
| 2014/0280376 A1 | 9/2014 | Kuo |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0342301 A1 | 11/2014 | Fleer et al. |
| 2014/0350354 A1 | 11/2014 | Stenzler et al. |
| 2014/0363778 A1 | 12/2014 | Parker |
| 2015/0002649 A1 | 1/2015 | Nowak et al. |
| 2015/0004553 A1 | 1/2015 | Li et al. |
| 2015/0021210 A1 | 1/2015 | Kesling |
| 2015/0079531 A1 | 3/2015 | Heine |
| 2015/0094564 A1 | 4/2015 | Tashman et al. |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0132708 A1 | 5/2015 | Kuo |
| 2015/0140502 A1 | 5/2015 | Brawn et al. |
| 2015/0142400 A1* | 5/2015 | Matov .................... G06F 30/20 703/6 |
| 2015/0150501 A1 | 6/2015 | George et al. |
| 2015/0164335 A1 | 6/2015 | Van Der Poel et al. |
| 2015/0173856 A1 | 6/2015 | Lowe et al. |
| 2015/0182303 A1 | 7/2015 | Abraham et al. |
| 2015/0216626 A1 | 8/2015 | Ranjbar |
| 2015/0216716 A1 | 8/2015 | Anitua Aldecoa |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0320532 A1 | 11/2015 | Matty et al. |
| 2015/0325044 A1 | 11/2015 | Lebovitz |
| 2015/0338209 A1 | 11/2015 | Knottel |
| 2015/0351638 A1 | 12/2015 | Amato |
| 2015/0374469 A1 | 12/2015 | Konno et al. |
| 2016/0000332 A1 | 1/2016 | Atiya et al. |
| 2016/0003610 A1 | 1/2016 | Lampert et al. |
| 2016/0022185 A1 | 1/2016 | Agarwal et al. |
| 2016/0042509 A1 | 2/2016 | Andreiko et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0095668 A1 | 4/2016 | Kuo et al. |
| 2016/0100924 A1 | 4/2016 | Wilson et al. |
| 2016/0106520 A1 | 4/2016 | Borovinskih et al. |
| 2016/0120621 A1 | 5/2016 | Li et al. |
| 2016/0128624 A1* | 5/2016 | Matt .................... A61B 5/4542 600/301 |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0220105 A1 | 8/2016 | Durent |
| 2016/0220200 A1 | 8/2016 | Sandholm et al. |
| 2016/0225151 A1 | 8/2016 | Cocco et al. |
| 2016/0228213 A1 | 8/2016 | Tod et al. |
| 2016/0242871 A1 | 8/2016 | Morton et al. |
| 2016/0246936 A1 | 8/2016 | Kahn |
| 2016/0287358 A1 | 10/2016 | Nowak et al. |
| 2016/0296303 A1 | 10/2016 | Parker |
| 2016/0302885 A1 | 10/2016 | Matov et al. |
| 2016/0328843 A1 | 11/2016 | Graham et al. |
| 2016/0338799 A1 | 11/2016 | Wu et al. |
| 2016/0346063 A1 | 12/2016 | Schulhof et al. |
| 2016/0367188 A1 | 12/2016 | Malik et al. |
| 2016/0367339 A1 | 12/2016 | Khardekar et al. |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0049311 A1 | 2/2017 | Borovinskih et al. |
| 2017/0049326 A1 | 2/2017 | Alfano et al. |
| 2017/0056131 A1 | 3/2017 | Alauddin et al. |
| 2017/0065379 A1* | 3/2017 | Cowburn ............ G06K 9/00228 |
| 2017/0071705 A1 | 3/2017 | Kuo |
| 2017/0086943 A1 | 3/2017 | Mah |
| 2017/0100209 A1 | 4/2017 | Wen |
| 2017/0100212 A1 | 4/2017 | Sherwood et al. |
| 2017/0100213 A1 | 4/2017 | Kuo |
| 2017/0100214 A1 | 4/2017 | Wen |
| 2017/0105815 A1 | 4/2017 | Matov et al. |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0215739 A1 | 8/2017 | Miyasato |
| 2017/0251954 A1 | 9/2017 | Lotan et al. |
| 2017/0258555 A1 | 9/2017 | Kopelman |
| 2017/0265970 A1 | 9/2017 | Verker |
| 2017/0319054 A1 | 11/2017 | Miller et al. |
| 2017/0319296 A1 | 11/2017 | Webber et al. |
| 2017/0325690 A1 | 11/2017 | Salah et al. |
| 2017/0340411 A1 | 11/2017 | Akselrod |
| 2017/0340415 A1 | 11/2017 | Choi et al. |
| 2018/0000563 A1 | 1/2018 | Shanjani et al. |
| 2018/0000565 A1 | 1/2018 | Shanjani et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0071054 A1 | 3/2018 | Ha |
| 2018/0071055 A1 | 3/2018 | Kuo |
| 2018/0085059 A1 | 3/2018 | Lee |
| 2018/0096465 A1 | 4/2018 | Levin |
| 2018/0110590 A1* | 4/2018 | Maraj ................ A61C 13/0004 |
| 2018/0125610 A1 | 5/2018 | Carrier et al. |
| 2018/0153648 A1 | 6/2018 | Shanjani et al. |
| 2018/0153649 A1 | 6/2018 | Wu et al. |
| 2018/0153733 A1 | 6/2018 | Kuo |
| 2018/0168788 A1 | 6/2018 | Fernie |
| 2018/0192877 A1 | 7/2018 | Atiya et al. |

(56) References Cited

U.S. PATENT DOCUMENTS

| | | |
|---|---|---|
| 2018/0228359 A1 | 8/2018 | Meyer et al. |
| 2018/0280118 A1 | 10/2018 | Cramer |
| 2018/0284727 A1 | 10/2018 | Cramer et al. |
| 2018/0318043 A1 | 11/2018 | Li et al. |
| 2018/0353264 A1 | 12/2018 | Riley et al. |
| 2018/0360567 A1 | 12/2018 | Xue et al. |
| 2018/0368944 A1 | 12/2018 | Sato et al. |
| 2018/0368961 A1 | 12/2018 | Shanjani et al. |
| 2019/0026599 A1 | 1/2019 | Salah et al. |
| 2019/0046296 A1 | 2/2019 | Kopelman et al. |
| 2019/0046297 A1 | 2/2019 | Kopelman et al. |
| 2019/0069975 A1 | 3/2019 | Cam et al. |
| 2019/0076216 A1 | 3/2019 | Moss et al. |
| 2019/0090983 A1 | 3/2019 | Webber et al. |
| 2020/0005676 A1* | 1/2020 | Kubota ............... G09B 23/283 |

FOREIGN PATENT DOCUMENTS

| | | |
|---|---|---|
| AU | 5598894 A | 6/1994 |
| CA | 1121955 A1 | 4/1982 |
| CN | 1655732 A | 8/2005 |
| CN | 1655733 A | 8/2005 |
| CN | 102017658 A | 4/2011 |
| CN | 103889364 A | 6/2014 |
| CN | 204092220 U | 1/2015 |
| CN | 105496575 A | 4/2016 |
| CN | 105997274 A | 10/2016 |
| DE | 2749802 A1 | 5/1978 |
| DE | 3526198 A1 | 2/1986 |
| DE | 4207169 A1 | 9/1993 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 202012011899 U1 | 1/2013 |
| DE | 102014225457 A1 | 6/2016 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2867377 A1 | 9/2005 |
| FR | 2930334 A1 | 10/2009 |
| GB | 1550777 A | 8/1979 |
| JP | 53-058191 A | 5/1978 |
| JP | 4028359 A | 1/1992 |
| JP | 08-508174 A | 9/1996 |
| JP | 09-19443 A | 1/1997 |
| JP | 2003245289 A | 9/2003 |
| JP | 2000339468 A | 9/2004 |
| JP | 2005527320 A | 9/2005 |
| JP | 2005527321 A | 9/2005 |
| JP | 2006043121 A | 2/2006 |
| JP | 2007151614 A | 6/2007 |
| JP | 2007260158 A | 10/2007 |
| JP | 2007537824 A | 12/2007 |
| JP | 2008067732 A | 3/2008 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009078133 A | 4/2009 |
| JP | 2009101386 A | 5/2009 |
| JP | 2009205330 A | 9/2009 |
| JP | 2010017726 A | 1/2010 |
| JP | 2011087733 A | 5/2011 |
| JP | 2012045143 A | 3/2012 |
| JP | 2013007645 A | 1/2013 |
| JP | 2013192865 A | 9/2013 |
| JP | 201735173 A | 2/2017 |
| KR | 10-20020062793 A | 7/2002 |
| KR | 10-20070108019 A | 11/2007 |
| KR | 10-20090065778 A | 6/2009 |
| KR | 10-1266966 B1 | 5/2013 |
| KR | 10-2016-041632 A | 4/2016 |
| KR | 10-2016-0071127 A | 6/2016 |
| KR | 10-1675089 B1 | 11/2016 |
| TW | 480166 B | 3/2002 |
| WO | WO91/004713 A1 | 4/1991 |
| WO | WO92/03102 A1 | 3/1992 |
| WO | WO94/010935 A1 | 5/1994 |
| WO | WO96/23452 A1 | 8/1996 |
| WO | WO98/032394 A1 | 7/1998 |
| WO | WO98/044865 A1 | 10/1998 |
| WO | WO01/08592 A1 | 2/2001 |
| WO | WO01/85047 A2 | 11/2001 |
| WO | WO02/017776 A2 | 3/2002 |
| WO | WO02/062252 A1 | 8/2002 |
| WO | WO02/095475 A1 | 11/2002 |
| WO | WO03/003932 A2 | 1/2003 |
| WO | WO2006/096558 A2 | 9/2006 |
| WO | WO2006/100700 A1 | 9/2006 |
| WO | WO2006/133548 A1 | 12/2006 |
| WO | WO2007/019709 A2 | 2/2007 |
| WO | WO2007/071341 A1 | 6/2007 |
| WO | WO2007/103377 A2 | 9/2007 |
| WO | WO2008/115654 A1 | 9/2008 |
| WO | WO2009/016645 A2 | 2/2009 |
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/059988 A1 | 5/2010 |
| WO | WO2010/123892 A2 | 10/2010 |
| WO | WO2012/007003 A1 | 1/2012 |
| WO | WO2012/064684 A2 | 5/2012 |
| WO | WO2012/074304 A2 | 6/2012 |
| WO | WO2012/078980 A2 | 6/2012 |
| WO | WO2012/083968 A1 | 6/2012 |
| WO | WO2012/140021 A2 | 10/2012 |
| WO | WO2013/058879 A2 | 4/2013 |
| WO | WO2014/068107 A1 | 5/2014 |
| WO | WO2014/091865 A1 | 6/2014 |
| WO | WO2014/143911 A1 | 9/2014 |
| WO | WO2015/015289 A2 | 2/2015 |
| WO | WO2015/063032 A1 | 5/2015 |
| WO | WO2015/112638 A1 | 7/2015 |
| WO | WO2015/176004 A1 | 11/2015 |
| WO | WO2016/004415 A1 | 1/2016 |
| WO | WO2016/042393 A1 | 3/2016 |
| WO | WO2016/061279 A1 | 4/2016 |
| WO | WO2016/084066 A1 | 6/2016 |
| WO | WO2016/099471 A1 | 6/2016 |
| WO | WO2016/113745 A1 | 7/2016 |
| WO | WO2016/116874 A1 | 7/2016 |
| WO | WO2016/200177 A1 | 12/2016 |
| WO | WO2017/006176 A1 | 1/2017 |
| WO | WO2017/182654 A1 | 10/2017 |
| WO | WO2018/057547 A1 | 3/2018 |
| WO | WO2018/085718 A2 | 5/2018 |
| WO | WO2018/232113 A1 | 12/2018 |
| WO | WO2019/018784 A1 | 1/2019 |

OTHER PUBLICATIONS

Beautyworlds.com; Virtual plastic surgery—beautysurge.com announces launch of cosmetic surgery digital imaging services; 5 pages; retrieved from the internet (http://www.beautyworlds.com/cosmossurgdigitalimagning.htm); Mar. 2004.

Berland; The use of smile libraries for cosmetic dentistry; Dental Tribunne: Asia pacfic Edition; pp. 16-18; Mar. 29, 2006.

(56) References Cited

OTHER PUBLICATIONS

Bookstein; Principal warps: Thin-plate splines and decomposition of deformations; IEEE Transactions on pattern analysis and machine intelligence; 11(6); pp. 567-585; Jun. 1989.
Cadent Inc.; OrthoCAD ABO user guide; 38 pages; Dec. 21, 2005.
Cadent Inc.; Reviewing and modifying an orthoCAD case; 4 pages; Feb. 14, 2005.
Daniels et al.; The development of the index of complexity outcome and need (ICON); British Journal of Orthodontics; 27(2); pp. 149-162; Jun. 2000.
Dentrix; Dentrix G3, new features; 2 pages; retrieved from the internet (http://www.dentrix.com/g3/new_features/index.asp); on Jun. 6, 2008.
Di Giacomo et al.; Clinical application of sterolithographic surgical guides for implant placement: Preliminary results; Journal Periodontolgy; 76(4); pp. 503-507; Apr. 2005.
Gansky; Dental data mining: potential pitfalls and practical issues; Advances in Dental Research; 17(1); pp. 109-114; Dec. 2003.
Geomagic; Dental reconstruction; 1 page; retrieved from the internet (http://geomagic.com/en/solutions/industry/detal_desc.php) on Jun. 6, 2008.
Gottschalk et al.; OBBTree: A hierarchical structure for rapid interference detection; 12 pages; (http://www.cs.unc.edu/?geom/OBB/OBBT.html); retieved from to internet (https://wwww.cse.iitk.ac.in/users/amit/courses/RMP/presentations/dslamba/presentation/sig96.pdf) on Apr. 25, 2019.
Gpsdentaire.com; Get a realistic smile simulation in 4 steps with GPS; a smile management software; 10 pages; retrieved from the internet (http://www.gpsdentaire.com/en/preview/) on Jun. 6, 2008.
Karaman et al.; A practical method of fabricating a lingual retainer; Am. Journal of Orthodontic and Dentofacial Orthopedics; 124(3); pp. 327-330; Sep. 2003.
Mantzikos et al.; Case report: Forced eruption and implant site development; The Angle Orthodontist; 68(2); pp. 179-186; Apr. 1998.
Methot; Get the picture with a gps for smile design in 3 steps; Spectrum; 5(4); pp. 100-105; (year of pub. sufficiently earlier than effective US filing date and any foreign priority date) 2006.
OrthoCAD downloads; retrieved Jun. 27, 2012 from the internet (www.orthocad.com/download/downloads.asp); 2 pages; Feb. 14, 2005.
Page et al.; Validity and accuracy of a risk calculator in predicting periodontal disease; Journal of the American Dental Association; 133(5); pp. 569-576; May 2002.
Patterson Dental; Cosmetic imaging; 2 pages retrieved from the internet (http://patterson.eaglesoft.net/cnt_di_cosimg.html) on Jun. 6, 2008.
Rose et al.; The role of orthodontics in implant dentistry; British Dental Journal; 201(12); pp. 753-764; Dec. 23, 2006.
Rubin et al.; Stress analysis of the human tooth using a three-dimensional finite element model; Journal of Dental Research; 62(2); pp. 82-86; Feb. 1983.
Sarment et al.; Accuracy of implant placement with a sterolithographic surgical guide; journal of Oral and Maxillofacial Implants; 118(4); pp. 571-577; Jul. 2003.
Smalley; Implants for tooth movement: Determining implant location and orientation: Journal of Esthetic and Restorative Dentistry; 7(2); pp. 62-72; Mar. 1995.
Smart Technology; Smile library II; 1 page; retrieved from the internet (http://smart-technology.net/) on Jun. 6, 2008.
Smile-Vision_The smile-vision cosmetic imaging system; 2 pages; retrieved from the internet (http://www.smile-vision.net/cos_imaging.php) on Jun. 6, 2008.
Szeliski; Introduction to computer vision: Structure from motion; 64 pages; retrieved from the internet (http://robots.stanford.edu/cs223b05/notes/CS%20223-B%20L10%structurefrommotion1b.ppt, on Feb. 3, 2005.
Vevin et al.; Pose estimation of teeth through crown-shape matching; in Medical Imaging: Image Processing of International Society of Optics and Photonics; vol. 4684; pp. 955-965; May 9, 2002.
Virtual Orthodontics; Our innovative software; 2 pages; (http://www.virtualorthodontics.com/innovativesoftware.html); retrieved from the internet (https://web.archive.org/web/20070518085145/http://www.virtualorthodontics.com/innovativesoftware.html); (year of pub. sufficiently earlier than effective US filing date and any foreign priority date) 2005.
Wiedmann; According to the laws of harmony to find the right tooth shape with assistance of the computer; Digital Dental News; 2nd Vol.; pp. 0005-0008; (English Version Included); Apr. 2008.
Wong et al.; Computer-aided design/computer-aided manufacturing surgical guidance for placement of dental implants: Case report; Implant Dentistry; 16(2); pp. 123-130; Sep. 2007.
Wong et al.; The uses of orthodontic study models in diagnosis and treatment planning; Hong Knog Dental Journal; 3(2); pp. 107-115; Dec. 2006.
Yaltara Software; Visual planner; 1 page; retrieved from the internet (http://yaltara.com/vp/) on Jun. 6, 2008.
Zhang et al.; Visual speech features extraction for improved speech recognition; 2002 IEEE International conference on Acoustics, Speech and Signal Processing; vol. 2; 4 pages; May 13-17, 2002.
Arnone et al.; U.S. Appl. No. 16/235,449 entitled "Method and system for providing indexing and cataloguing of orthodontic related treatment profiles and options," filed Dec. 28, 2018.
Mason et al.; U.S. Appl. No. 16/374,648 entitled "Dental condition evaluation and treatment," filed Apr. 3, 2019.
Brandt et al.; U.S. Appl. No. 16/235,490 entitled "Dental wire attachment," filed Dec. 28, 2018.
Kou; U.S. Appl. No. 16/270,891 entitled "Personal data file," filed Feb. 8, 2019.
Bernabe et al.; Are the lower incisors the best predictors for the unerupted canine and premolars sums? An analysis of peruvian sample; The Angle Orthodontist; 75(2); pp. 202-207; Mar. 2005.
Collins English Dictionary; Teeth (definition); 9 pages; retrieved from the internet (https:www.collinsdictionary.com/us/dictionary/english/teeth) on May 13, 2019.
Dental Monitoring; Basics: How to put the cheek retractor?; 1 page (Screenshot); retrieved from the interenet (https://www.youtube.com/watch?v=6K1HXw4Kq3c); May 27, 2016.
Dental Monitoring; Dental monitoring tutorial; 1 page (Screenshot); retrieved from the internet (https:www.youtube.com/watch?v=Dbe3udOf9_c); Mar. 18, 2015.
Dictionary.com; Plural (definition); 6 pages; retrieved from the internet ( https://www.dictionary.com/browse/plural#) on May 13, 2019.
Dictionary.com; Quadrant (definition); 6 pages; retrieved from the internet ( https://www.dictionary.com/browse/quadrant?s=t) on May 13, 2019.
Ecligner Selfie; Change your smile; 1 page (screenshot); retrieved from the internet (https:play.google.com/store/apps/details?id=parklict.ecligner); on Feb. 13, 2018.
Martinelli et al.; Prediction of lower permanent canine and premolars width by correlation methods; The Angle Orthodontist; 75(5); pp. 805-808; Sep. 2005.
Nourallah et al.; New regression equations for prediciting the size of unerupted canines and premolars in a contemporary population; The Angle Orthodontist; 72(3); pp. 216-221; Jun. 2002.
Paredes et al.; A new, accurate and fast digital method to predict unerupted tooth size; The Angle Orthodontist; 76(1); pp. 14-19; Jan. 2006.
Sobral De Agular et al.; The gingival crevicular fluid as a source of biomarkers to enhance efficiency of orthodontic and functional treatment of growing patients; Bio. Med. Research International; vol. 2017; pp. 1-7; Article ID 3257235; (year of pub. sufficiently earlier than effective US filing date and any foreign priority date) 2017.
Levin; U.S. Appl. No. 16/282,431 entitled "Estimating a surface texture of a tooth," filed Feb. 2, 2019.
Chen et al.; U.S. Appl. No. 16/223,019 entitled "Release agent receptacle," filed Dec. 17, 2018.
Farooq et al.; Relationship between tooth dimensions and malocclusion; JPMA: The Journal of the Pakistan Medical Association; 64(6); pp. 670-674; Jun. 2014.

(56) References Cited

OTHER PUBLICATIONS

Newcombe; DTAM: Dense tracking and mapping in real-time; 8 pages; retrieved from the internet (http://www.doc.ic.ac.uk/?ajd/Publications/newcombe_etal_iccv2011.pdf; on Dec. 2011.
Ormco.com; Increasing clinical performance with 3D interactive treatment planning and patient-specific appliances; 8 pages; retrieved from the Internet (http://www.konsident.com/wp-content/files_mf/1295385693http_ormco.com_index_cmsfilesystemaction_fileOrmcoPDF_whitepapers.pdf) on Feb. 27, 2019.
Video of DICOM to Surgical Guides; [Copy Not Enclosed], Can be viewed at <URL:https://youtu.be/47KtOmCEFQk; Published Apr. 4, 2016.
Sabina et al., U.S. Appl. No. 16/258,516 entitled "Diagnostic intraoral scanning" filed Jan. 25, 2019.
Sabina et al., U.S. Appl. No. 16/258,523 entitled "Diagnostic intraoral tracking" filed Jan. 25, 2019.
Sabina et al., U.S. Appl. No. 16/258,527 entitled "Diagnostic intraoral methods and apparatuses" filed Jan. 25, 2019.
Li et al.; U.S. Appl. No. 16/171,159 entitled "Alternative bite adjustment structures," filed Oct. 25, 2018.
Culp; U.S. Appl. No. 16/236,220 entitled "Laser cutting," filed Dec. 28, 2018.
Culp; U.S. Appl. No. 16/265,287 entitled "Laser cutting," filed Feb. 1, 2019.
AADR. American Association for Dental Research; Summary of Activities; Los Angeles, CA; p. 195; Mar. 20-23,(year of pub. sufficiently earlier than effective US filing date and any foreign priority date) 1980.
Alcaniz et aL; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.
Alexander et al.; The DigiGraph Work Station Part 2 Clinical Management; J. Clin. Orthod.; pp. 402-407; (Author Manuscript); Jul. 1990.
Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.
Allesee Orthodontic Appliance: Important Tip About Wearing the Red White & Blue Active Clear Retainer System; Allesee Orthodontic Appliances-Pro Lab; 1 page; (year of pub. sufficiently earlier than effective US filing date and any foreign priority date); 1998.
Allesee Orthodontic Appliances: DuraClearTM; Product information; 1 page; (year of pub. sufficiently earlier than effective US filing date and any foreign priority date) 1997.
Allesee Orthodontic Appliances; The Choice Is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.
Allesee Orthodontic Appliances; The Choice Is Clear: Red, White & Blue . . . The Simple, Affordable, No-Braces Treatment; (product information), 6 pages; (year of pub. sufficiently earlier than effective US filing date and any foreign priority date) 2003.
Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.
Allesee Orthodontic Appliances; The Red, White & Blue Way to Improve Your Smile; (information for patients), 2 pages; (year of pub. sufficiently earlier than effective US filing date and any foreign priority date) 1992.
Allesee Orthodontic Appliances; You may be a candidate for this invisible no-braces treatment; product information for patients; 2 pages; (year of pub. sufficiently earlier than effective US filing date and any foreign priority date) 2002.
Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.
Altschuler et al.; Laser Electro-Optic System for Rapid Three-Dimensional (3D) Topographic Mapping of Surfaces; Optical Engineering; 20(6); pp. 953-961; Dec. 1981.
Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.
Altschuler; 3D Mapping of Maxillo-Facial Prosthesis; AADR Abstract #607; 2 pages total, (year of pub. sufficiently earlier than effective US filing date and any foreign priority date) 1980.
Alves et al.; New trends in food allergens detection: toward biosensing strategies; Critical Reviews in Food Science and Nutrition; 56(14); pp. 2304-2319; doi: 10.1080/10408398.2013.831026; Oct. 2016.
Andersson et al.; Clinical Results with Titanium Crowns Fabricated with Machine Duplication and Spark Erosion; Acta Odontologica Scandinavica; 47(5); pp. 279-286; Oct. 1989.
Andrews, The Six Keys to Optimal Occlusion Straight Wire, Chapter 3, L.A. Wells; pp. 13-24; (year of pub. sufficiently earlier than effective US filing date and any foreign priority date) 1989.
Arakawa et al; Mouthguard biosensor with telemetry system for monitoring of saliva glucose: A novel cavitas sensor; Biosensors and Bioelectronics; 84; pp. 106-111; Oct. 2016.
Bandodkar et al.; All-printed magnetically self-healing electrochemical devices; Science Advances; 2(11); 11 pages; e1601465; Nov. 2016.
Bandodkar et al.; Self-healing inks for autonomous repair of printable electrochemical devices; Advanced Electronic Materials; 1(12); 5 pages; 1500289; Dec. 2015.
Bandodkar et al.; Wearable biofuel cells: a review; Electroanalysis; 28(6); pp. 1188-1200; Jun. 2016.
Bandodkar et al.; Wearable chemical sensors: present challenges and future prospects; Acs Sensors; 1(5); pp. 464-482; May 11, 2016.
Barone et al.; Creation of 3D multi-body orthodontic models by using independent imaging sensors; Sensors; 13(2); pp. 2033-2050; Feb. 5, 2013.
Bartels et al.; An Introduction to Splines for Use in Computer Graphics and Geometric Modeling; Morgan Kaufmann Publishers; pp. 422-425 Jan. 1, 1987.
Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.
Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
Begole et al.; A Computer System for the Analysis of Dental Casts; The Angle Orthodontist; 51(3); pp. 252-258; Jul. 1981.
Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.
Bhatia et al.; A Computer-Aided Design for Orthognathic Surgery; British Journal of Oral and Maxillofacial Surgery; 22(4); pp. 237-253; Aug. 1, 1984.

(56) References Cited

OTHER PUBLICATIONS

Biggerstaff et al.; Computerized Analysis of Occlusion in the Postcanine Dentition; American Journal of Orthodontics; 61(3); pp. 245-254; Mar. 1972.
Biggerstaff; Computerized Diagnostic Setups and Simulations; Angle Orthodontist; 40(1); pp. 28-36; Jan. 1970.
Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.
Blu et al.; Linear interpolation revitalized; IEEE Transactions on Image Processing; 13(5); pp. 710-719; May 2004.
Bourke, Coordinate System Transformation; 1 page; retrived from the internet (http://astronomy.swin.edu.au/' pbourke/prolection/coords) on Nov. 5, 2004; Jun. 1996.
Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on the Uses of the Computer in Orthodontic Practice (Part 1); Journal of Clinical Orthodontics; 13(7); pp. 442-453; (interview); Jul. 1979.
Burstone; Dr. Charles J. Burstone on the Uses of the Computer in Orthodontic Practice (Part 2); journal of Clinical Orthodontics; 13(8); pp. 539-551 (interview); Aug. 1979.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
CSI Computerized Scanning and Imaging Facility; What is a maximum/minimum intensity projection (Mip/MinIP); 1 page; retrived from the internet (http://csi.whoi.edu/content/what-maximumminimum-intensity-projection-mipminip); Jan. 4, 2010.
Cottingham; Gnathologic Clear Plastic Positioner; American Journal of Orthodontics; 55(1); pp. 23-31; Jan. 1969.
Crawford; CAD/CAM in the Dental Office: Does It Work?; Canadian Dental Journal; 57(2); pp. 121-123 Feb. 1991.
Crawford; Computers in Dentistry: Part 1: CAD/CAM: The Computer Moves Chairside, Part 2: F. Duret ' A Man With a Vision, Part 3: The Computer Gives New Vision—Literally, Part 4: Bytes 'N Bites the Computer Moves From the Front Desk to the Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
Cureton; Correcting Malaligned Mandibular Incisors with Removable Retainers; Journal of Clinical Orthodontics; 30(7); pp. 390-395; Jul. 1996.

Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
DCS Dental AG; The CAD/CAM 'DCS Titan System' for Production of Crowns/Bridges; DSC Production; pp. 1-7; Jan. 1992.
Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the Cerec-Method; 2 pages; May 1991.
Dentrac Corporation; Dentrac document; pp. 4-13; (year of pub. sufficiently earlier than effective US filing date and any foreign priority date) 1992.
Dent-X; Dentsim . . . Dent-x's virtual reality 3-D training simulator . . . A revolution in dental education; 6 pages; retrieved from the internet (http://www.dent-x.com/DentSim.htm); on Sep. 24, 1998.
Di Muzio et al.; Minimum intensity projection (MinIP); 6 pages; retrieved from the internet (https://radiopaedia.org/articles/minimum-intensity-projection-minip) on Sep. 6, 2018.
Doruk et al.; The role of the headgear timer in extraoral co-operation; European Journal of Orthodontics; 26; pp. 289-291; Jun. 1, 2004.
Doyle; Digital Dentistry; Computer Graphics World; pp. 50-52 andp. 54; Oct. 2000.
Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.
Duret et al.; CAD/CAM Imaging in Dentistry; Current Opinion in Dentistry; 1 (2); pp. 150-154; Apr. 1991.
Duret et al; CAD-CAM in Dentistry; Journal of the American Dental Association; 117(6); pp. 715-720; Nov. 1988.
Duret; The Dental CAD/CAM, General Description of the Project; Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Economides; The Microcomputer in the Orthodontic Office; Journal of Clinical Orthodontics; 13(11); pp. 767-772; Nov. 1979.
Ellias et al.; Proteomic analysis of saliva identifies potential biomarkers for orthodontic tooth movement; The Scientific World Journal; vol. 2012; Article ID 647240; dio:10.1100/2012/647240; 7 pages; (year of pub. sufficiently earlier than effective US filing date and any foreign priority date) 2012.
Elsasser; Some Observations on the History and Uses of the Kesling Positioner; American Journal of Orthodontics; 36(5); pp. 368-374; May 1, 1950.
English translation of Japanese Laid-Open Publication No. 63-11148 to inventor T. Ozukuri (Laid-Open on Jan. 18, 1998) pp. 1-7.
Faber et al.; Computerized Interactive Orthodontic Treatment Planning; American Journal of Orthodontics; 73(1); pp. 36-46; Jan. 1978.
Felton et al.; A Computerized Analysis of the Shape and Stability of Mandibular Arch Form; American Journal of Orthodontics and Dentofacial Orthopedics; 92(6); pp. 478-483; Dec. 1987.
Florez-Moreno; Time-related changes in salivary levels of the osteotropic factors sRANKL and OPG through orthodontic tooth movement; American Journal of Orthodontics and Dentofacial Orthopedics; 143(1); pp. 92-100; Jan. 2013.
Friede et al.; Accuracy of Cephalometric Prediction in Orthognathic Surgery; Journal of Oral and Maxillofacial Surgery; 45(9); pp. 754-760; Sep. 1987.
Friedrich et al; Measuring system for in vivo recording of force systems in orthodontic treatment-concept and analysis of accuracy; J. Biomech.; 32(1); pp. 81-85; (Abstract Only) Jan. 1999.
Futterling et al.; Automated Finite Element Modeling of a Human Mandible with Dental Implants; JS WSCG '98—Conference Program; 8 pages; retrieved from the Internet (https://dspace5.zcu.cz/bitstream/11025/15851/1/Strasser_98.pdf); on Aug. 21, 2018.

(56) References Cited

OTHER PUBLICATIONS

Gao et al.; 3-D element Generation for Multi-Connected Complex Dental and Mandibular Structure; IEEE Proceedings International Workshop in Medical Imaging and Augmented Reality; pp. 267-271; Jun. 12, 2001.

Gim-Alldent Deutschland, "Das DUX System: Die Technik," 3 pages; (English Translation Included); (year of pub. sufficiently earlier than effective US filing date and any foreign priority date); 2002.

Gottlieb et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.

Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13,1990.

Grest, Daniel; Marker-Free Human Motion Capture in Dynamic Cluttered Environments from a Single View-Point, PhD Thesis; 171 pages; Dec. 2007.

Guess et al.; Computer Treatment Estimates in Orthodontics and Orthognathic Surgery; Journal of Clinical Orthodontics; 23(4); pp. 262- 268; 11 pages; (Author Manuscript); Apr. 1989.

Heaven et al.; Computer-Based Image Analysis of Artificial Root Surface Caries; Abstracts of Papers #2094; Journal of Dental Research; 70:528; (Abstract Only); Apr. 17-21, 1991.

Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa . . . ); on Nov. 5, 2004.

Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Included); Feb. 1987.

Hoffmann et al.; Role of Cephalometry for Planning of Jaw Orthopedics and Jaw Surgery Procedures; Informatbnen, pp. 375-396; (English Abstract Included); Mar. 1991.

Hojjatie et al.; Three-Dimensional Finite Element Analysis of Glass-Ceramic Dental Crowns; Journal of Biomechanics; 23(11); pp. 1157-1166; Jan. 1990.

Huckins; CAD-CAM Generated Mandibular Model Prototype from MRI Data; AAOMS, p. 96; (Abstract Only); (year of pub. sufficiently earlier than effective US filing date and any foreign priority date) 1999.

Imani et al.; A wearable chemical-electrophysiological hybrid biosensing system for real-time health and fitness monitoring; Nature Communications; 7; 11650. doi 1038/ncomms11650; 7 pages; May 23, 2016.

Invisalign; You were made to move. There's never been a better time to straighten your teeth with the most advanced clear aligner in the world; Product webpage; 2 pages; retrieved from the internet (www.invisalign.com/) on Dec. 28, 2017.

Jia et al.; Epidermal biofuel cells: energy harvesting from human perspiration; Angewandle Chemie International Edition; 52(28); pp. 7233-7236; Jul. 8, 2013.

Jia et al.; Wearable textile biofuel cells for powering electronics; Journal of Materials Chemistry A; 2(43); pp. 18184-18189; Oct. 14, 2014.

JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.

JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.

Jeerapan et al.; Stretchable biofuel cells as wearable textile-based self-powered sensors; Journal of Materials Chemistry A; 4(47); pp. 18342-18353; Dec. 21, 2016.

Jerrold; The Problem, Electronic Data Transmission and the Law; American Journal of Orthodontics and Dentofacial Orthopedics; 113(4); pp. 478-479; 5 pages; (Author Manuscript); Apr. 1998.

Jones et al.; An Assessment of the Fit of a Parabolic Curve to Pre- and Post-Treatment Dental Arches; British Journal of Orthodontics; 16(2); pp. 85-93; May 1989.

Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.

Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.

Kanazawa et al.; Three-Dimensional Measurements of the Occlusal Surfaces of Upper Molars in a Dutch Population; Journal of Dental Research; 63(11); pp. 1298-1301; Nov. 1984.

Kesling et al.; The Philosophy of the Tooth Positioning Appliance; American Journal of Orthodontics and Oral surgery; 31(6); pp. 297-304; Jun. 1945.

Kesling; Coordinating the Predetermined Pattern and Tooth Positioner with Conventional Treatment; American Journal of Orthodontics and Oral Surgery; 32(5); pp. 285-293; May 1946.

Kim et al.; Advanced materials for printed wearable electrochemical devices: A review; Advanced Electronic Materials; 3(1); 15 pages; 1600260; Jan. 2017.

Kim et al.; Noninvasive alcohol monitoring using a wearable tatto-based iontophoretic-biosensing system; Acs Sensors; 1(8); pp. 1011-1019; Jul. 22, 2016.

Kim et al.; Non-invasive mouthguard biosensor for continuous salivary monitoring of metabolites; Analyst; 139(7); pp. 1632-1636; Apr. 7, 2014.

Kim et al.; A wearable fingernail chemical sensing platform: pH sensing at your fingertips; Talanta; 150; pp. 622-628; Apr. 2016.

Kim et al.; Wearable salivary uric acid mouthguard biosensor with integrated wireless electronics; Biosensors and Bioelectronics; 74; pp. 1061-1068; 19 pages; (Author Manuscript); Dec. 2015.

Kleeman et al.; The Speed Positioner; J. Clin. Orthod.; 30(12); pp. 673-680; Dec. 1996.

Kochanek; Interpolating Splines with Local Tension, Continuity and Bias Control; Computer Graphics; 18(3); pp. 33-41; Jan. 1, 1984.

Kumar et al.; All-printed, stretchable Zn—Ag2o rechargeable battery via, hyperelastic binder for self-powering wearable electronics; Advanced Energy Materials; 7(8); 8 pages; 1602096; Apr. 2017.

Kumar et al.; Biomarkers in orthodontic tooth movement; Journal of Pharmacy Bioallied Sciences; 7(Suppl 2); pp. S325-5330; 12 pages; (Author Manuscript); Aug. 2015.

Kumar et al.; Rapid maxillary expansion: A unique treatment modality in dentistry; J. Clin. Diagn. Res.; 5(4); pp. 906-911; Aug. 2011.

Kunii et al.; Articulation Simulation for an Intelligent Dental Care System; Displays; 15(3); pp. 181-188; Jul. 1994.

Kuroda et al.; Three-Dimensional Dental Cast Analyzing System Using Laser Scanning; American Journal of Orthodontics and Dentofacial Orthopedics; 110(4); pp. 365-369; Oct. 1996.

Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.

Leinfelder et al.; A New Method for Generating Ceramic Restorations: a CAD-CAM System; Journal of the American Dental Association; 118(6); pp. 703-707; Jun. 1989.

Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.

McCann; Inside the ADA; J. Amer. Dent. Assoc, 118:286-294; Mar. 1989.

McNamara et al.; Invisible Retainers; J. Clin Orthod.; pp. 570-578; 11 pages; (Author Manuscript); Aug. 1985.

(56) References Cited

OTHER PUBLICATIONS

McNamara et al.; Orthodontic and Orthopedic Treatment in the Mixed Dentition; Needham Press; pp. 347-353; Jan. 1993.
Moermann et al, Computer Machined Adhesive Porcelain Inlays: Margin Adaptation after Fatigue Stress; IADR Abstract 339; J. Dent. Res.; 66(a);763; (Abstract Only); (year of pub. sufficiently earlier than effective US filing date and any foreign priority date) 1987.
Moles; Correcting Mild Malalignments—As Easy As One, Two, Three; AOA/Pro Corner; 11(2); 2 pages; (year of pub. sufficiently earlier than effective US filing date and any foreign priority date) 2002.
Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.
Nahoum; The Vacuum Formed Dental Contour Appliance; N. Y. State Dent. J.; 30(9); pp. 385-390; Nov. 1964.
Nash; CEREC CAD/CAM Inlays: Aesthetics and Durability in a Single Appointment; Dentistry Today; 9(8); pp. 20, 22-23 and 54; Oct. 1990.
Nedelcu et al.; "Scanning Accuracy and Precision in 4 Intraoral Scanners: An In Vitro Comparison Based on 3-Dimensional Analysis"; J. Prosthet. Dent.; 112(6); pp. 1461-71; Dec. 2014.
Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.
Ogawa et al.; Mapping, profiling and clustering of pressure pain threshold (PPT) in edentulous oral muscosa; Journal of Dentistry; 32(3); pp. 219-228; Mar. 2004.
Ogimoto et al.; Pressure-pain threshold determination in the oral mucosa; Journal of Oral Rehabilitation; 29(7); pp. 620-626; Jul. 2002.
Parrilla et al.; A textile-based stretchable multi-ion potentiometric sensor; Advanced Healthcare Materials; 5(9); pp. 996-1001; May 2016.
Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.
Pinkham; Foolish Concept Propels Technology; Dentist, 3 pages, Jan./Feb. 1989.
Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 ' Abstract Collection; 23 pages; (year of pub. sufficiently earlier than effective US filing date and any foreign priority date) 1993.
Proem et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.

Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD-CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of the PAR Index (Peer Assessment Rating): Reliability and Validity.; The European Journal of Orthodontics; 14(2); pp. 125-139; Apr. 1992.
Richmond et al.; The Development of a 3D Cast Analysis System; British Journal of Orthodontics; 13(1); pp. 53-54; Jan. 1986.
Richmond; Recording the Dental Cast in Three Dimensions; American Journal of Orthodontics and Dentofacial Orthopedics; 92(3); pp. 199-206; Sep. 1987.
Rudge; Dental Arch Analysis: Arch Form, A Review of the Literature; The European Journal of Orthodontics; 3(4); pp. 279-284; Jan. 1981.
Sahm et al.; "Micro-Electronic Monitoring of Functional Appliance Wear"; Eur J Orthod.; 12(3); pp. 297-301; Aug. 1990.
Sahm; Presentation of a wear timer for the clarification of scientific questions in orthodontic orthopedics; Fortschritte der Kieferorthopadie; 51 (4); pp. 243-247; (Translation Included) Jul. 1990.
Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.
Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.
Shilliday; Minimizing finishing problems with the mini-positioner; American Journal of Orthodontics; 59(6); pp. 596-599; Jun. 1971.
Shimada et al.; Application of optical coherence tomography (OCT) for diagnosis of caries, cracks, and defects of restorations; Current Oral Health Reports; 2(2); pp. 73-80; Jun. 2015.
Siemens; CEREC—Computer-Reconstruction, High Tech in der Zahnmedizin; 15 pagesl; (Includes Machine Translation); (year of pub. sufficiently earlier than effective US filing date and any foreign priority date); 2004.
Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.
Sirona Dental Systems GmbH, CEREC 3D, Manuel utiiisateur, Version 2.0X (in French); 114 pages; (English translation of table of contents included); (year of pub. sufficiently earlier than effective US filing date and any foreign priority date); 2003.
Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.

(56) References Cited

OTHER PUBLICATIONS

Sturman; Interactive Keyframe Animation of 3-D Articulated Models; Proceedings Graphics Interface '84; vol. 86; pp. 35-40; May-Jun. 1984.
The American Heritage, Stedman's Medical Dictionary; Gingiva; 3 pages; retrieved from the interent (http://reference.com/search/search?q=gingiva) on Nov. 5, 2004.
The Dental Company Sirona: Cerc omnicam and cerec bluecam brochure: The first choice in every case; 8 pages; (year of pub. sufficiently earlier than effective US filing date and any foreign priority date) 2014.
Thera Mon; "Microsensor"; 2 pages; retrieved from the internet (www.english.thera-mon.com/the-product/transponder/index.html); on Sep. 19, 2016.
Thorlabs; Pellin broca prisms; 1 page; retrieved from the internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(TM) Appliance System; The Functional Orthodontist; 9(5); pp. 22-24, 26-8; Sep.-Oct. 1992.
Tru-Tatn Orthodontic & Dental Supplies, Product Brochure, Rochester, Minnesota 55902, 16 pages; (year of pub. sufficiently earlier than effective US filing date and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.
Van Der Linden et al.; Three-Dimensional Analysis of Dental Casts by Means of the Optocom; Journal of Dental Research; 51(4); p. 1100; Jul.-Aug. 1972.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.
Van Hilsen et al.; Comparing potential early caries assessment methods for teledentistry; BMC Oral Health; 13(16); doi: 10.1186/1472-6831-13-16; 9 pages; Mar. 2013.
Varady et al.; Reverse Engineering of Geometric Models'An Introduction; Computer-Aided Design; 29(4); pp. 255-268; 20 pages; (Author Manuscript); Apr. 1997.
Verstreken et al.; An Image-Guided Planning System for Endosseous Oral Implants; IEEE Transactions on Medical Imaging; 17(5); pp. 842-852; Oct. 1998.
Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.
Warunek et.al.; Clinical Use of Silicone Elastomer Applicances; JCO; 23 (10); pp. 694-700; Oct. 1989.
Watson et al.; Pressures recorded at to denture base-mucosal surface interface in complete denture wearers; Journal of Oral Rehabilitation 14(6); pp. 575-589; Nov. 1987.
Wells; Application of the Positioner Appliance in Orthodontic Treatment; American Journal of Orthodontics; 58(4); pp. 351-366; Oct. 1970.
Wikipedia; Palatal expansion; 3 pages; retrieved from the internet (https://en.wikipedia.org/wiki/Palatal_expansion) on Mar. 5, 2018.
Williams; Dentistry and CAD/CAM: Another French Revolution; J. Dent. Practice Admin.; 4(1); pp. 2-5 Jan./Mar. 1987.
Williams; The Switzerland and Minnesota Developments in CAD/CAM; Journal of Dental Practice Administration; 4(2); pp. 50-55; Apr./Jun. 1987.
Windmiller et al.; Wearable electrochemical sensors and biosensors: a review; Electroanalysis; 25(1); pp. 29-46; Jan. 2013.
Wireless Sensor Networks Magazine; Embedded Teeth for Oral Activity Recognition; 2 pages; retrieved on Sep. 19, 2016 from the internet (www.wsnmagazine.com/embedded-teeth/); Jul. 29, 2013.
Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.
Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.
Wolf; Three-dimensional structure determination of semi-transparent objects from holographic data; Optics Communications; 1(4); pp. 153-156; Sep. 1969.
WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yamada et al.; Simulation of fan-beam type optical computed-tomography imaging of strongly scattering and weakly absorbing media; Applied Optics; 32(25); pp. 4808-4814; Sep. 1, 1993.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.
Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.
Zhou et al.; Bio-logic analysis of injury biomarker patterns in human serum samples; Talanta; 83(3); pp. 955-959; Jan. 15, 2011.
Zhou et al.; Biofuel cells for self-powered electrochemical biosensing and logic biosensing: A review; Electroanalysis; 24(2); pp. 197-209; Feb. 2012.
Grove et al.; U.S. Appl. No. 15/726,243 entitled "Interproximal reduction templates," filed Oct. 5, 2017.
Sato et al.; U.S. Appl. No. 16/041,606 entitled "Palatal contour anchorage," filed Jul. 20, 2018.
Sato et al.; U.S. Appl. No. 16/048,054 entitled "Optical coherence tomography for orthodontic aligners," filed Jul. 27, 2018.

(56) References Cited

OTHER PUBLICATIONS

Miller et al.; U.S. Appl. No. 16/038,088 entitled "Method and apparatuses for interactive ordering of dental aligners," filed Jul. 17, 2018.
Moalem et al.; U.S. Appl. No. 16/046,897 entitled Tooth shading, transparency and glazing, filed Jul. 26, 2018.
Nyukhtikov et al.; U.S. Appl. No. 15/998,883 entitled "Buccal corridor assessment and computation," filed Aug. 15, 2018.
Kopelman et al.; U.S. Appl. No. 16/152,281 entitled "Intraoral appliances for sampling soft-tissue," filed Oct. 4, 2018.
Morton et al.; U.S. Appl. No. 16/177,067 entitled "Dental appliance having selective occlusal loading and controlled intercuspation," filed Oct. 31, 2018.
Akopov et al.; U.S. Appl. No. 16/178,491 entitled "Automatic treatment planning," filed Nov. 1, 2018.
Elbaz et al.; U.S. Appl. No. 16/198,488 entitled "Intraoral scanner with dental diagnostics capabilities," filed Nov. 21, 2018.
Elbaz et al.; U.S. Appl. No. 16/188,262 entitled "Intraoral scanner with dental diagnostics capabilities," filed Nov. 12, 2018.
O'Leary et al.; U.S. Appl. No. 16/195,701 entitled "Orthodontic retainers," filed Nov. 19, 2018.
Shanjani et al., U.S. Appl. No. 16/206,894 entitled "Sensors for monitoring oral appliances," filed Nov. 28, 2019.
Kopleman et al., U.S. Appl. No. 16/220,381 entitled "Closed loop adaptive orthodontic treatment methods and apparatuses," filed Dec. 14, 2018.

\* cited by examiner

Developing Treatment Plan

Analyze Dental Appliance

Poor Fit

Good Fit

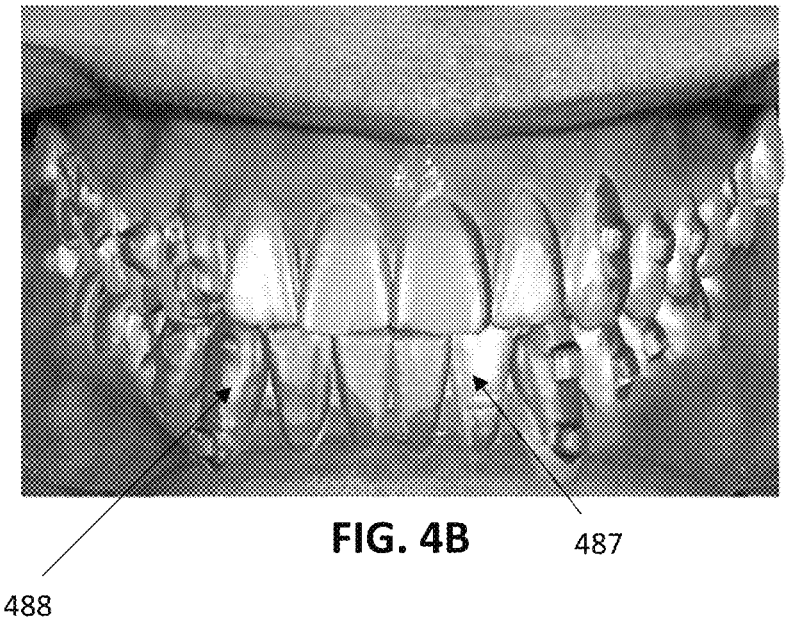

| Receive (e.g., in a processor of the AR system) a first data set comprising a treatment plan for a patient's teeth 458. |

↓

| Receive (receive, from an augmented reality system worn by a dental practitioner, an image data set comprising a representation of the patient's current teeth 460. |

↓

| Compare the first data set to the image data set to determine one or more variations from the treatment plan 462. |

↓

| Displaying the one or more variations on a visual display of the augmented reality system worn by the dental practitioner superimposed over a view of the patient's teeth 464. |

FIG. 4C

Analyze Attachments

Display Forces on teeth

Forces and moment on wire-based dental appliance

Displaying VR to patient

AUGMENTED REALITY ENHANCEMENTS FOR DENTAL PRACTITIONERS

CROSS REFERENCE TO RELATED APPLICATIONS

This patent application claims priority to U.S. Provisional Patent Application No. 62/612,308, filed on Dec. 29, 2017, titled "AUGMENTED REALITY ENHANCEMENTS FOR DENTAL PRACTITIONERS," which is herein incorporated by reference in its entirety.

This patent may be related to one or more of: U.S. patent application Ser. No. 15/841,212, filed Dec. 13, 2017 (titled "Augmented reality planning and viewing of dental treatment outcomes"); U.S. patent application Ser. No. 15/841,200, filed Dec. 13, 2017 (titled "Augmented reality enhancements for dental practitioners"); and U.S. patent application Ser. No. 15/841,196 filed Dec. 13, 2017 (titled "Augmented reality enhancements for dental practitioners"); and U.S. patent application Ser. No. 15/803,718 filed Nov. 3, 2017 (titled "Methods and apparatuses for dental images"). Each of these patent applications is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Orthodontic procedures typically involve repositioning a patient's teeth to a desired arrangement in order to correct malocclusions and/or improve aesthetics. To achieve these objectives, orthodontic appliances such as braces, shell aligners, and the like can be applied to the patient's teeth by an orthodontic practitioner. The appliance can be configured to exert force on one or more teeth in order to effect desired tooth movements according to a treatment plan. Augmented reality devices may provide additional information to users of the devices in the context of the surrounding real world environment. For example, an augmented reality device may provide audio, video, graphic, or other information to a user to supplement the information available in the real world environment.

SUMMARY OF THE DISCLOSURE

The present application relates to methods and apparatuses (e.g., devices and systems, including software) for using augmented reality or virtual reality systems to aid in orthodontic treatment planning.

The methods and apparatuses (e.g., systems, devices, etc.) described herein may be used to improve or assist in scanning of the teeth, tracking progress of an orthodontic treatment, forming or modifying an orthodontic treatment plan, and/or checking or modifying aspects of a treatment plan, including, but not limited to, placement and/or adjustment of attachments on a patient's teeth. In general, an augmented reality system, including in particular a system including one or more cameras on a wearable display (e.g., glasses, goggles, etc.) can be used to scan a patient's teeth, which may determine the position and/or orientation of the patient's teeth. The augmented reality system may therefore provide real-time scanning (including 3D imaging information) that may provide image data of the patient's teeth. This image data may include information about the position and orientation of the patient's individual teeth, and orthodontic components (e.g., aligners, palatal expanders, attachments, etc.) on the teeth, which may be compared with expected values from one or more treatment plans. This information may be interpreted in light of a more detailed 3D scan (e.g., using an intraoral scanner), without requiring the use of an intraoral scanner. In some variations a digital model of the patient's teeth may be used to interpret the augmented reality system images (e.g., the image data of the patient's current teeth, e.g., current dental arch(es)). The digital model may be prepared from an intraoral scanner. Thus, the methods and apparatuses described herein may assist in the analysis of a treatment plan at the start, finish or during a mid-treatment period, without requiring a full scan of the teeth using more complex intraoral scanning. These methods and systems may or additionally or alternatively be used to enhance a virtual reality display that a dental practitioner (e.g., dentist, orthodontist, dental technician, etc.) may customize for display to a patient (including in real time).

Thus, described herein are augmented reality (AR) and/or virtual reality (VR) methods and apparatuses (e.g., systems) to evaluate an orthodontic treatment plan. As described in detail below, such systems may be configured to show deviation(s) from current tooth position and/or orientation (angle, rotation, etc.) from one or more stages of a treatment plan.

The AR and/or VR systems described herein may alternatively or additionally be configured to review the position of and/or force(s) on one or more attachments on the patient's teeth. These systems may be configured to check the attachments at either the start of treatment (e.g., to show deviation of attachment positons from their intended position, and/or to describe forces on the one or more attachments) and/or during ongoing treatment (e.g., checking to be sure that the attachments are still present, and/or to describe forces on the one or more attachments).

The AR and/or VR systems described herein may be configured to estimate and/or display force(s) on the teeth and/or dental appliance and/or attachment(s) on the teeth. In some variations the AR and/or VR system may be configured to estimate and/or display the forces on the teeth and/or attachments when the patient is wearing an orthodontic appliance (e.g., an aligner, palatal expander, etc.). In some embodiments, the AR and/or VR systems described herein may be configured to determine how well a dental appliance (e.g., an aligner) fits a patient.

The methods and apparatuses may also be configured to include a slaved patient-wearable virtual reality display that displays a subset of the information displayed on a master dental professional-worn augmented reality display; the dental professional may control the slaved patient-wearable virtual reality display, including selecting the subset of information to be displayed. The slaved patient-wearable virtual reality display may show the image of the patient's teeth from the perspective of the dental professional, onto which is overlaid a subset of the augmented reality information that is shown on the master physician-wearable virtual reality device (e.g., highlighting teeth, movements, caries, etc.).

The methods and apparatuses described herein may also or alternatively be used to help design and/or modify a treatment plan. For example, an AR and/or VR system may be used to allow the dental professional to select one or more teeth to move, and to virtually move the one or more teeth to a final position and/or one or more intermediate (e.g., key) positions.

For example, described herein are methods of performing orthodontic treatment planning using augmented reality/virtual reality. Any of these methods may include: receiving, with a an augmented reality device (including a processor), a virtual model of a patient's teeth representing a dental arch, capturing, e.g., with the processor or other portion of the augmented reality device, image data of the patient's teeth, identifying, with the processor, a virtual selection by a user of at least one tooth from the virtual model and image data, generating, with the augmented reality device, a visual overlay identifying the virtual selection, outputting the visual overlay to a display of the augmented reality device, wherein the visual overlay is superimposed over a view of the patient's teeth identifying a virtual manipulation by the user of the virtual selection, wherein the virtual manipulation modifies the virtual model, generating an updated visual overlay corresponding to the virtual manipulation, outputting the updated visual overlay to the display, wherein the visual overlay is superimposed over the view of the patient's teeth.

Any of the steps of these methods described herein may be performed by the augmented reality device, including a processor of an augmented reality device. In some variations, a separate processor may be used (e.g., separate from the augmented reality device).

In any of the steps including manipulation of the at least one tooth, the manipulation may be real or virtual. For example, "real" manipulation may include contacting a patient's tooth with a tool, such as a dental/orthodontic tool, that includes a sensor that may indicate which tooth is selected and or what manipulations (e.g., application of force, rotation, including vector—e.g., magnitude and direction—is being applied). The tool may then create virtual information that may be overlaid as described. For example, an image processor of an augmented reality (AR) or virtual reality (VR) system can detect a real manipulation (probing of tooth) that could then be visualized in a virtual way. The display may be virtually exaggerated and displayed on the selected tooth, e.g., an image of the selected tooth and/or an overlay onto the selected actual tooth. For example, a tool may include one or more sensors (force sensor, tri-axial sensor(s), etc.). Alternatively the manipulation may be virtual.

For example, the processor may recognize a hand gesture of the user to identify the virtual selection. The hand gesture can include virtually or physically touching one or more of the patient's teeth.

As described herein, the visual overlay may comprise a visual outline of at least one tooth, shading or coloring of at least one tooth, or may comprise displaying the forces acting on the teeth.

As further described herein, the virtual manipulation may comprise moving the at least one tooth or rotating the at least one tooth.

Alternatively or additionally, the method may further comprise receiving an input from the user corresponding to the virtual manipulation, wherein the user is constrained in making a virtual manipulation based on a change in position of one or more teeth in the virtual model.

A method of performing orthodontic treatment planning is also provided, comprising generating a visual overlay comprising a virtual model of a dental arch, outputting the visual overlay to an augmented reality display, receiving user input based on a user interaction with at least one tooth of the virtual model of the dental arch, wherein the user input modifies the virtual model of the dental arch, determining a treatment plan for the dental arch based on the user input, and generating an updated visual overlay, wherein the updated visual overlay comprises a view of the dental arch after implementing the treatment plan.

The step of receiving user input based on a user interaction may be based on user interaction with at least one tooth of the virtual model of the dental arch or a patient's real dental arch.

For example, a user input may be a hand gesture of the user to identify the virtual selection. The hand gesture can include virtually or physically touching one or more of the patient's teeth.

As described herein, the visual overlay may comprise a visual outline of at least one tooth, shading or coloring of at least one tooth, or may comprise displaying force vectors resulting from the treatment plan.

As further described herein, the virtual manipulation may comprise moving the at least one tooth or rotating the at least one tooth. Additionally, the user interaction may include adding a virtual attachment to the at least one tooth. The methods described herein may further include identifying if the virtual attachment is improperly placed.

Alternatively or additionally, the method may further comprise receiving an input from the user corresponding to the virtual manipulation, wherein the user is constrained in making a virtual manipulation based on a change in position of one or more teeth in the virtual model.

A system comprising an augmented reality display a memory device and a processing device operatively coupled to the memory device is further provided, the processing device configured to generate a visual overlay comprising a virtual model of a dental arch, output the visual overlay to the augmented reality display, receive user input based on a user interaction with at least one tooth of the virtual model of the dental arch (and/or of the patient's actual/real tooth), wherein the user input modifies the virtual model of the dental arch, determine a treatment outcome for the dental arch based on the user input; generate an updated visual overlay, wherein the updated visual overlay comprises a view of the dental arch after implementing the treatment outcome.

In general, any of these apparatuses (e.g., systems) may include an processor (and/or image processing sensors) and/or one or more controllers. Examples of such system architectures are provided herein and may generally include a processing unit, a memory unit, etc.

The step of receiving user input based on a user interaction with at least one tooth of the virtual model of the dental arch or a patient's real tooth may be based on receiving user input from one or more sensor inputs, e.g., on a user-held device, such as a probe or dental tool that includes one or more sensors, as mentioned above. Hand gestures or verbal commands may be used in addition or alternatively. The system may generally include an optical control sensors. Thus, any of the apparatuses (e.g., systems) described herein may include one or more dental tools with a probe or sensor that feeds information to the AR/VR system. The data from the tool may be received and used by the apparatus/system.

For example, a user input may be a hand gesture of the user to identify the virtual selection. The hand gesture can include virtually or physically touching one or more of the patient's teeth.

As described herein, the visual overlay may comprise a visual outline of at least one tooth, shading or coloring of at least one tooth, or may comprise displaying force vectors resulting from the treatment plan.

As further described herein, the virtual manipulation may comprise moving the at least one tooth or rotating the at least one tooth. Additionally, the user interaction may include adding a virtual attachment to the at least one tooth. The methods described herein may further include identifying if the virtual attachment is improperly placed.

Alternatively or additionally, the method may further comprise receiving an input from the user corresponding to the virtual manipulation, wherein the user is constrained in making a virtual manipulation based on a change in position of one or more teeth in the virtual model.

Also described herein are methods of evaluating the fit of an orthodontic appliance such as an aligner. Any of these methods may include: capturing, with a processor of an augmented reality device, image data of a patient's teeth and of an appliance placed on the patient's teeth, identifying from the image data, with the processor, an error condition indicative of improper appliance fit on the patient's teeth, generating, with the processor, a visual overlay identifying the error condition, outputting the visual overlay to a display of the augmented reality device, wherein the visual overlay is superimposed over a view of the patient's teeth and of the appliance placed on the patient's teeth.

In general, the methods described herein may determine (e.g., create) one or more error conditions from just image data of the patient's teeth (or image data and additional sensor data), knowing what their expected position of teeth is going to be. For example, if the patient is in for a check-in appointment, and image data of the patient's teeth and treatment plan are provided to the system, the system may detect deviation from the treatment plan. The patient's dental health may be assessed by identifying/reviewing the error condition, including displacement of teeth under the input load. The apparatus may determine or detect a measure of tooth movement, force on the teeth, etc., and may precisely determine actual tooth movement. If the tooth movement is outside of an expected range, the apparatus may determine that the tooth movement is unhealthy and may flag/indicate this. This may be done based on predicted tooth movement as well/alternatively. The error condition may be determined between, for example, an aligner and an attachment on the tooth. Thus, the error condition may indicate an error in the position of the attachment; predicted fit may be estimated/determined by looking at the attachment on the tooth. The expected positon, size, and/or geometry of the attachment may be compared to the actual attachment, or the prescribed attachment from the treatment plan and used to generate an error condition.

In any of these methods and apparatuses, multiple error conditions may be simultaneously or sequentially presented (e.g., by AR/VR display).

As further described herein, the error condition can include a gap between the appliance and its corresponding tooth or a deformation of the appliance beyond a deformation threshold.

Alternatively or additionally, the method may further include displaying the error condition in a color. The visual overlay may be outputted to a display device worn on or over the user's head.

According to the present disclose, identifying the error condition may comprise determining, using an image of the orthodontic appliance, a region of poor fit between the patient's teeth and the orthodontic appliance. Identifying the error condition can also comprise estimating forces acting on the patient's teeth and indicating on the visual overlay where the forces exceed a threshold value. Estimating the forces acting on the patient's teeth can comprise identifying one or more elastics attached to the dental appliance.

As further described herein, a system is provided comprising an augmented reality display, a memory device, and a processing device operatively coupled to the memory device, the processing device configured to capture, with a processor of an augmented reality device, image data of a patient's teeth and of an aligner placed on the patient's teeth, identify from the image data, with the processor, an error condition indicative of improper aligner fit on the patient's teeth, generate, with the processor, a visual overlay identifying the error condition, output the visual overlay to a display of the augmented reality device, wherein the visual overlay is superimposed over a view of the patient's teeth and of the aligner placed on the patient's teeth.

As further described herein, the error condition can include a gap between the appliance and its corresponding tooth or a deformation of the appliance beyond a deformation threshold.

This disclosure further provides a method of evaluating attachment sites for an orthodontic appliance, such as an aligner, comprising capturing, with a processor of an augmented reality device, image data of a patient's teeth including one or more attachment sites for an orthodontic appliance attached to the patient's teeth, identifying from the image data, with the processor, an error condition indicative of improper position or orientation of one or more attachment site on the patient's teeth, generating, with the processor, a visual overlay identifying the error condition, outputting the visual overlay to a display of the augmented reality device, wherein the visual overlay is superimposed over a view of the patient's teeth and of the one or more attachment sites on the patient's teeth.

The method may further comprise receiving a target location for each of the one or more attachment sites on the patient's teeth.

Alternatively or additionally, the error condition may comprise a location of the attachment site that is different from a target location, or an orientation of the attachment site that is different from a target orientation.

According to the present disclosure, outputting the visual overlay can comprise displaying the error condition in a color and/or with an alphanumeric indicator, and outputting the visual overlay to a display device worn on or over the user's head.

Methods of evaluating an orthodontic treatment are also described. For example, these methods may include capturing, with a processor of an augmented reality device, image data of a patient's teeth, determining one or more effective forces on the patient's teeth when a dental appliance is applied to the patient's teeth, generating, with the processor, a visual overlay graphically illustrating the one or more effective forces, outputting the visual overlay to a display of the augmented reality device, wherein the visual overlay is superimposed over a view of the patient's teeth and of the elastic band or wire placed on the patient's teeth.

As further described herein, generating the visual overlay can comprise representing the one or more effective forces as an arrow, an alphanumeric value, or as a color. The one or more effective forces on the patient's teeth can be determined by determining a length and/or angle of an elastic band or wire on the dental appliance.

Determining the one or more effective forces on the patient's teeth can comprise determining a moment or torque on one or more teeth.

As further described herein, the method can include capturing the image of the patient's teeth when the dental appliance is worn by the patient, capturing the image of the patient's teeth when the dental appliance is not being worn by the patient and receiving a virtual model of the dental appliance.

For example, described herein are methods of evaluating an orthodontic treatment that may include: capturing, with a processor of an augmented reality device, image data of a patient's teeth; determining one or more effective forces on the patient's teeth when a dental appliance is applied to the patient's teeth; generating, with the processor, a visual overlay graphically illustrating the one or more effective forces; and outputting the visual overlay to a display of the augmented reality device, wherein the visual overlay is superimposed over a view of the patient's teeth and of the dental appliance placed on the patient's teeth.

The appliance may be any appliance, including elastics that may be worn to apply force to the teeth and/or wires. Other appliances may include aligners (e.g., having a bite ramp and/or other force-applying region), palatal expanders, and the like.

Forces on the teeth and/or apparatus may be determined and displayed by the AR/VR apparatuses as part of any of these methods. For example, force may be shown by force overlays. Types of force overlays that may be applied may include overlays showing the forces predicted, estimated or actually applied (measured) on the teeth and/or appliance. Force overlays may be shown graphically with or without text, including showing vectors (e.g., indicating direction and/or magnitude, including rotational forces (torque, etc.). In some variations the force overlay maybe shown without requiring other components of an AR/VR system, including just providing an annotated description/image, or listing of the forces predicted, estimated or actually applied. The display of such force maps may be particularly helpful to a user, adding information/data that the user (e.g., dental practitioner, physician, etc.) may use to form or modify a treatment plan. This information may be displayed in real time (e.g., instantaneously), effectively augmenting the data of the user.

In some variations the data (force data) may correspond to data from a dental probe or other dental device. For example, force applied by the dental probe may be shown in a realistic or exaggerated display, indicating potential tooth movements and their consequences, including consequence of a dental plan. For example, image data may be combined with input data (e.g., from a dental probe) and shown in the display either as force data or as movements due to applied force.

In some variations, the virtual data may highlight/exaggerate features from the scan of the patient's teeth that indicate dental issues (e.g., tartar, etc.) and the dental probe may indicate the interaction with such features. For example, tartar of other elements of the teeth may be shown in color on a representation of the teeth and a sensor on a dental tool (e.g., pick, probe, etc.) may show the interaction of the tool with the highlighted/colored feature(s), including showing (in a patient view) the removal (actual, simulated and/or predicted) removal.

Also described herein are systems comprising an augmented reality display, a memory device, and a processing device operatively coupled to the memory device, the processing device to capture, with a processor of an augmented reality device, image data of a patient's teeth and of an elastic band or wire placed on the patient's teeth, determine from the image data, with the processor, a length and/or angle of the elastic band or wire, and an effective force on a center of rotation of at least one of the patient's teeth resulting from the elastic band or wire, generate, with the processor, a visual overlay identifying the effective force, output the visual overlay to a display of the augmented reality device, wherein the visual overlay is superimposed over a view of the patient's teeth and of the elastic band or wire placed on the patient's teeth.

Also described herein are methods of displaying an orthodontic procedure. Any of these methods may include: capturing, with a processor of an augmented reality device, image data of a patient's teeth, generating, with the processor, a first visual overlay graphically illustrating one or more features of the patient's teeth and/or information about the patient's teeth, generating, from the first visual overlay, a second visual overlay comprising a subset of the one or more features of the patient's teeth and/or information about the patient's teeth, outputting the first visual overlay to a first, user-worn, display of the augmented reality device, wherein the first visual overlay is superimposed over a view of the patient's teeth, and outputting the second visual overlay to a second user-worn display of the augmented reality device, which may be superimposed over the view of the patient's teeth.

As further described herein, outputting the second visual overlay can be done concurrently with outputting the first visual overlay, or can be done after a time delay from outputting the first visual overlay.

Alternatively, generating the first visual overlay can comprise graphically illustrating movement of one or more of the patient's teeth, or indicating one or more dental carries on the patient's teeth.

In general, the methods and apparatuses described herein may display 'slave' visual outputs (visual overlay) that may be displayed as an overlay on an image of the patient's teeth (as seem by the 'master' device, e.g., worn by the dental professional), or may be viewed just an overlay animation without the 'real' image of the teeth. The slave display may be viewed by an assistant and/or by the patient. In some example, the patient may view a patient-specific display. The master display may be modified by the primary user (e.g., dental professional) for display in real time or with a time delay to the slave display(s). For example, the master user may modify the display to highlight a region or to include an additional image of a region for display to the slave display. As mentioned, the slave display may be transmitted and viewed by a patient, by another dental professional (doctor, orthodontist, etc.) or to an assistant. For example, the slave display may be viewed by another dental professional that may offer advice or assistance, etc. for training or for handling more difficult cases. In some variations, the display may be broadcast to one or more external sources to get live feedback/advice (e.g., on how to handle the case). This method (or an apparatus configured to perform such a method) may be used, for example, for virtual training and/or for treatment planning. The dental professional may download a virtual patient and be shown a preview of aligner treatment on the virtual patient. In some variations these methods and apparatuses may provide information on soft tissue, such as gingiva, including the effect of dental treatment (actual or planned) on impingement or other treatment of the soft tissue. This may be particularly helpful for treatment of palatal expanders, for example.

As mentioned above, the methods and apparatuses described herein may be used to provide one or more AR and/or VR systems to analyze treatment progress, e.g., to analyze how an orthodontic treatment plan is progressing.

For example, a method of evaluating an orthodontic treatment may include: receiving, in a processor, a first data set comprising a treatment plan for a patient's teeth; receiving, from an augmented reality system worn by a dental practitioner, an image data set comprising a representation of the patient's current teeth; comparing the first data set to the image data set to determine one or more variations from the treatment plan; displaying the one or more variations on a visual display of the augmented reality system worn by the dental practitioner superimposed over a view of the patient's teeth.

Any of these methods may be methods of evaluating an orthodontic treatment using an augmented reality system worn by a dental practitioner, and may include: receiving, in a processor of the augmented reality system, a first data set comprising a treatment plan for a patient's teeth; receiving from the augmented reality system, an image data set comprising a representation of the patient's current teeth; determining the positions and orientations of one or more of the patient's teeth relative to the patient's dental arch from the image data set; comparing the positions and orientations of the one or more of the patient's teeth relative to the patient's dental arch with the treatment plan to determine one or more variations from the treatment plan; and displaying the one or more variations on a visual display of the augmented reality system worn by the dental practitioner superimposed over a view of the patient's teeth.

Any of these methods may also include receiving a virtual model of a patient's teeth representing a dental arch, and further wherein determining the positions and orientations of one or more of the patient's teeth relative to the patient's dental arch from the image data set comprises matching the image data of the patient's teeth to a virtual model of the patient's teeth to identify corresponding teeth from the image data of the patient's teeth.

The virtual model of the patient's teeth may include a scan taken prior to the start of the orthodontic treatment.

Displaying the variations may comprise displaying a color on the view of the patient's teeth and/or an alphanumeric indicator and/or an outline or partial outline (highlighting) of the patient's teeth.

Any of these methods may also include identifying a stage of the treatment plan most closely corresponding to an arrangement of the patient's current teeth and wherein comparing the first data set to the image data set comprises comparing the stage of the treatment plan most closely corresponding to the arrangement of the patient's current teeth with the image data set to determine one or more variations. For example, identifying the stage of the treatment plan may comprise receiving the stage from the dental practitioner. Identifying the stage of the treatment plan may comprise identifying the stage with a lowest value for the one or more variations.

Comparing the first data set to the image data set may comprise comparing each stage of the treatment plan of the first data set to the image data set and further wherein displaying the one or more variations comprises displaying the one or more variations specific to each stage of the treatment plan.

The one or more variations may comprise one or more of: a difference in a tooth position relative to the patient's dental arch between a tooth of the patient's current teeth and a corresponding position of the tooth in a stage of the treatment plan from the first data set; a difference in an angle of the tooth relative to the patient's dental arch of the patient's current teeth and a corresponding angle of the tooth in a stage of the treatment plan of the first data set; and a difference in rotational position relative to the patient's dental arch of a tooth between a tooth of the patient's current teeth and a corresponding rotational position of the tooth in a stage of the treatment plan of the first data set.

Also described herein are systems for performing any of these methods, including, for example, a system comprising: an augmented reality display; one or more processors; a memory coupled to the one or more processors, the memory configured to store computer-program instructions, that, when executed by the one or more processors, perform a computer-implemented method comprising: receiving, in a processor, a first data set comprising a treatment plan for a patient's teeth; receiving, from an augmented reality system worn by a dental practitioner, an image data set comprising a representation of the patient's current teeth; comparing the first data set to the image data set to determine one or more variations from the treatment plan; displaying the one or more variations on a visual display of the augmented reality system worn by the dental practitioner superimposed over a view of the patient's teeth.

As described above, also described herein are AR and/or VR methods and apparatuses for analyzing attachments. In general an attachment may be a polymeric, metal and/or ceramic attachment that is bonded to a patient's tooth to help engage with a dental appliance (e.g., aligner, etc.) to help secure it in position. The AR and/or VR methods and apparatuses may determine the position and/or orientation of one or more appliances, determine and display forces acting on them, and or determine and display deviation from an intended position of the one or more appliances. For example, a method of evaluating attachments for an orthodontic appliance may include: capturing, with an augmented reality system including a wearable display worn by a dental practitioner, image data of a patient's teeth including one or more attachments for an orthodontic appliance configured to be attached to the patient's teeth; identifying from the image data, with the processor, an error condition indicative of improper position or orientation of the one or more attachments on the patient's teeth; generating a visual overlay identifying the error condition; and outputting the visual overlay to the wearable display worn by the dental practitioner, wherein the visual overlay is superimposed over a view of the patient's teeth and of the one or more attachments on the patient's teeth.

A method of evaluating attachments for an orthodontic appliance may include: capturing, with an augmented reality system including a wearable display worn by a dental practitioner, image data of a patient's teeth including one or more attachments for an orthodontic appliance attached to the patient's teeth; identifying from the image data, with the processor one or more of: forces acting on the one or more attachments, and an error condition indicative of improper position or orientation of the one or more attachments on the patient's teeth; generating a visual overlay identifying one or more of: the forces acting on the one or more attachments and the error condition; and outputting the visual overlay to the wearable display worn by the dental practitioner, wherein the visual overlay is superimposed over a view of the patient's teeth and of the one or more attachments on the patient's teeth.

Capturing be performed at the start of an orthodontic treatment and/or during an ongoing orthodontic treatment (e.g., at or between any of the stage of an orthodontic treatment, and/or at the end of the orthodontic treatment.

Any of these methods may include receiving a target location for each of the one or more attachments on the patient's teeth. Any of these methods may include receiving one or more of: a target location, position, size, shape, or orientation for each of the one or more attachments on the patient's teeth.

The error condition may indicate a difference in the location of the attachment that is different from a target attachment site location and/or a difference in the rotation of the attachment relative to a target attachment orientation (e.g., the error condition may comprise an orientation of the attachment that is different from a target orientation) and/or a missing attachment (e.g., the error condition may comprise one or more missing attachments).

In any of these methods, outputting the visual overlay may comprise displaying the error condition in a color and/or with an alphanumeric indicator. In some variations, outputting the visual overlay to a display of the augmented reality device may comprise outputting the visual overlay to a plurality of displays concurrently.

Also described herein are systems for performing any of these methods. For example, a system for evaluating attachments for an orthodontic appliance may include: a wearable augmented reality display; one or more processors; a memory coupled to the one or more processors, the memory configured to store computer-program instructions, that, when executed by the one or more processors, perform a computer-implemented method comprising: capturing image data of a patient's teeth including one or more attachment sites for an orthodontic appliance attached to the patient's teeth; identifying from the image data, with the processor, an error condition indicative of improper position or orientation of one or more attachments on the patient's teeth; generating a visual overlay identifying the error condition; outputting the visual overlay to the wearable augmented reality display to display the visual overlay superimposed over a view of the patient's teeth and of the one or more attachments on the patient's teeth.

As mentioned above, also described herein are methods and apparatuses for estimating and displaying forces on the teeth and/or dental appliance and/or attachments. For example, described herein are methods of evaluating an orthodontic treatment comprising: capturing, with a processor of an augmented reality device, image data of a patient's teeth; determining one or more effective forces on the patient's teeth when a dental appliance is applied to the patient's teeth; generating a visual overlay graphically illustrating the one or more effective forces; and outputting the visual overlay to a display of the augmented reality device worn by a dental practitioner, wherein the visual overlay is superimposed over a view of the patient's teeth and of the dental appliance placed on the patient's teeth.

The dental appliance may include an elastic band or wire.

In any of these methods, generating the visual overlay may comprise representing the one or more effective forces as an arrow. Generating the visual overlay may comprise representing the one or more effective forces as an alphanumeric value. Generating the visual overlay may comprise representing the one or more effective forces as a color. Any of these method may include determining one or more effective forces on the patient's teeth by determining a moment or torque on one or more teeth.

Capturing the image of the patient's teeth may comprise capturing the image of the patient's teeth when the dental appliance is worn by the patient. For example, capturing the image of the patient's teeth may comprise capturing the image of the patient's teeth when the dental appliance is not being worn by the patient; further comprising receiving a virtual model of the dental appliance.

In some variations, determining one or more effective forces on the patient's teeth may comprise determining a length and/or angle of an elastic band or wire on the dental appliance.

Also described herein are systems comprising: an augmented reality display; one or more processors; and a memory coupled to the one or more processors, the memory configured to store computer-program instructions, that, when executed by the one or more processors, perform a computer-implemented method comprising: capturing, with a processor of an augmented reality device, image data of a patient's teeth and of an elastic band or wire placed on the patient's teeth; determining from the image data, with the processor, a length and/or angle of the elastic band or wire, and an effective force on a center of rotation of at least one of the patient's teeth resulting from the elastic band or wire; generating, with the processor, a visual overlay identifying the effective force; and outputting the visual overlay to a display of the augmented reality device, wherein the visual overlay is superimposed over a view of the patient's teeth and of the elastic band or wire placed on the patient's teeth.

As mentioned above, also described herein are augmented reality and/or virtual reality systems and methods in which a dental professional master AR device may control operation of a slave patient-worn display (e.g., VR) device. These apparatuses may be used as part of an orthodontic procedure. For example, a method of displaying an orthodontic procedure, the method comprising: capturing, with a processor of an augmented reality system, image data of a patient's teeth; displaying, on a user augmented reality display device worn by a dental practitioner, a first visual overlay based on the image data of the patient's teeth, the first visual overlay graphically illustrating one or more of: features of the patient's teeth an information about the patient's teeth, wherein the first visual overlay is superimposed over a view of the patient's teeth; adjusting, by the dental practitioner, the first visual overlay, wherein the dental practitioner interactively engages with the first visual overlay; and displaying, on a patient display device worn by a patient, a second visual overlay comprising a subset of the one or more of: features of the patient's teeth and/or information about the patient's teeth, wherein the second visual overlay is superimposed over the view of the patient's teeth, wherein the dental practitioner controls the display of the second visual overlay.

For example, a method of displaying an orthodontic procedure, the method comprising: capturing, with an augmented reality system, image data of a patient's teeth; generating, from the image data, a first visual overlay graphically illustrating one or more of: one or more features of the patient's teeth, and information about the patient's teeth; outputting the first visual overlay to a user augmented reality display device worn by a dental practitioner, wherein the first visual overlay is superimposed over a view of the patient's teeth; generating, from the first visual overlay, a second visual overlay comprising a subset of the one or more of: features of the patient's teeth and/or information about the patient's teeth, wherein the dental practitioner modifies content from the first visual overlay to form the second visual overlay; and displaying, on a patient display device worn by a patient, the second visual overlay, wherein the second visual overlay comprises a representation of one or more of the patient's teeth.

Any of these methods may include interactively engaging with the first visual overlay by the dental practitioner, wherein the dental practitioner performed one or more of: moving, highlighting, or modifying the one or more of:

features of the patient's teeth an information about the patient's teeth, wherein the first visual overlay is superimposed over a view of the patient's teeth.

These methods may also or alternatively include forming the second visual overlay by receiving, from the dental practitioner, the subset of the one or more of: features of the patient's teeth and/or information about the patient's teeth.

Outputting the second visual overlay may be done concurrently with outputting the first visual overlay. Displaying the second visual overlay may be done after a time delay from outputting or displaying the first visual overlay. Generating the first visual overlay may comprise generating a first visual overlay graphically illustrating movement of one or more of the patient's teeth. In some variations, generating the first visual overlay comprises indicating one or more dental carries on the patient's teeth. Any of these methods may include generating the second visual overlay by receiving modifications to the first visual overlay from dental practitioner.

Displaying the second visual overlay to a patient display device may comprise displaying the second visual overlay superimposed over a view of the patient's teeth.

As mentioned above, also described herein are AR and/or VR apparatuses and methods of using them for orthodontic treatment planning. For example, a method of performing orthodontic treatment planning may include: receiving a virtual model of a patient's teeth representing a dental arch; capturing, with an augmented reality system, image data of the patient's teeth; matching the virtual model of the patient's teeth to the image data of the patient's teeth to identify corresponding teeth from the image data of the patient's teeth; collecting, with the augmented reality system, a selection by a user of at least one tooth while capturing image data of the patient's teeth; generating, with the augmented reality system, a visual overlay identifying the selected at least one tooth; outputting the visual overlay to a display of the augmented reality system, wherein the visual overlay is superimposed over a view of the patient's teeth; receiving, in the augmented reality system, a translation of the selected at least one tooth by the user, wherein the translation modifies one or more of tooth angle relative to the patient's dental arch and tooth position relative the dental arch; updating the visual overlay to include the translation; modifying a target tooth virtual model of the patient's teeth to include the translation of the selected at least one tooth; and transferring the target tooth virtual model to a treatment plan generator to generate an orthodontic treatment plan. The augmented reality system may recognize a hand gesture of the user to identify the selection by the user of at least one tooth while capturing image data of the patient's teeth.

In some variations, the visual overlay comprises a visual outline of the at least one tooth. For example, the visual overlay may comprise shading or coloring of the at least one tooth. Receiving the translation may comprise sensing contact between a tooth of the patient and a dental tool comprising a sensor. The translation may comprise virtually moving the at least one tooth relative to the patient's dental arch. The translation may comprise virtually rotating the at least one tooth relative to the patient's dental arch.

Any of these methods may include repeating the steps of collecting, generating, outputting, receiving, updating and modifying to allow the user to select and adjust different target teeth.

For example, a method of performing orthodontic treatment planning may include: generating a visual overlay comprising a virtual model of a dental arch; outputting the visual overlay to an augmented reality display; receiving user input based on a user interaction with at least one tooth of the virtual model of the dental arch or a patient's real dental arch, wherein the user input modifies the virtual model of the dental arch; determining a treatment plan for the dental arch based on the user input; and generating an updated visual overlay, wherein the updated visual overlay comprises a view of the dental arch after implementing the treatment plan. The user input may comprise a hand gesture. The user input may comprise contact between a tooth of the patient and a dental tool comprising a sensor.

The visual overlay may comprises a visual outline of at least one tooth. The visual overlay may comprises shading or coloring of the at least one tooth.

The user interaction may comprises moving the at least one tooth. The user interaction may comprise rotating the at least one tooth. In some variations, the user interaction comprises adding a virtual attachment to the at least one tooth.

Any of these methods may include identifying if the virtual attachment is improperly placed.

The updated visual overlay may include force vectors resulting from the treatment plan.

Also described herein are systems for performing any of these methods. For example a system may include: an augmented reality display; one or more processors; and a memory coupled to the one or more processors, the memory configured to store computer-program instructions, that, when executed by the one or more processors, perform a computer-implemented method comprising: generating a visual overlay comprising a virtual model of a dental arch; outputting the visual overlay to the augmented reality display; receiving user input based on a user interaction with at least one tooth of the virtual model of the dental arch or a patient's real tooth, wherein the user input modifies the virtual model of the dental arch; determining a treatment outcome for the dental arch based on the user input; generating an updated visual overlay, wherein the updated visual overlay comprises a view of the dental arch after implementing the treatment outcome.

As described above, also described herein are AR and/or VR methods and apparatuses for analyzing the fit of one or more orthodontic appliances on a patient's teeth. For example, described herein are methods of evaluating fit of an orthodontic appliance, comprising: receiving an image data of an appliance placed on the patient's teeth; identifying from the image data, using an augmented reality system, an error condition indicative of improper appliance fit on the patient's teeth; generating, with the processor, a visual overlay identifying the error condition; outputting the visual overlay to a display of the augmented reality device, wherein the visual overlay is superimposed over a view of the patient's teeth and of the appliance placed on the patient's teeth.

The error condition may include a gap between the appliance and its corresponding tooth; alternatively or additionally, the error condition may include deformation of the appliance beyond a deformation threshold. Outputting the visual overlay may comprise displaying the error condition in a color. Identifying the error condition may comprise determining, using an image of the orthodontic appliance, a region of poor fit between the patient's teeth and the orthodontic appliance. In any of these methods, the orthodontic appliance may comprise an aligner (e.g., a shell aligner). Any of these methods may include identifying the error condition by estimating forces acting on the patient's teeth and indicating on the visual overlay where the forces exceed a threshold value. For example, estimating forces acting on the patient's teeth may comprise identifying one or more elastics attached to the dental appliance.

In any of the methods described herein, outputting the visual overlay to a display of the augmented reality device may comprise outputting the visual overlay to a display device worn on or over the user's head.

Also described herein are systems configured to perform any of the methods described herein, including a system comprising: an augmented reality display; one or more processors; and a memory coupled to the one or more processors, the memory configured to store computer-program instructions, that, when executed by the one or more processors, perform a computer-implemented method comprising: capturing, with a processor of an augmented reality device, image data of a patient's teeth and of an aligner placed on the patient's teeth; identifying from the image data, with the processor, an error condition indicative of improper aligner fit on the patient's teeth; generating, with the processor, a visual overlay identifying the error condition; outputting the visual overlay to a display of the augmented reality device, wherein the visual overlay is superimposed over a view of the patient's teeth and of the aligner placed on the patient's teeth.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4B is an example of a superposition (e.g., overlay) view of an AR system output showing deviation of a patient's teeth from a treatment plan.

FIG. 4C is a schematic (e.g., flowchart) showing an example of a method of evaluating an orthodontic treatment.

DETAILED DESCRIPTION

Figure 1A:
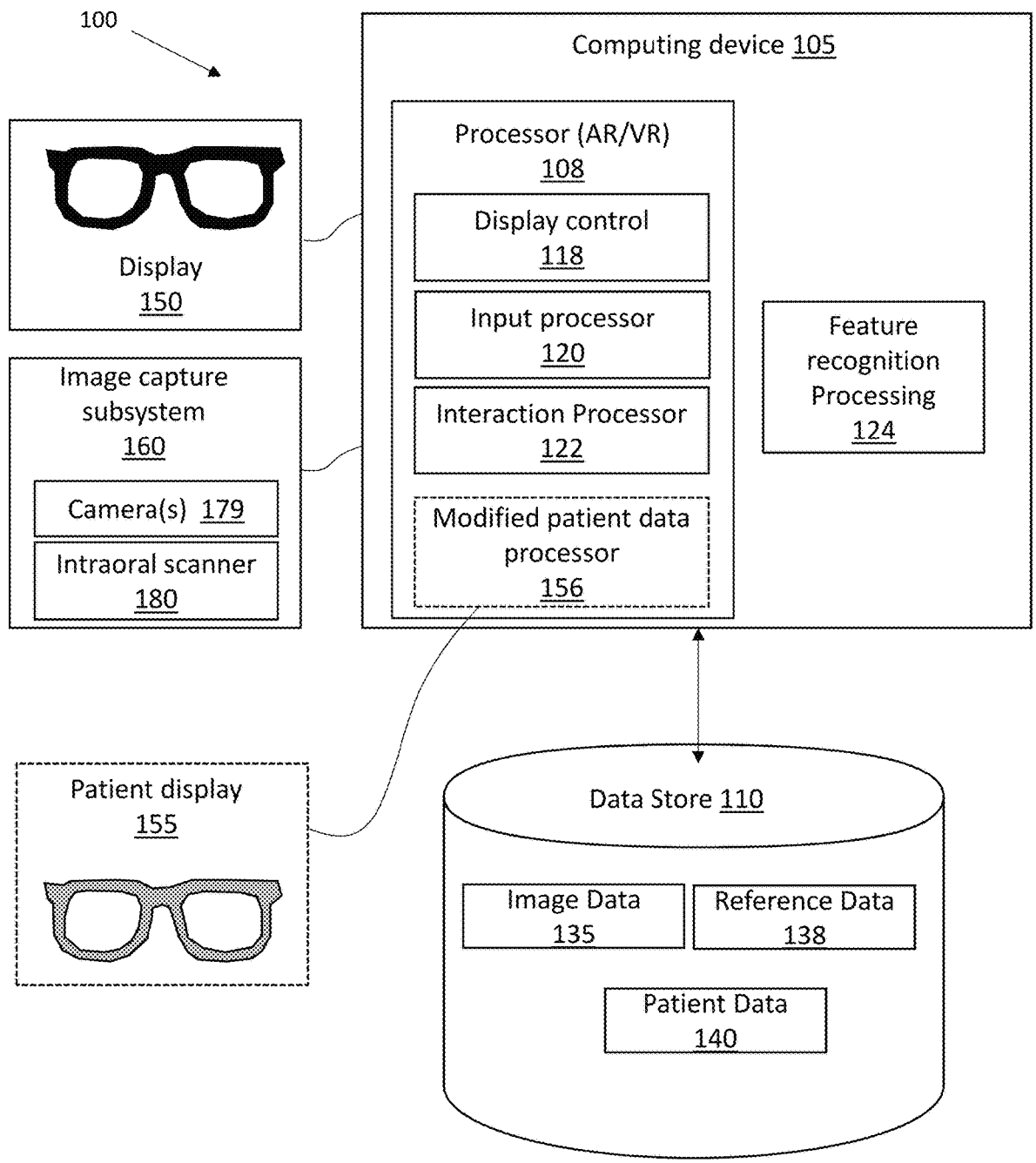
FIG. 1A illustrates one embodiment of an AR system for providing augmented reality enhancements to a dental practitioner.

Described herein are methods and apparatuses for providing augmented reality (AR) and/or virtual reality (VR) enhancements to dentists, orthodontists, dental hygienists, or other dental practitioners. An AR apparatus (e.g., an AR system, also referred to herein as an AR device) may provide real-time information to a dental practitioner based on an analysis of the mouth and/or dental arch of a patient as viewed through an AR display.

For example, the AR system may provide information about a dental arch based on images captured of the patient by the AR system. The AR system may also provide additional information based on a comparison of images captured by the AR system and previous data recorded for the patient. For example, previous images, scans, models, clinical data or other patient history may be compared to the images captured by the AR system, and a result of the comparison may be provided to the dental practitioner as a visual overlay on the real-world scene viewed by the dental practitioner through an AR display of the AR system. Previous data about the patient may also be provided in the visual overlay.

Additionally, image data from the AR system may be used to facilitate dental procedures such as drilling, grinding of a tooth, placement of an attachment on a tooth, placement of a bracket on a tooth (e.g., a bracket placed in the middle of the crown of a tooth), placement of other objects in predefined or automatically identified positions, intraoral scanning, and so on. The AR system may update information provided to a dental practitioner or provide feedback to the dental practitioner in real time or near real time during the course of the dental practitioner interacting with the patient.

As described herein, an AR system may provide information to the dental practitioner based on analysis of image data. For example, the AR system may analyze an image or stream of images of a patient's oral cavity and dental arch and determine an area of interest present in the image data. The AR system may determine if one or more teeth in an image indicate excessive wear, plaque, deposits, cracks, cavities, or other characteristics of interest to dental practitioners. The areas of interest may be determined based on processing an image of a dental arch or tooth taken by the AR system using one or more dental condition profiles in a data store. In some embodiments, the AR system may analyze an image of a tooth, multiple teeth, or a dental arch using dental condition profiles generated using machine learning techniques and training data of previous images of teeth. Examples of machine learning techniques (including in particular, deep learning for use with dental applications) may be found, for example, in U.S. provisional patent application No. 62/582,785, titled "DEEP LEARNING FOR TOOTH DETECTION AND EVALUATION," filed on Nov. 7, 2017, and any utility application claiming priority thereto, herein incorporated by reference in its entirety.

After the AR system determines one or more areas of interest, the AR display may then display real world data to a dental practitioner along with a visual overlay highlighting the areas of interest to the dental practitioner. In an example, the AR display may include lenses through which a wearer views the physical world, and the visual overlay may be projected onto the lenses. Alternatively, the visual overlay may be projected directly onto a wearer's eyes. For example, a tooth may be highlighted in a different color, circled, or otherwise indicated as having a characteristic in a visual overlay displayed by the AR system. For example, the AR system may provide different indicators for different characteristics or dental conditions. Furthermore, an area of interest may be highlighted, and a reason for the area of interest may be output in another portion of the display of the AR system or may be output in another manner, such as audio. Additionally, the AR system may also enhance a live view of the patient, such as by providing light enhancements that improve viewing of the patient or providing a zoomed in image of a portion of a patient's mouth.

As described herein, the AR system may provide information to the dental practitioner based on analysis of the patient and/or in view of previous patient data. For example, the AR system may compare images or models from a previous visit to current images of the patient's dental arch. The AR system may then determine one or more areas of interest based on the comparison. For example, the AR system may identify changes since a last scan, analysis of wear over time, feedback on orthodontic treatment, or other analysis of changes. The AR system may then mark the changes on a display of the AR system. The AR system may also superimpose previous patient data on a display. For example, the AR system may show a previous scan or previous dental arch superimposed onto a display.

Additionally, the AR system may provide interactive feedback or other updated information to the dental practitioner based on an interaction with the patient. For example, the feedback may be provided during an intra-oral treatment such as a dental procedure. The AR system may output to a display of the AR system recommended steps to take during an implant procedure, drilling procedure, grinding procedure, etc. For example, the AR system may show where to remove material for an insertion path, potential undercuts of neighboring teeth, placement of a hole for an implant, drilling depth, drilling direction, or the like. Similarly, the AR system may provide an indication of material to remove during interproximal reduction. The AR system may also provide feedback regarding placement of an attachment on a tooth. The AR system may also superimpose an occlusion map onto the patient's teeth in a display of the AR system. The AR system may also update a superimposed occlusion map if it changes while a dental practitioner is performing a dental procedure. An AR system may also provide feedback based on other information or analysis performed on images or other data received about a patient.

As further described herein, the AR system may allow a user to virtually select and manipulate one or more of a patient's teeth, and to change or provide treatment planning for the patient. The AR system can produce a visual overlay that shows the virtual manipulation, and how it will affect the treatment result. For example, a user can move or rotate one or more virtual teeth of the patient, and if satisfied with the placement, can implement the manipulation into the treatment planning.

Additionally, the AR system can identify error conditions with a patient's dental appliance, such as poor fit or misalignment of the dental appliance on the patient's teeth. The AR system can provide an overlay identifying the error conditions, which can be used to further fine tune the fitment of dental appliances.

The methods and apparatus described herein provide significant advantages over traditional techniques for dentistry and orthodontics, and can improve every aspect of a dental practice. Dental hygienists can use an AR system as described herein to better interact with a patient and identify potential dental issues that a dental hygienist is qualified to address, such as gum swelling or plaque caused by poor dental hygiene. The AR system may automatically process image data from the image capture subsystem to identify, for example, tooth wear, gum swelling, gum discoloration, plaque, etc. and call these dental conditions to the attention of the dental hygienist.

Similarly, a dentist may use an AR system that provides real-time feedback as described herein to improve his or her accuracy in performing intraoral procedures such as drilling a tooth, grinding a tooth, placing an attachment on a tooth, placing an implant, and so on. The AR system also presents information to a dental practitioner while the dental practitioner views a patient, and may reduce or eliminate a need for the dental practitioner to look away from the patient to a computer screen or chart. Additionally, an orthodontist may use an AR system as described herein to improve his analysis of how an orthodontic treatment plan is progressing, to improve performance of intraoral procedures, and so on. Embodiments therefore improve the efficiency of interfacing with patients, the accuracy of dental procedures and the identification of dental conditions. For example, embodiments enable a dental practitioner to work while looking exclusively at the patient's jaws, without any reason to turn his or her head toward a screen or monitor (e.g., of a computing device for an intraoral scanner).

As described herein, an intraoral scanner may use an AR display as a primary or secondary display for controlling an intraoral scanning procedure. The AR display may be worn by a dental practitioner that uses the intraoral scanner to image a patient's dental arch and generate a virtual three-dimensional model of that dental arch. The AR display may provide a two-dimensional (2-D) or three-dimensional (3-D) menu of options for controlling the intraoral scan procedure. Additionally, the AR display may be used to provide a zoomed in view of a region of the dental arch being scanned. Additionally, the AR display may be used to provide a virtual overlay of a virtual 3-D model of the dental arch based on images generated by the intraoral scanner during an intraoral scan procedure.

During an intraoral scan procedure (also referred to as a scan session), a user (e.g., a dental practitioner) of an intraoral scanner may generate multiple different images (also referred to as scans or medical images) of a dental site, model of a dental site, or other object. The images may be discrete images (e.g., point-and-shoot images) or frames from a video (e.g., a continuous scan). The intraoral scanner can automatically generate a 3D model of the patient's teeth, which can be used for treatment planning.

As further described herein, an image capture subsystem of an AR display may be used to generate multiple images of a patient's teeth. The image capture subsystem may generate a stream of images, and processing logic may analyze the stream of images to select a subset of those images. The selected subset of images may then be saved and used to generate a model associated with a dental arch or jaw, such as an articulation model of the patient's jaw. Additionally, a dental practitioner wearing the AR display may generate voice notes and append those voice notes to images taken by the image capture subsystem of the AR display.

As described herein, an AR system is a device that enables a live direct or indirect view of a physical, real-world environment and that augments the view of the physical real-world environment by computer generated sensory input such as sound, video, or graphics. An AR system may include an AR display that includes glasses or other lenses that have one or more cameras attached to capture images of a patient. The AR display may also have a projector that projects images onto the glasses or lenses to provide a visual overlay to a dental practitioner. The visual overlay can be superimposed over the real world image that the dental practitioner sees through the glasses or lenses. The AR display can be worn by a dental practitioner, and can include AR glasses, AR goggles, or an AR headset. While some embodiments described herein are discussed with reference to a worn AR display, it should be understood that the AR system can use other types of displays.

Additionally, it should be understood that reference to an AR system also apply to a virtual reality (VR) system. A VR system is similar to an AR system, except that an AR system allows a wearer or viewer to see an augmented version of the real world, while a VR system provides a purely simulated environment. A VR system artificially creates sensory experiences that can include sight, touch, sound, and/or other senses, and presents these sensory experiences onto a VR display. Any reference made herein to any type of AR system and/or AR display applies equally to a VR system and/or VR display.

FIG. 1A illustrates one embodiment of an AR system 100 for providing augmented reality enhancements to a dental practitioner. The AR system 100 includes a computing device 105, an AR display 150, a patient display 155, an image capture subsystem 160, and a data store 110. In some embodiments, the image capture subsystem 160 is a component of the AR display 150. In some embodiments, multiple components shown in FIG. 1A may be integrated into a device that houses the AR display 150. For example, the computing device 105 and image capture subsystem 160 may be integrated into glasses or a headset to be worn by a dental practitioner. In some embodiments, the computing device 105 may be separate from the AR display 150, but connected through either a wired or wireless connection to a processing device in the AR display 150. Additionally, the data store 110 may be attached to the AR display 150, may be directly connected to computing device 105, and/or may be accessed by computing device 105 over a network (not shown). In some embodiments, the computing device 105 and data store 110 may be collocated and accessed by the AR display 150 over a network.

Computing device 105 may include a processor, memory, secondary storage, one or more input devices (e.g., such as a keyboard, mouse, tablet, speakers, or the like), one or more output devices (e.g., a display, a printer, etc.), and/or other hardware components. Computing device 105 may be connected to data store 110 either directly or via a network. The network may be a local area network (LAN), a public wide area network (WAN) (e.g., the Internet), a private WAN (e.g., an intranet), or a combination thereof. The computing device 105 may be integrated into the AR display 150 or image capture subsystem 160 in some embodiments to improve mobility.

Data store 110 may be an internal data store, or an external data store that is connected to computing device 105 directly or via a network. Examples of network data stores include a storage area network (SAN), a network attached storage (NAS), and a storage service provided by a cloud computing service provider. Data store 110 may include a file system, a database, or other data storage arrangement.

Figure 1B:
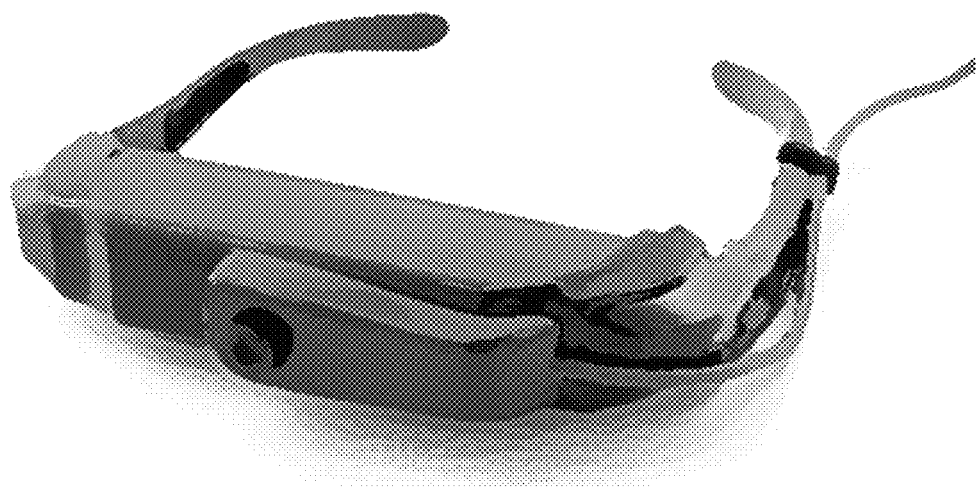
FIGS. 1B-1E show variations of an AR and VR displays, according to the present disclosure.
Figure 1C:
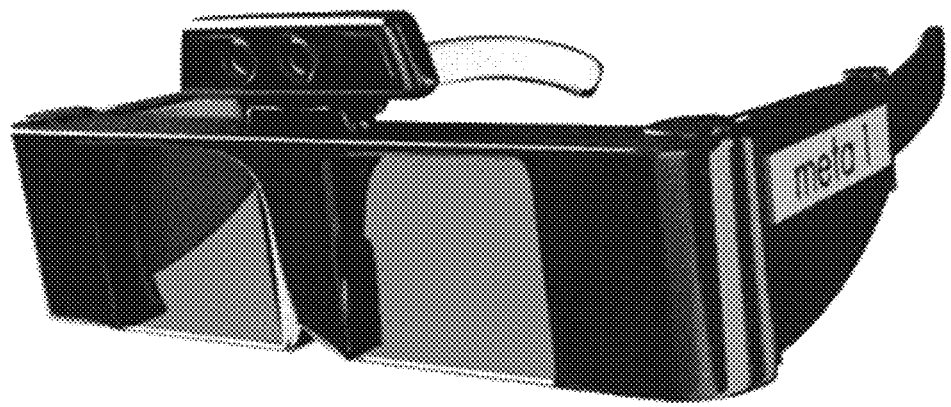
Figure 1D:
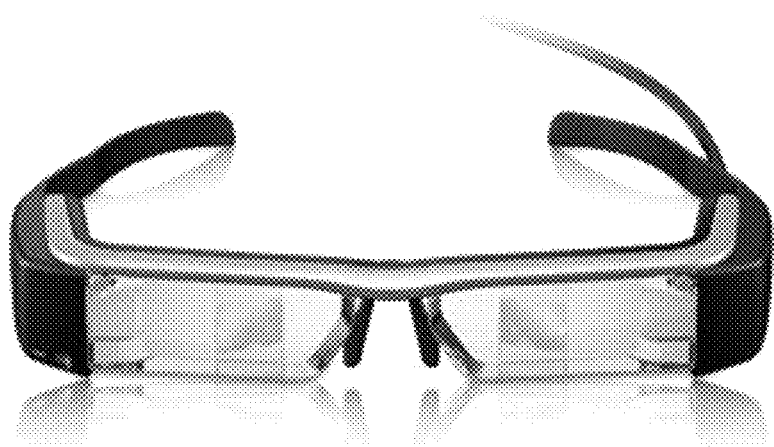
Figure 1E:
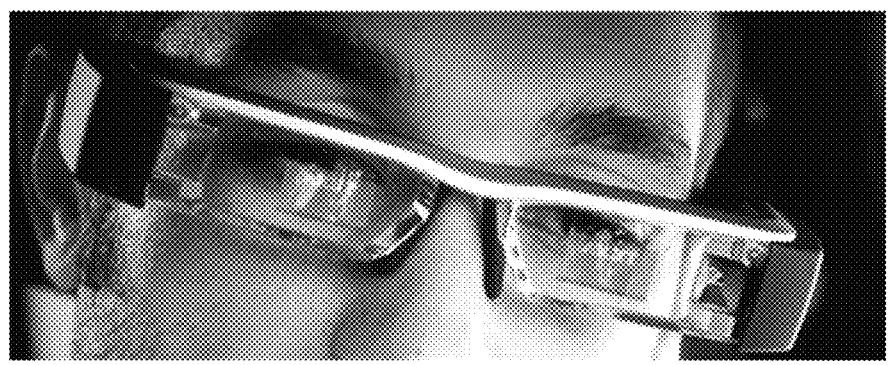

The AR display 150 may include lenses through which a wearer (e.g., a dental practitioner) may see a physical, real-world environment (e.g., a patient's oral cavity) and a projector for projecting visual elements onto the lenses. Examples of AR displays include HoloLens®, Google Glass®, Vuzix Smart Glasses®, and Sony SmartEyeGlass®. Examples of AR displays are shown in FIGS. 1C-1E. The AR display 150 may therefore overlay information for a dental practitioner onto the lenses in a position in the field of view of the practitioner that corresponds to a location of an identified area of interest. To determine where to display information, the AR display 150 may include one or more sensors to track the eyes of a user and/or determine a position of the user in relation to positions of objects viewed by the user. The AR display 150 may also use images provided from image capture subsystem 160 to determine where to display information to the dental practitioner. In some embodiments, the image capture subsystem 160 is mounted to the AR display 150.

The patient display 155 may be similar to the AR display 150 as described above, or alternatively, may be a VR or head-mounted display in which the patient cannot see the physical, real-world environment. An example of a VR display is shown in FIG. 1B. The patient display may have one or two small displays, with lenses and semi-transparent mirrors embedded in eyeglasses, a visor, or a helmet. The display(s) may include cathode ray tubes (CRT), liquid crystal displays (LCDs), liquid crystal on silicon (LCos), or organic light-emitting diodes (OLED). The image data from the image capture subsystem 160 and/or the visual overlay generated based on the image data may be output to the patient display 155. This may enable the patient to view dental conditions of his teeth or gums that a dental practitioner is seeing (and possibly describing). This may facilitate an explanation of the dental conditions to the patient by the dental practitioner. Image data from the image capture subsystem and/or visual overlays may also be sent to the VR display, for example, during dental procedures.

The image capture subsystem can include one or more camera(s) 179. The camera(s) may comprise high definition cameras to accurately capture the structure of areas of interest of a patient. In some embodiments, the camera(s) may include one or more cameras that capture a wide field of view and additional cameras for capturing a narrow field of view (e.g., for a region identified as containing an area of interest). In some embodiments, the image capture subsystem 160 may include additional cameras to provide additional streams of image data. Additional cameras may be used to improve three dimensional image quality.

In some embodiments, the image capture subsystem 160 may include one or more light sources to illuminate a patient for capturing images. Such light sources may include infrared, ultraviolet, or other wavelength light sources (e.g., LEDs or the like). These light sources may illuminate an oral cavity to provide additional data over information available from the visible light spectrum. For example, certain wavelengths such as infrared or ultraviolet wavelengths may more clearly show certain dental conditions such as plaque or cavities. In addition, in some embodiments, light sources may provide structured light to enhance three-dimensional mapping of image data received from image capture subsystem 160. For example, the light sources may project lines or a grid onto viewed objects to provide additional information about depth to the computing device 105.

As a dental practitioner wearing the AR display 150 views a patient, the camera(s) 179 of image capture subsystem 160 may generate a stream of images that show the patient from the dental practitioner's point of view. The images may also be displayed on the patient display 155. The camera(s) may be or include a charge-coupled device (CCD) sensor and/or a complementary metal-oxide semiconductor (CMOS) sensor. The image capture subsystem 160 may provide images or video to the computing device 105 for processing. For example, the image capture subsystem 160 may provide images to the computing device 105 that the computing device analyzes to determine areas of interest on a dental arch or otherwise in an oral cavity viewed by a dental practitioner. The image capture subsystem 160 may also provide images to the computing device 105 or AR display 150 that are used to coordinate the position of elements of a visual overlay to display on AR display 150 so that the visual overlay is superimposed over the real-world environment viewed by the dental practitioner. In some embodiments, the images captured by the camera(s) may be stored in data store 110. For example, the image data 135 may be stored in data store 110 as a record of patient history or for computing device 105 to use for analysis of the patient. The image capture subsystem 160 may transmit the discrete images or video to the computing device 105. Computing device 105 may store the image data 135 in data store 110.

In some embodiments, the image capture subsystem 160 provides two-dimensional data. In some embodiments, the image capture subsystem 160 may provide three-dimensional data or stereoscopic image data that may be processed to produce three-dimensional data. For example, the image capture subsystem 160 may have two cameras with a known separation and known imaging angles that simultaneously capture image data. The stereoscopic image data may be provided to computing device 105 as a single stream of image data or as two separate streams of image data. The stereoscopic image data may be used to provide an estimation of depth for objects viewed through the AR display 150. For example, the computing device 105 may use the stereoscopic image data to identify a three dimensional location of a tooth in the field of view of the image capture subsystem 160.

The image capture subsystem 160 can further include an intraoral scanner 180. In one embodiment, the intraoral scanner 180 includes an image sensor, a communication module and one or more inputs (e.g., buttons, a touch sensor, switches, sliders, etc.). The image sensor generates intraoral images of a patient and the communication module transmits those intraoral images to computing device 105. The computing device may then display the intraoral images or a representation of the dental arch of the patient generated from the intraoral images (e.g., a virtual 3D model of a dental site of the patient) via a visual overlay sent to the AR display 150 or patient display 155. A user may then use the one or more inputs from the intraoral scanner, motion gestures, or other inputs to manipulate the intraoral images or the representation (e.g., virtual 3-D model) generated from the intraoral images. The intraoral images or virtual 3-D model may be shown in the AR display as they are manipulated.

Intraoral scanner 180 may include a probe (e.g., a hand held probe) for optically capturing three dimensional structures (e.g., by confocal focusing of an array of light beams). Intraoral scanner 180 may also include other components such as optical components, an accelerometer, communication components, a gyroscope, processing devices, and so on. One example of an intraoral scanner 180 is the iTero® intraoral digital scanner manufactured by Align Technology, Inc.

The intraoral scanner 180 may be used to perform an intraoral scan of a patient's oral cavity. A result of the intraoral scan may be a sequence of intraoral images that have been discretely generated (e.g., by pressing on a "generate image" button of the scanner for each image). Alternatively, a result of the intraoral scan may be one or more videos of the patient's oral cavity. An operator may start recording the video with the intraoral scanner 180 at a first position in the oral cavity, move the intraoral scanner 180 within the oral cavity to a second position while the video is being taken, and then stop recording the video. The intraoral scanner 180 may transmit the discrete intraoral images or intraoral video to the computing device 105. Computing device 105 may store and/or process the discrete intraoral images or intraoral video in data store 110.

Once an intraoral scan is complete, the processor can use the intraoral scan data from the one or more scans of the various segments to generate a virtual 3D model of a scanned dental site. The dental practitioner can view the scans in detail at various angles by rotating, moving, zooming in or out, etc. of the virtual 3D model. The dental practitioner may make a determination whether the quality of the scans are adequate, or whether particular segments or portions of segments should be rescanned. The dental practitioner may also navigate back to the scan mode to perform additional scans. Once the scans are complete, the scans and/or virtual 3D model can be stored in data store 110 as reference data 138.

The computing device 105 may include AR processor 108. The AR processor 108 may analyze image data 135 from a data store 110 or directly from an image capture subsystem 160. The AR processor 108 may then identify areas of interest to present in a visual overlay on AR display 150 and/or generate additional information to present on the AR display 150. The information provided on an AR display 150 may depend on a procedure to be performed, a wearer of the AR display 150, information known about a patient, and so on. For example, during a routine checkup, the computing device 105 may provide patient history to a dental practitioner and/or display areas of interest identified based on image data 135.

In one embodiment, AR processor 108 includes a display control 118, an input processor 120, an interaction processor 122, and a modified patient data processor 156.

Display control 118 is responsible for determining how to present and/or call out the identified areas of interest on the AR display 150. AR display control 118 may provide indications or indicators highlighting identified AOIs. The AR display control 118 may determine a position to project a virtual object in a visual overlay on an AR display 150 such that the overlay is positioned in the line of sight of the dental practitioner over the AOI. The virtual object may include text, numbers, a contour, colors, graphical images and/or other virtual objects. For instance, the AR display control 118 may determine from the position of the AOI in the image data 135 a corresponding position to project an indicator or indication on the AR display 150. As an example, the AR display control may provide an indication of wear on a tooth by highlighting the worn area on the tooth in a notable color (e.g., that contrasts with a background on which the indication is superimposed) and/or or by providing an indicator pointing to the tooth. In some embodiments, the AR display 150 may provide additional indicators separate from a position corresponding to the AOI in order to provide additional data to a dental practitioner.

The AR display control 118 may provide the indications in the form of flags, markings, contours, text, images, and/or sounds (e.g., in the form of speech). In some embodiments, the AR display module 118 may provide a contour (e.g., via contour fitting) so as to follow a tooth contour or gingival contour in the image data 135. As an illustration, a contour corresponding to a tooth wear diagnostic assistance indication may be placed so as to follow a contour of the worn tooth. A contour may also follow a previous contour of the tooth or other dental feature. For example, a visual overlay may include a contour showing a previous shape of a tooth, or a difference between a previous shape of a tooth and a current shape of the tooth. Such a contour may be placed in the visual overlay so as to be superimposed over the real-world view of the tooth in question or adjacent (e.g., touching) the tooth in question. As an illustration, a contour corresponding to a previous or future position of a tooth may be displayed so as to follow the projected path of the tooth portion which is missing, or a contour corresponding to missing gingival scan data may be placed so as to follow the projected path of the gingival portion which is missing.

Input processor 120 handles all inputs from the display 150 or patient display 155. For example, the input processor 120 may identify virtual selections by a user that are captured by the camera(s) of the image capture subsystem. The virtual selections may be, for example, a hand gesture of the user that identifies the virtual selection, such as by virtually tapping, touching, or selecting one or more of the patient's teeth. The input processor 120 can access data store 110 to use image data 135, reference data 138, and patient data 140 while compiling the virtual selections.

Interaction processor 122 processes virtual manipulations of the virtual selections described above. For example, a user can virtually manipulate the virtual selections with hand gestures by virtually moving, expanding, or rotating the virtual selection to a new position or orientation. The interaction processor 122 identifies these virtual manipulations and applies the manipulation to image data 135, reference data 138, and patient data 140, to determine a virtual overlay corresponding to the new position and orientation of the virtual selection.

Any of the apparatuses described herein may be configured to provide additional output to a patient or third party, in addition to the output provided to the dental professional (e.g., in addition to display 150 in FIG. 1A). This patient-specific output may be modified from the data and output shown to the dental professional. For example, this output may be modified to include less, different, or time-delayed versions of the output displayed to the primary user, the dental professional. Thus, any of these apparatuses may include a modified patient data processor 156 that is connected to the patient display 155. In some examples, the patient display is configured to simplify the output shown to the patient, compared to the primary user.

The computing device 105 can further include feature recognition processing 124, which is responsible for identifying areas of interest (AOIs) from image data 135 received from image capture subsystem 160. The image data may be images of a patient's oral cavity viewed by a dental practitioner wearing the AR display 150. The feature recognition processing 124 may also identify AOIs from reference data 138, which may include patient history, virtual 3D models generated from intraoral scan data, or other patient data. Such areas of interest may include areas indicative of tooth wear, areas indicative of tooth decay, areas indicative of receding gums, a gum line, a patient bite, a margin line (e.g., margin line of one or more preparation teeth), and so forth. Areas of interest may also include areas indicative of foreign objects (e.g., studs, bridges, etc.), areas for the dental practitioner to perform planned treatment, or the like. Furthermore, feature recognition processing 124 may identify error conditions with a dental appliance on the patient's teeth, such as poor fit, poor attachment, etc. The feature recognition processing 124 may, in identifying an AOI, analyze patient image data 135. The analysis may involve direct analysis (e.g., pixel-based and/or other point-based analysis), the application of machine learning, the application of image registration, and/or the application of image recognition. The feature recognition processing 124 may identify areas of interest directly from the image data 135 received from the image capture subsystem 160 or based on a comparison of the received image data 135 and reference data 138, or previous patient data 140. For example, the feature recognition processing 124 may use one or more algorithms or detection rules to analyze the shape of a tooth, color of a tooth, position of a tooth, or other characteristics of a tooth to determine if there is any AOI that should be highlighted for a dental practitioner. Examples of machine learning techniques (including in particular, deep learning for use with dental applications) may be found, for example, in U.S. provisional patent application No. 62/582, 785, titled "DEEP LEARNING FOR TOOTH DETECTION AND EVALUATION," filed on Nov. 7, 2017, herein incorporated by reference in its entirety.

Figure 2:
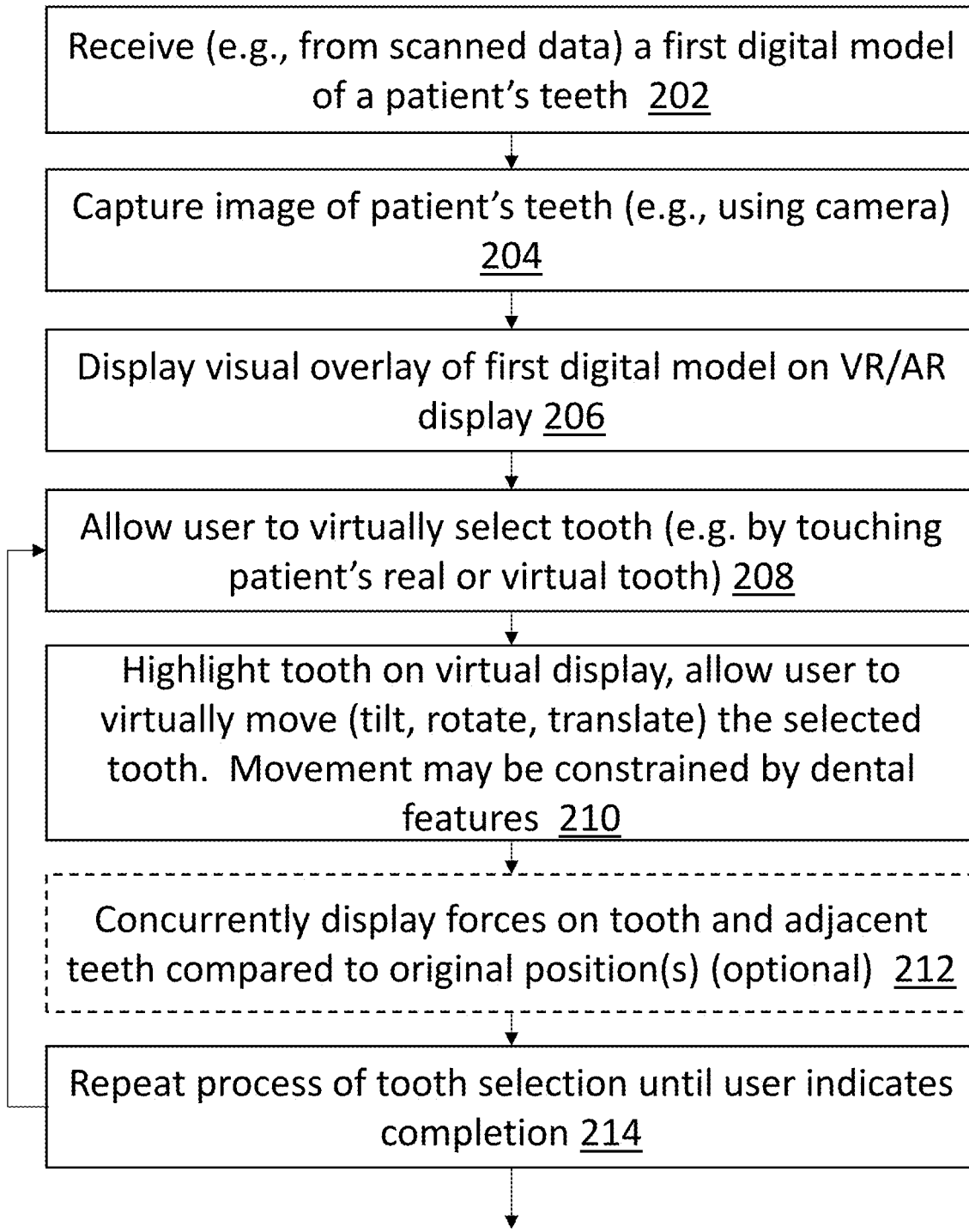
FIG. 2 is a flowchart describing the use of an AR system to develop a treatment plan for an orthodontic patient.

FIG. 2 is a flowchart describing the use of an AR system to develop a treatment plan for an orthodontic patient. At step 202 of the flowchart, the AR system can receive a first digital model of a patient's teeth representing a dental arch. For example, referring to FIG. 1A, processor 108 can receive scans and/or virtual 3D models of the patient's teeth from reference data 138 of data store 110.

At step 204 of the flowchart, the AR system can capture one or more images of the patient's teeth. Referring again to FIG. 1A, camera(s) 179 of the image capture subsystem 160 can capture 2D or 3D images of the patient's teeth. These images can be stored in data store 110 as image data 135.

In some examples, according to step 206 of the flowchart, the first digital model from step 202 can be displayed as a visual overlay onto an AR display of the AR system. A user of the AR display, such as a physician, can view the patient's teeth in real-time along with the visual overlay of the first virtual model over the patient's teeth. Referring to FIG. 1A, display control 118 of the processor 108 can generate the visual overlay from the reference data 138 and display the visual overlay onto the AR display 150.

Next, at step 208 of the flowchart, the AR system allows a user to virtually interact with the patient's teeth. The user can virtually select one or more teeth, or alternatively, add a virtual attachment to one or more of the patient's teeth. The virtual selection can be, for example, physical or virtual touching of the patient's teeth. The virtual selection can be identified by the AR system by evaluating the movement of the user's hand in front of the camera(s) and identifying the position and orientation of the user's hand with respect to the real or first virtual model of the patient's teeth. Referring to FIG. 1A, the input processor 120 and/or interaction processor 122 of the processor 108 compute and process the virtual selection from the user's gestures, the image data 135, and reference data 138.

At step 210 of the flowchart, the AR system can highlight the virtual selection on the AR display by generating a visual overlay identifying the virtual selection. The visual overlay identifying the selection can be, for example, and outline of the selection, or visual shading or colorizing of the selected one or more teeth.

Still at step 210, the user can virtually manipulate the virtual selection, such as by moving, tilting, rotating, or translating the virtual selection. For example, the physician can select one or more teeth (again captured by the camera(s) of the AR system), and can virtually move those teeth to a different position in the patient's jaw, or rotate the one or more teeth to be in a more optimal position. The first digital model of the patient's teeth can be updated in the system to reflect the virtual manipulation, and the visual overlay can be updated and displayed to correspond to the virtual manipulation. The movement of the virtual selection can optionally be constrained by dental features of the patient, such as the location of adjacent teeth, the size of the patient's jaw, the jaw or facial shape/structure of the patient, etc. Referring again to FIG. 1A, interaction processor 122 processes the virtual manipulation, and applies the virtual manipulation to the image data 135 and reference data 138 to provide an updated digital model.

At step 212 of the flowchart, the AR system can optionally display forces on the virtually manipulated teeth (and adjacent teeth) compared to the original positions. This can aid a physician in evaluating the effects of a particular manipulation. If the physician determines or sees that the forces acting on the manipulated teeth are too great, the physician may decide to cancel the manipulation or further adjust the position/orientation of the selected teeth.

According to step 214 of the flowchart, steps 208-212 can be repeated as desired by the user until the user indicates completion. Upon completion, the first digital model can be stored in reference data 138 of data store 110 as a second or modified digital model.

Figure 3:
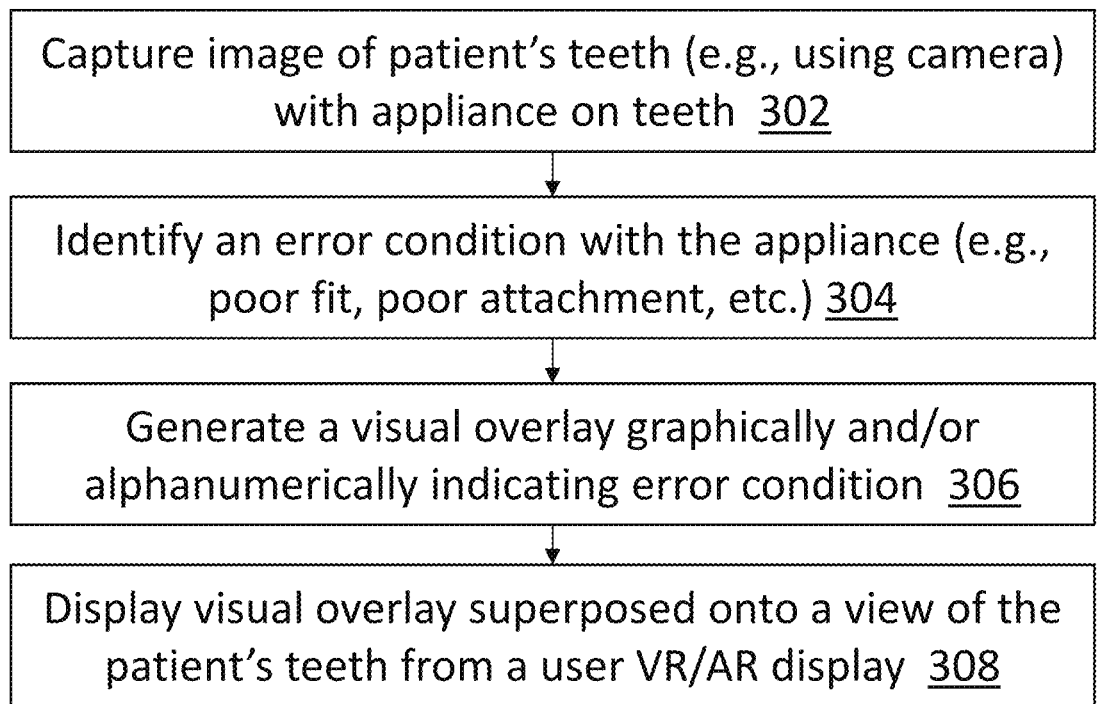
FIG. 3 is a flowchart describing the use of an AR system to evaluate fitment of an orthodontic appliance.

FIG. 3 is a flowchart describing the use of an AR system to evaluate fitment of an orthodontic appliance. At step 302 of the flowchart, the AR system can capture one or more images of the patient's teeth with a dental appliance placed on the teeth. Referring to FIG. 1A, camera(s) 179 of the image capture subsystem 160 can capture 2D or 3D images of the patient's teeth. These images can be stored in data store 110 as image data 135.

Next, at step 304 of the flowchart, the AR system can identify an error condition with the appliance from the images. The error condition can be, for example, improper appliance fit, poor attachment, etc. The error condition can be identified with the feature recognition processing 124 of FIG. 1A, which can identify gaps between the dental appliance and the teeth, bending/warping/deformation of the appliance beyond a threshold, etc.

At step 306 of the flowchart, the AR system can generate a visual overlay that graphically and/or alphanumerically indicates the error condition. The visual overlay can comprise outlines, shading, coloring, etc. Referring to FIG. 1A, display control 118 of the processor 108 can generate the visual overlay from the reference data 138 and image data 135.

At step 308 of the flowchart, the visual overlay from step 306 can be displayed onto an AR display of the AR system.

A user of the AR display, such as a physician, can view the patient's teeth and dental appliance in real-time along with the visual overlay that graphically or alphanumerically indicates the error condition. Referring to FIG. 1A, display control 118 of the processor 108 can generate the visual overlay from the reference data 138 and image data 135 and display the visual overlay onto the AR display 150.

Figure 4A:
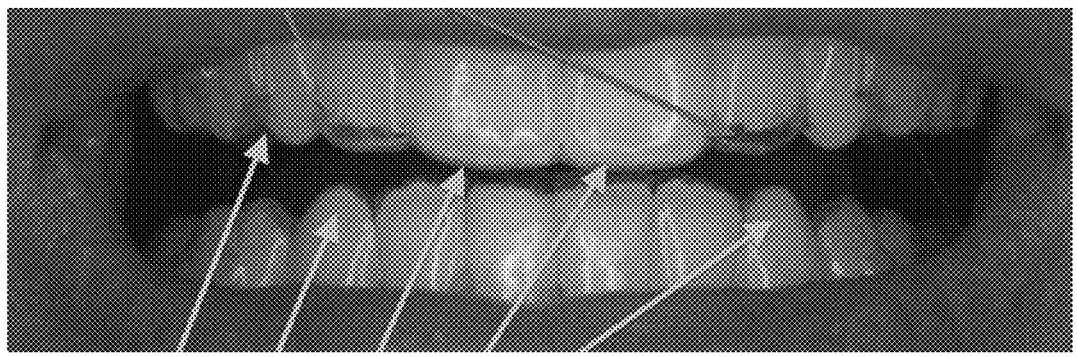
FIG. 4A illustrates examples of both good fit and poor fit in a dental appliance, and provides an example of what the error condition visual overlay of FIG. 3 may look like from the user's perspective.

FIG. 4A illustrates examples of both good fit and poor fit in a dental appliance, and provides an example of what the error condition visual overlay of FIG. 3 may look like from the user's perspective. Additionally, error conditions can be identified in the visual overlay with outlines or shading/color. For example, good/poor fit of an appliance may be identified by highlighting individual problem areas (e.g., red for poor fit, green for good fit). In another example, the visual overlay displays estimated forces acting on the patient's teeth where the forces exceed a threshold value (e.g., poor fit results in high forces acting on the patient's teeth, or an improperly placed band or attachment causes forces to exceed a threshold).

FIGS. 4B and 4C illustrate one example of a method of evaluating an orthodontic treatment (e.g., orthodontic treatment plan). As described in FIG. 4C, the method may be performed in and by an augmented reality apparatus; a physician may wear an AR display device, such as those described above. Initially, the apparatus may receive (e.g., in a processor) a first data set comprising a treatment plan for a patient's teeth 458. A treatment plan may include one or more (typically 4 or more, e.g., 5 or more, 6 or more, etc.) treatment stages, and may include information on the position and orientation (e.g., relative to the dental arch) of the patient's teeth at each step of the treatment plan. The apparatus may additionally or alternatively receive, from an augmented reality system worn by a dental practitioner, an image data set comprising a representation of the patient's current teeth 460. Alternatively or additionally, the apparatus may compare the first data set to the image data set to determine one or more variations from the treatment plan 462. Finally, the method or apparatus configured to perform the method may include displaying the one or more variations on a visual display of the augmented reality system worn by the dental practitioner superimposed over a view of the patient's teeth 464.

FIG. 4B illustrates one example of an overlay (e.g., superposition) display of a dental practitioner-worn AR display, showing deviation between the current position and/or orientation of the patient's teeth and the target position(s) and orientations of the patient's teeth at a later stage (e.g., stage 10, stage 11, stage 12, stage 13, stage 14, stage 15, stage 16, stage 17, etc.). In some variations the comparison may be made at each stage of the treatment plan and/or at the treatment plan having the lowest (e.g., numerically determined) deviation from the current teeth. FIG. 4B illustrates an example of an overlay configured to indicate one or more deviations from one of the treatment stages. In FIG. 4B, the marked region 488 indicates regions that have deviated (e.g., by an amount above a percent difference, e.g., 1%, 2%, 5%, 10%, 15%, 20%, 25%, 40%, 50%, etc.) from the augmented reality target (e.g., goal) of the percentage difference. Unmarked regions 487 show the current tooth positions/orientation.

Figure 5B:
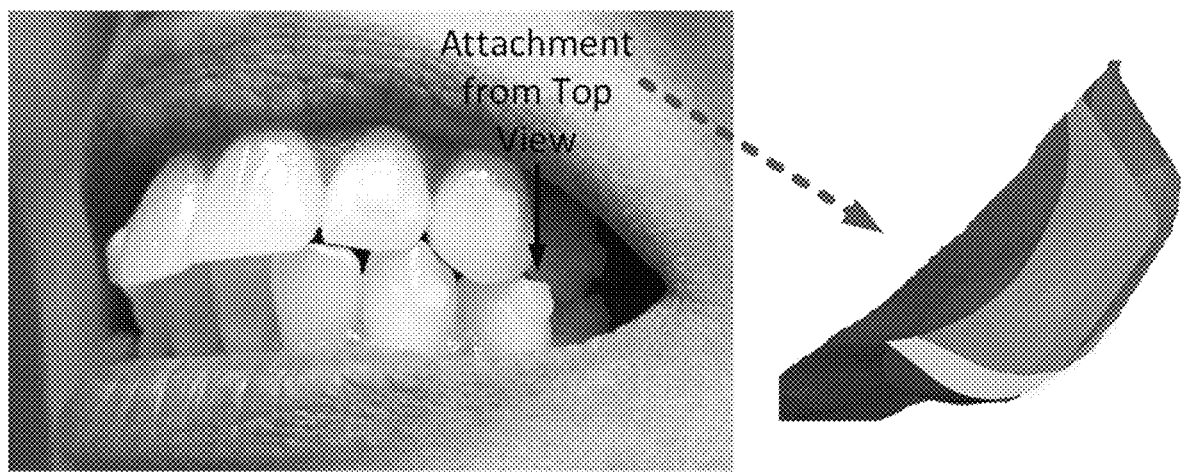
FIG. 5B is an example of a superposition view by an AR system showing mismatch of a planned attachment.
Figure 5A:
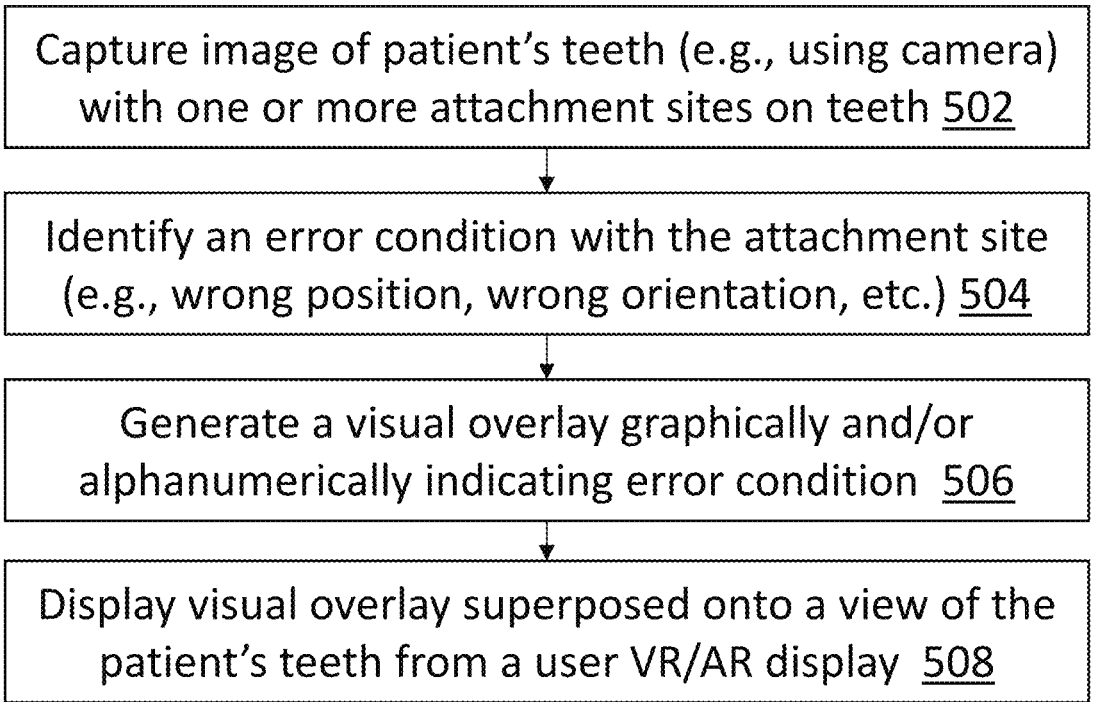
FIG. 5A is a flowchart describing the use of an AR system to evaluate attachments or potential attachments for an orthodontic appliance.

FIG. 5A is a flowchart describing the use of an AR system to evaluate attachments or potential attachments for an orthodontic appliance. At step 502 of the flowchart, the AR system can capture one or more images of the patient's teeth with one or more attachment sites on the teeth. Referring to FIG. 1A, camera(s) 179 of the image capture subsystem 160 can capture 2D or 3D images of the patient's teeth. These images can be stored in data store 110 as image data 135.

Next, at step 504 of the flowchart, the AR system can identify an error condition with the attachment from the images. The error condition can be, for example, an attachment location that differs from a target location, an attachment orientation that differs from a target orientation, improper forces, etc. The error condition can be identified with the feature recognition processing 124 of FIG. 1A, which can evaluate the attachment sites and process the forces applied by the attachment sites to the adjacent teeth to evaluate the effect of applying attachments to the attachment sites.

At step 506 of the flowchart, the AR system can generate a visual overlay that graphically and/or alphanumerically indicates the error condition. The visual overlay can comprise outlines, shading, coloring, force vectors, etc. Referring to FIG. 1A, display control 118 of the processor 108 can generate the visual overlay from the reference data 138 and image data 135.

At step 508 of the flowchart, the visual overlay from step 506 can be displayed onto an AR display of the AR system. A user of the AR display, such as a physician, can view the patient's teeth and attachment sites along with the visual overlay that graphically or alphanumerically indicates the error condition. Referring to FIG. 1A, display control 118 of the processor 108 can generate the visual overlay from the reference data 138 and image data 135 and display the visual overlay onto the AR display 150.

FIG. 5B shows an example of a superposition view by an AR system showing mismatch of a planned attachment position versus a formed attachment. In FIG. 5B (left) the patient's dentition (upper and lower arch) may be visible through the AR system and a virtual image of on attachment (FIG. 5B, right) may be displayed in an overlay atop the view of the dentition. In some variations, the user may rotate or manipulate the virtual image using a tool and/or hand gestures.

Figure 6:
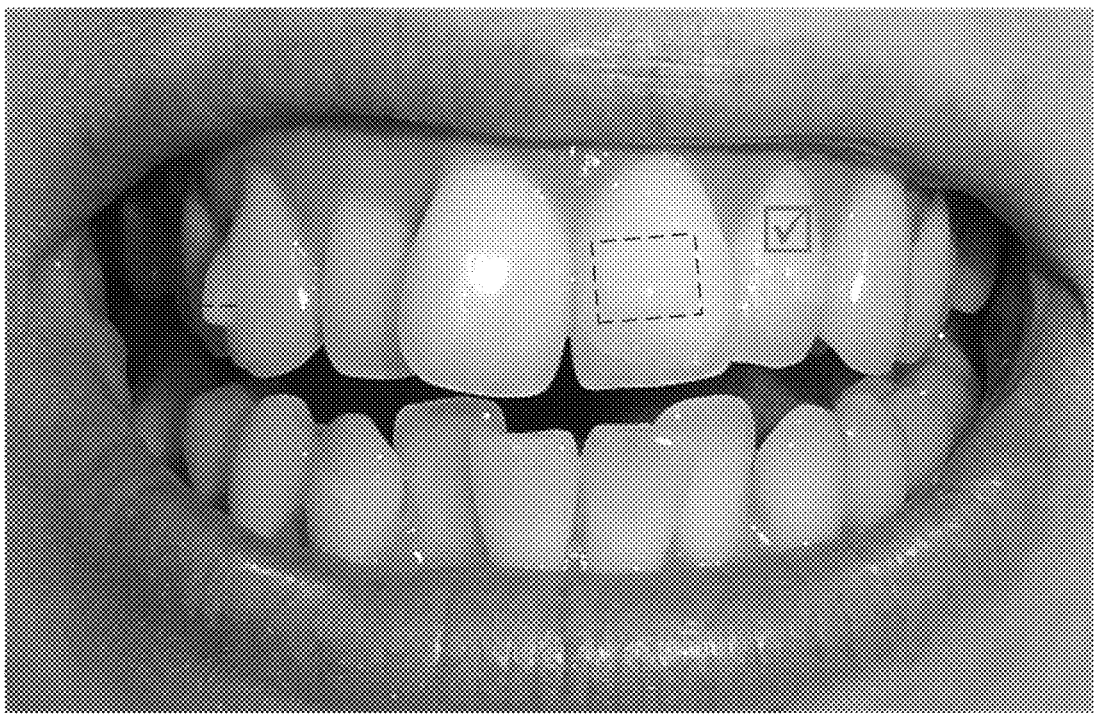
FIG. 6 illustrates examples of what the error condition visual overlay of FIG. 5A may look like from the user's perspective.

FIG. 6 illustrates examples of what the error condition visual overlay of FIG. 5A may look like from the user's perspective. For example, a good potential attachment site may be indicated with a visual marker, outline, or color to indicate its suitability for an attachment point (e.g., green box, check mark, etc.). Similarly, a poor potential attachment site may also be indicated with a visual marker, outline, or color to indicate that it is not a good location for an attachment (e.g., red box, X, etc.). Additionally, the visual overlay can indicate forces applied by a potential attachment site to adjacent teeth, such as with visual force vectors or alphanumeric data indicating the forces (and whether they surpass a force threshold).

Figure 11:
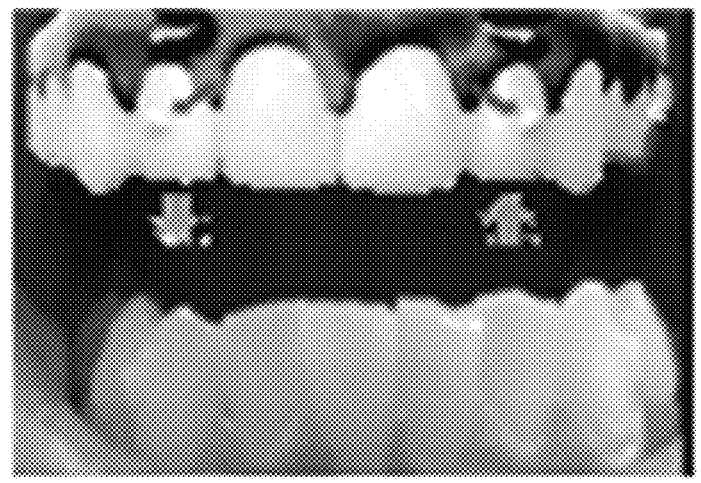
FIG. 11 is an example of an augmented reality (AR) view similar to that seen by a user (e.g., dental professional) operating one of the systems described herein, configured to show force(s) acting on the one or more teeth as a symbol, marking or alphanumeric code.

FIG. 11 illustrates one example of measuring and analyzing forces (including torques) operating on a patient's teeth when wearing an aligner and/or by superimposing the force vector representation onto the current tooth view observed by the dental professional. In FIG. 11, the image shows superimposing force and torques on the patient teeth by AR system.

Figure 7:
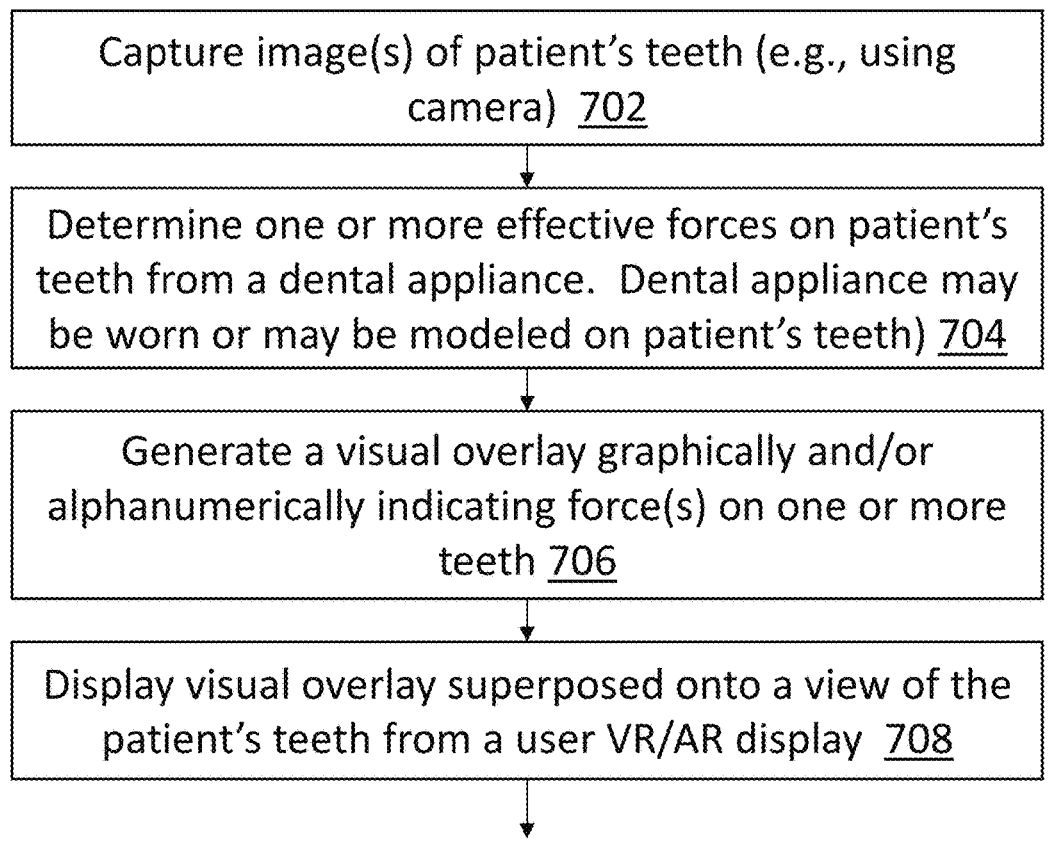
FIG. 7 is a flowchart describing the use of an AR system to display forces on a patient's teeth from an orthodontic appliance.

FIG. 7 is a flowchart describing the use of an AR system to display forces on a patient's teeth from an orthodontic appliance. At step 702 of the flowchart, the AR system can capture one or more images of the patient's teeth with a dental appliance on the teeth. The dental appliance can include, for example, elastic bands or wire based dental appliances that attach to two or more different locations in a patient's jaw. Referring to FIG. 1A, camera(s) 179 of the image capture subsystem 160 can capture 2D or 3D images of the patient's teeth. These images can be stored in data store 110 as image data 135.

Next, at step 704 of the flowchart, the AR system can determine one or more forces on the patient's teeth from the dental appliance. The forces can be identified with the feature recognition processing 124 of FIG. 1A, which can evaluate the dental appliance and process the forces applied by the dental appliance to the patient's teeth. The feature recognition processing 124 can use the image data 135, reference data 138, and patient data 140 to evaluate these forces. In some examples, the feature recognition processing 124 can identify the length and/or angle of elastic bands or wires in the patient's mouth, and calculate the forces applied by the elastic bands or wires to the patient's teeth.

At step 706 of the flowchart, the AR system can generate a visual overlay that graphically and/or alphanumerically indicates the forces on the patient's teeth. The visual overlay can comprise outlines, shading, coloring, force vectors, or alphanumerical data, etc. For example, in a patient with an elastic band attached to two teeth, the visual overlay can provide detailed information on the forces applied to each of the patient's teeth as a result of the elastic band. Furthermore, in some examples, the visual overlay can also include an indication if the forces applied by the dental appliance to the patient's teeth exceed a force threshold. This can indicate to a user that the dental appliance is improperly applying more force to the teeth than is desired. Referring to FIG. 1A, display control 118 of the processor 108 can generate the visual overlay from the reference data 138 and image data 135.

At step 708 of the flowchart, the visual overlay from step 706 can be displayed onto an AR display of the AR system. A user of the AR display, such as a physician, can view the patient's teeth and dental appliance along with the visual overlay that graphically or alphanumerically indicates the forces on the patient's teeth. Referring to FIG. 1A, display control 118 of the processor 108 can generate the visual overlay from the reference data 138 and image data 135 and display the visual overlay onto the AR display 150.

Figure 8:
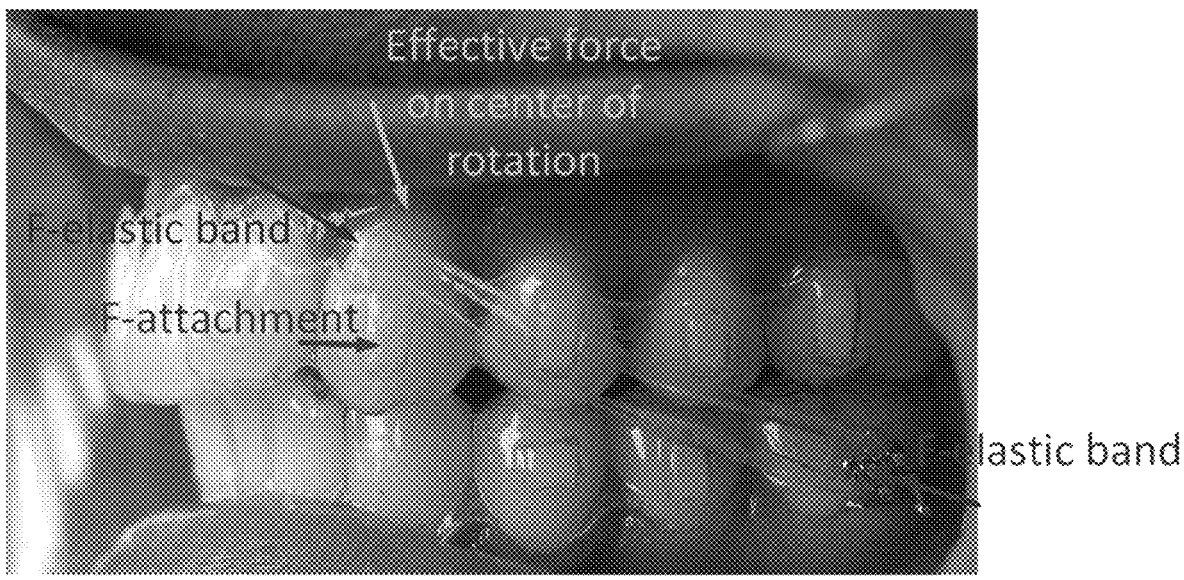
FIG. 8 illustrates examples of what the elastic bands forces visual overlay of FIG. 7 may look like from the user's perspective.
Figure 9:
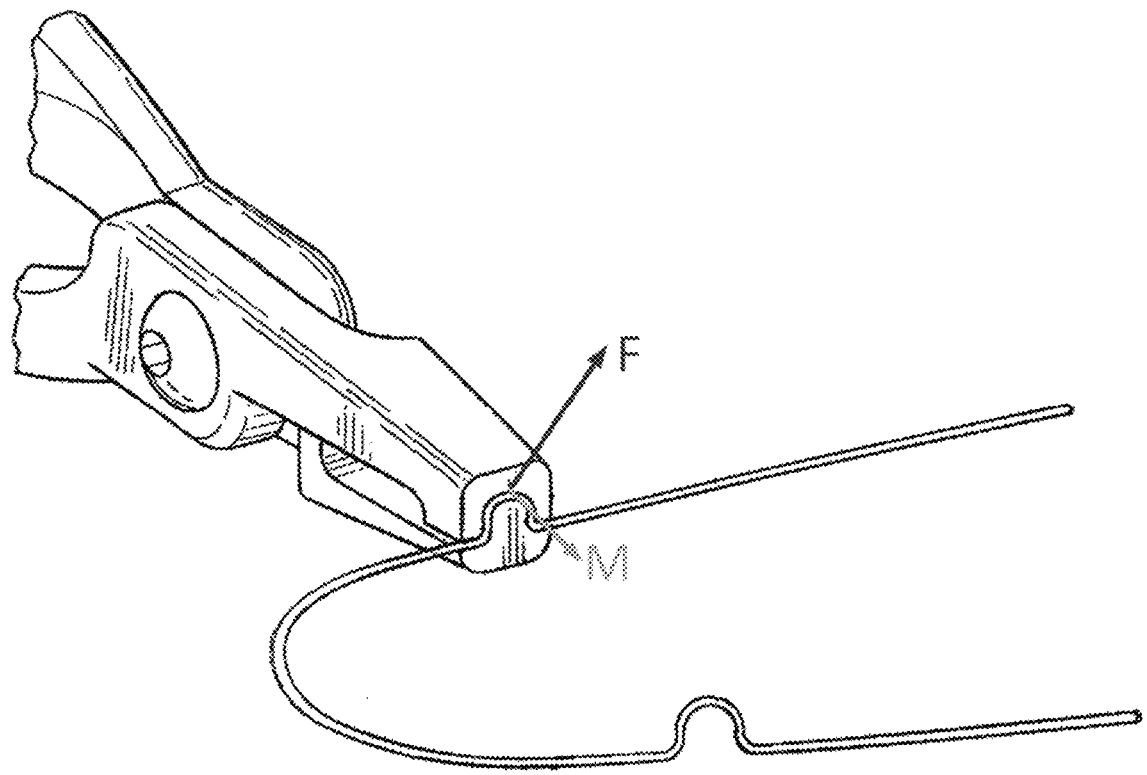
FIG. 9 shows what the metal wire forces visual overlay of FIG. 7 may look like from the user's perspective.

FIG. 8 illustrates examples of what the elastic bands forces visual overlay of FIG. 7 may look like from the user's perspective. FIG. 9 shows what the metal wire forces visual overlay of FIG. 7 may look like from the user's perspective. For example, the forces may be indicated with a visual marker, outline, color, alphanumeric values, or force vectors to indicate the forces applied by the dental appliance to the patient's teeth, and whether they surpass a force threshold.

Figure 10A:
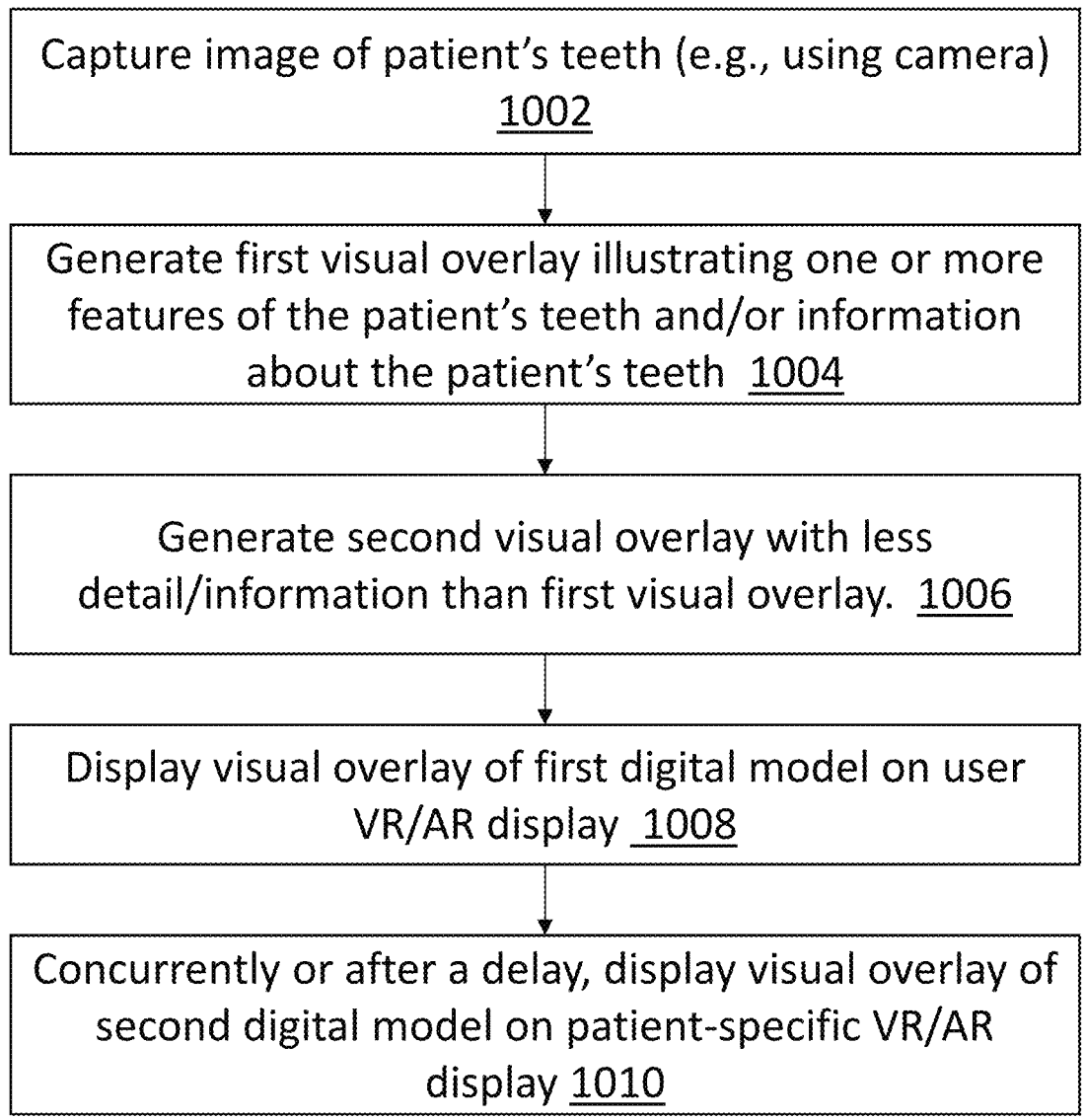
FIG. 10A is a flowchart describing the use of an AR system to dental information to a physician and a patient.

FIG. 10A is a flowchart describing the use of an AR system to dental information to a physician and a patient. At step 1002 of the flowchart, the AR system can capture one or more images of the patient's teeth. The patient can be wearing a dental appliance during the image capture, or can be preparing for a new dental appliance. Referring to FIG. 1A, camera(s) 179 of the image capture subsystem 160 can capture 2D or 3D images of the patient's teeth. These images can be stored in data store 110 as image data 135.

Next, at step 1004 of the flowchart, the AR system can generate a first visual overlay that illustrates one or more features of the patient's teeth or provides information about the patient's teeth or dental appliance. The visual overlay can comprise any of the visual overlays described above, including virtual models of the patient's teeth, error conditions with fitment of a dental appliance, attachment points on a patient's teeth, force applied by a dental appliance to the patient's teeth, etc. Furthermore, as described above, the visual overlay can include outlines, shading, coloring, force vectors, or alphanumerical data, etc. The first visual overlay can be tailored with the type of information that would be useful to a practitioner, such as a physician or orthodontist. Referring to FIG. 1A, display control 118 of the processor 108 can generate the visual overlay from the reference data 138 and image data 135.

At step 1006 of the flowchart, the AR system can generate a second visual overlay that includes less detail/information than the first overlay of step 1004. The second visual overlay can be tailored with the type of information that would be useful to a patient. For example, technical information such as force vectors and advanced treatment planning would not be included in the second visual overlay. However, the second visual overlay may be used to show a patient what their teeth will look like after treatment, or to show a patient specific issues with their teeth or their current dental appliance.

At step 1008 of the flowchart, the visual overlay from step 1004 can be displayed onto a user AR display of the AR system. The user display is reserved for a physician or practitioner who can view the patient's teeth and dental appliance along with the visual overlay. Referring to FIG. 1A, display control 118 of the processor 108 can generate the visual overlay from the reference data 138 and image data 135 and display the visual overlay onto the AR display 150.

At step 1010 of the flowchart, the visual overlay from step 1006 can be displayed onto a patient specific AR or VR display of the AR system. The patient specific display is reserved for the patient, who can view the less detailed visual overlay while being evaluated by the user. The second visual overlay can be a useful tool for the user to explain the treatment plan and/or procedure to the patient. Referring to FIG. 1A, display control 118 of the processor 108 can generate the visual overlay from the reference data 138 and image data 135 and display the visual overlay onto the AR display 150.

Figure 10B:
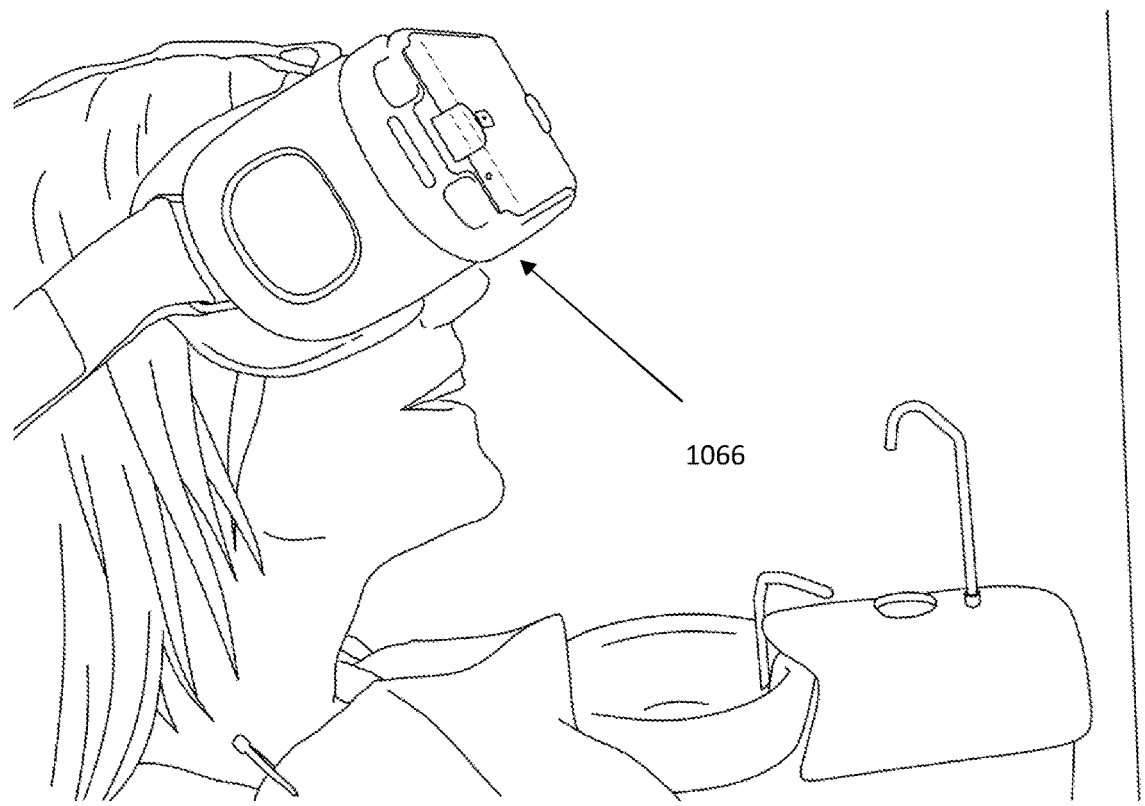
FIG. 10B shows an example of a patient wearing a slave patient-wearable display device (e.g., VR device) that may be controlled by a master dental professional-wearable AR device, as shown in FIG. 10C.
Figure 10C:
FIG. 10C is an illustration of a master/slave AR/VR system in which the dental professional wears an AR display device that may provide augmented information overlaid onto the view of the patient's dentition, while the patient is shown a virtual reality view including the perspective seen by the dental professional (the AR view) onto which all or a subset of the information displayed to the dental professional from the AR view is overlaid.

FIGS. 10B and 10C illustrate an example of an AR (and/or combined AR/VR) system including a master/slave relationship. In this example, the patient may watch what the dental professional is seeing on the AR system worn by the dental professional. The dental professional may show the patient one or more features that the dental professional may want to explain. For example, if the dental professional touches a tooth, the patient's screen can zoom on that particular tooth and show what the dental professional wants to explain. As shown in FIG. 10B, the patient may wear a patient display 1066 and the dental professional may wear an AR device including a display and one or more cameras.

Examples of planning and fabrication of orthodontic aligners, including elastic polymeric positioning appliances, are described, e.g., in U.S. Pat. No. 5,975,893, and in published PCT application WO 98/58596, which is herein incorporated by reference for all purposes.

The diagram of FIG. 1 shows an example of an AR system 100. The system components may be modular, e.g., may include one or more modules (sub-portions) of the AR system that may include one or more engines and datastores. A computer system can be implemented as an engine, as part of an engine or through multiple engines. As used herein, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, datastores are intended to include repositories having any applicable organization of data, including tables, comma-separated values (CSV) files, traditional databases (e.g., SQL), or other applicable known or convenient organizational formats. Data stores can be implemented, for example, as software embodied in a physical computer-readable medium on a specific-purpose machine, in firmware, in hardware, in a combination thereof, or in an applicable known or convenient device or system. Data store-associated components, such as database interfaces, can be considered "part of" a data store, part of some other system component, or a combination thereof, though the physical location and other characteristics of data store-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based data store is a data store that is compatible with cloud-based computing systems and engines.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of evaluating an orthodontic treatment, the method comprising:
   receiving, in a processor, a first data set comprising a treatment plan for a patient's teeth;
   receiving, from an augmented reality system worn by a dental practitioner, an image data set comprising a representation of the patient's current teeth;
   comparing the first data set to the image data set to determine one or more variations from the treatment plan, wherein the one or more variations includes one or more regions of the patient's current teeth that deviate from the patient's teeth at a stage of the treatment plan; and
   displaying the one or more variations on a visual display of the augmented reality system worn by the dental practitioner superimposed over a view of the patient's teeth.

2. The method of claim 1, further comprising receiving a virtual model of a patient's teeth representing a dental arch, and further comprising determining positions and orientations of one or more of the patient's teeth relative to the dental arch from the image data set comprises matching the image data of the patient's teeth to a virtual model of the patient's teeth to identify corresponding teeth from the image data of the patient's teeth.

3. The method of claim 2, wherein the virtual model of the patient's teeth comprises a scan taken prior to a start of the orthodontic treatment.

4. The method of claim 1, wherein displaying the variations comprises displaying a color on the view of the patient's teeth.

5. The method of claim 1, further comprising identifying a stage of the treatment plan most closely corresponding to an arrangement of the patient's current teeth and wherein comparing the first data set to the image data set comprises comparing the stage of the treatment plan most closely corresponding to the arrangement of the patient's current teeth with the image data set to determine one or more variations.

6. The method of claim 5, wherein identifying the stage of the treatment plan comprises receiving the stage from the dental practitioner.

7. The method of claim 5, wherein identifying the stage of the treatment plan comprise identifying the stage with a lowest value for the one or more variations.

8. The method of claim 1, wherein comparing the first data set to the image data set comprises comparing each stage of the treatment plan of the first data set to the image data set and further wherein displaying the one or more variations comprises displaying the one or more variations specific to each stage of the treatment plan.

9. The method of claim 1, wherein the one or more variations comprise one or more of: a difference in a tooth position relative to the patient's dental arch between a tooth of the patient's current teeth and a corresponding position of the tooth in a stage of the treatment plan from the first data set; a difference in an angle of the tooth relative to the patient's dental arch of the patient's current teeth and a corresponding angle of the tooth in a stage of the treatment plan of the first data set; and a difference in rotational position relative to the patient's dental arch of a tooth between a tooth of the patient's current teeth and a corresponding rotational position of the tooth in a stage of the treatment plan of the first data set.

10. A system comprising:
   an augmented reality display;
   one or more processors;
   a memory coupled to the one or more processors, the memory configured to store computer-program instructions, that, when executed by the one or more processors, perform a computer-implemented method comprising:
      receiving, in a processor, a first data set comprising a treatment plan for a patient's teeth;
      receiving, from an augmented reality system worn by a dental practitioner, an image data set comprising a representation of the patient's current teeth;
      comparing the first data set to the image data set to determine one or more variations from the treatment plan, wherein the one or more variations includes one or more regions of the patient's current teeth that deviate from the patient's teeth at a stage of the treatment plan; and
      displaying the one or more variations on a visual display of the augmented reality system worn by the dental practitioner superimposed over a view of the patient's teeth.

11. A method of evaluating an orthodontic treatment using an augmented reality system worn by a dental practitioner, the method comprising:
   receiving, in a processor of the augmented reality system, a first data set comprising a treatment plan for a patient's teeth;
   receiving from the augmented reality system, an image data set comprising a representation of the patient's current teeth;
   determining positions and orientations of one or more of the patient's teeth relative to the patient's dental arch from the image data set;
   comparing the positions and orientations of the one or more of the patient's teeth relative to the patient's dental arch with the treatment plan to determine one or more variations from the treatment plan, wherein the one or more variations includes one or more regions of the patient's current teeth that deviate from the patient's teeth at a stage of the treatment plan; and displaying the one or more variations on a visual display of the augmented reality system worn by the dental practitioner superimposed over a view of the patient's teeth.

12. The method of claim 11, further comprising receiving a virtual model of a patient's teeth representing a dental arch, and further wherein determining the positions and orientations of one or more of the patient's teeth relative to the patient's dental arch from the image data set comprises matching the image data of the patient's teeth to a virtual model of the patient's teeth to identify corresponding teeth from the image data of the patient's teeth.

13. The method of claim 12, wherein the virtual model of the patient's teeth comprises a scan taken prior to a start of the orthodontic treatment.

14. The method of claim 11, wherein displaying the variations comprises displaying a color on the view of the patient's teeth.

15. The method of claim 11, further comprising identifying a stage of the treatment plan most closely corresponding to an arrangement of the patient's current teeth and wherein comparing the first data set to the image data set comprises comparing the stage of the treatment plan most closely corresponding to the arrangement of the patient's current teeth with the image data set to determine one or more variations.

16. The method of claim 15, wherein identifying the stage of the treatment plan comprises receiving the stage from the dental practitioner.

17. The method of claim 15, wherein identifying the stage of the treatment plan comprise identifying the stage with a lowest value for the one or more variations.

18. The method of claim 11, wherein comparing the first data set to the image data set comprises comparing each stage of the treatment plan of the first data set to the image data set and further wherein displaying the one or more variations comprises displaying the one or more variations specific to each stage of the treatment plan.

19. The method of claim 11, wherein the one or more variations comprise one or more of: a difference in a tooth position relative to the patient's dental arch between a tooth of the patient's current teeth and a corresponding position of the tooth in a stage of the treatment plan from the first data set; a difference in an angle of the tooth relative to the patient's dental arch of the patient's current teeth and a corresponding angle of the tooth in a stage of the treatment plan of the first data set; and a difference in rotational position relative to the patient's dental arch of a tooth between a tooth of the patient's current teeth and a corresponding rotational position of the tooth in a stage of the treatment plan of the first data set.

* * * * *